US009485972B2

(12) United States Patent
Kontsekovà

(10) Patent No.: US 9,485,972 B2
(45) Date of Patent: Nov. 8, 2016

(54) TRUNCATED TAU PROTEINS

(75) Inventor: Eva Kontsekovà, Sencec (SK)

(73) Assignee: Axon Neuroscience SE, Bratislava (SK)

( * ) Notice: Subject to any disclaimer, the term of this patent is extended or adjusted under 35 U.S.C. 154(b) by 669 days.

(21) Appl. No.: 12/574,414

(22) Filed: Oct. 6, 2009

(65) Prior Publication Data

US 2010/0063250 A1 Mar. 11, 2010

Related U.S. Application Data

(62) Division of application No. 10/521,140, filed as application No. PCT/EP03/07389 on Jul. 9, 2003, now abandoned.

(30) Foreign Application Priority Data

Jul. 12, 2002 (AT) .................................. A 1053/2002

(51) Int. Cl.
| | | |
|---|---|---|
| C07K 14/47 | (2006.01) | |
| A01K 67/027 | (2006.01) | |
| C12N 15/85 | (2006.01) | |
| G01N 33/50 | (2006.01) | |
| G01N 33/68 | (2006.01) | |
| A61K 39/00 | (2006.01) | |

(52) U.S. Cl.
CPC ....... *A01K 67/0278* (2013.01); *C07K 14/4711* (2013.01); *C12N 15/8509* (2013.01); *G01N 33/5088* (2013.01); *G01N 33/6896* (2013.01); *A01K 2207/15* (2013.01); *A01K 2217/00* (2013.01); *A01K 2217/05* (2013.01); *A01K 2217/072* (2013.01); *A01K 2227/105* (2013.01); *A01K 2267/0312* (2013.01); *A61K 39/00* (2013.01); *G01N 2800/2821* (2013.01); *G01N 2800/52* (2013.01)

(58) Field of Classification Search
CPC ................... A01K 2207/15; A01K 2217/00; A01K 2217/05; A01K 2217/072; A01K 2227/105; A01K 2267/0312; A01K 67/0278; A01K 39/00; C07K 14/4711; C12N 15/8509; G01N 2800/2821; G01N 2800/52; G01N 33/5088
USPC .................................. 435/325; 530/324, 350
See application file for complete search history.

(56) References Cited

U.S. PATENT DOCUMENTS

| | | | | |
|---|---|---|---|---|
| 7,446,180 B2 * | 11/2008 | Novak | .................. | 530/388.1 |
| 2002/0010947 A1 | 1/2002 | Gurney | .................. | 800/12 |
| 2002/0164657 A1* | 11/2002 | Sharma et al. | .................. | 435/7.2 |
| 2006/0112437 A1 | 5/2006 | Kontsekova et al. | .................. | 435/6 |

FOREIGN PATENT DOCUMENTS

| | | |
|---|---|---|
| WO | WO 94/18560 | 8/1994 |
| WO | WO 96/30766 | 10/1996 |
| WO | WO 99/62548 | 12/1999 |
| WO | WO9962548 A1 * | 12/1999 |

OTHER PUBLICATIONS

Abraha et al., "C-terminal inhibition of tau assembly in vitro and in alzheimer's disease," *J of Cell Science*, 113:3737-3745, 2000.
Andrä et al., "Expression of APP in transgenic mice: a comparison of neuron-specific promoters," 17(2):183-190, 1996.
Araki et al., "Transgenic rabbits expressing human lipoprotein lipase," *Cytotechnology*, 33:93-99, 2000.
Bornemann and Staufenbiel, "Transgenic mouse models of Alzheimer's disease," *Ann. NY Acad Sci.*, 908:260-266, 2000.
Braak et al., "Staging of Alzheimer disesase-associated neurofibrillary pathology using paraffin sections and immunocytochemistry," *Acta Neuropathol*, 112:389-404, 2006.
Brandt et al., "Functional organization of microtubule-associated protein tau," *The J of Biological Chemistry*, 268:3414-3419, 1993.
Brinster et al., "Factors affecting the efficiency of introducing foreign DNA into mice by microinjecting eggs," *Proc Natl Acad Sci USA*, 82:4438-4442, 1985.
Campbell et al., "Transgenic models to assess the pathogenic actions of cytokines in the central nervous system," *Mol. Psychiatry*, 2(2):125-129, 1997.
Cente et al., "Expression of a truncated tau protein induces oxidative stress in a rodent model of tauopathy," *European Journal of Neuroscience*, 24:1085-1090, 2006.
Charreau et al., "Transgenic rats: Technical aspects and models," *Transgenic Res.*, 5:223-234, 1996.
Esposito et al., "The solution structure of the c-terminal segment of tau protein," *J of Peptide Science*, 6:550-559, 2000.
Fasulo et al., "Overexpression of Alzheimer's PHF core tau fragments: implications for the tau truncation hypothesis," *Alzheimer's Research*, 2:195-200, 1996.
Fasulo et al., "Tau truncation in alzheimer's disease: expression of a fragment encompassing phf core tau induces apoptosis in cos cells," *Alzheimer's Reports*, 1:25-32, 1998.
Fasulo et al., "The neuronal microtubule-associated protein tau is a substrate for caspase-3 and an effector of apoptosis," *J of Neurochemistry*, 75:624-633, 2000.
Fitzsimons et al., "Promoters and regulatory elements that improve adeno-associated virus transgene expression in the brain," *Methods*, 28:227-236, 2002.
Glorioso et al., "HSV as a gene transfer vector for the nervous system," *Mol. Biotechnol.*, 4(1):87-99, 1995.
Götz, "Tau and transgenic animal models," *Brain Research Reviews*, 35: 266-286, 2001.

(Continued)

*Primary Examiner* — Janet Epps-Smith
(74) *Attorney, Agent, or Firm* — Finnegan, Henderson, Farabow, Garrett & Dunner, L.L.P.

(57) ABSTRACT

Described are novel N- and C-terminally double truncated tau molecules, ("type IA, IB, IIA and IIB tau molecules") as well as methods for providing these molecules, both from recombinant and biological sources. Moreover, screening methods using these molecules in connection with Alzheimer's diagnosis and therapy are provided.

10 Claims, 20 Drawing Sheets

(56) References Cited

OTHER PUBLICATIONS

Hammer et al., "Genetic engineering of mammalian embryos," *J. Anim. Sci.*, 63(1):269-278, 1986.
Hammer et al., "Production of transgenic rabbits, sheep and pigs by microinjection," *Nature*, 315(6021):680-683, 1985.
Hammer et al., "Spontaneous inflammatory disease in transgenic rats expressing HLA-B27 and human beta 2m: an animal model of HLA-B27-associated human disorders," *Cell*, 63(5):1099-1112, 1990.
Härtig et al., "Hibernation model of tau phosphorylation in hamsters: selective vulnerability of cholinergic basal forebrain neurons—implications for Alzheimer's disease," *European Journal of Neuroscience*, 25:69-80, 2007.
Hrnkova et al., "Neurodegeneration caused by expression of human truncated tau leads to progressive neurobehavioural impairment in transgenic rats," *Brain Res.*, '1130(1):206-213, 2007.
Huang et al., "Neurofibrillary lesions in experimental aluminum-induced encephalopathy and Alzheimer's disease share immunoreactivity for amyloid precursor protein, A $\beta$, $\alpha_1$—antichymotrypsin and ubiquitin-protein conjugates," *Brain Research*, 771:213-220, 1997.
Ikenaka and Kagawa, "Transgenic systems in studying myelin gene expression," *Dev. Neurosci.*, 17(3):127-136, 1995.
Jicha et al., "Sequence requirements for formation of conformational variants of tau similar to those found in alzheimer's disease," *J of Neuroscience Research*, 55:713-723, 1999.
Kappel, "Regulating gene expression in transgenic animals," *Current Biology*, 3: 548-553, 1992.
Keefer, "Production of bioproducts through the use of transgenic animal models," *Anim. Reprod. Sci.*, 82-83: 5-12, 2004.
Kimchi-Sarfaty et al., "A 'silent' polymorphism in the MDR1 gene changes substrate specificity," *Science*, 315 (5811): 525-528, 2006.
Kontsekova et al., "Quick purification of recombinant human truncated tau proteins for immunoanalysis," *J of Immunological Methods*, 185:245-248, 1995.
Koson et al., "Truncated tau expression levels determine life span of a rat model of tauopathy without causing neuronal loss or correlating with terminal neurofibrillary tangle load," *European Journal of Neuroscience*, 28:239-246, 2008.
Lewis et al., "Neurofibrillary tangles, amyotrophy and progressive motor disturbance in mice expressing mutant (P301L) tau protein," *Nature Genetics*, 25:402-405, 2000.
Logan et al., "Potential use of genetically modified pigs as organ donors for transplantation into humans," *Clin. Exp. Pharmacol. Physiol.*, 26 (12): 1020-1025, 1999.
Moreadith, "Gene targeting in embryonic stem cells: the new physiology and metabolism," *J. Mol. Med.*, 75 (3): 208-216, 1997.
Ngo et al, "Computational complexity, protein structure prediction, and the levinthal paradox," in: Merz Jr. and LeGrand (Eds.), *The Protein Folding Problem and Tertiary Structure Prediction*, Birkhäuser, Basel, pp. 491-495, 1994.
Novak et al., "Molecular characterization of the minimal protease resistant tau unit of the alzheimer's disease pried helical filament," *The EMBO Journal*, 12:365-370, 1993.
Novak et al., "Truncation of tau precedes fragmentation of dna in alzheimer's disease," *Chm. Papers*, 52:429-430, 1998.
Novak, "Truncated tau protein as a new marker for alzheimer's disease," *Acta Virologica*, 38:173-189, 1994.
Office Action received in U.S. Appl. No. 10/521,049, mailed Apr. 5, 2006.
Office Action received in U.S. Appl. No. 10/521,049, mailed Jul. 10, 2006.
Office Action received in U.S. Appl. No. 10/521,049, mailed Apr. 17, 2007.
Office Action received in U.S. Appl. No. 10/521,049, mailed Nov. 28, 2007.
Office Action received in U.S. Appl. No. 10/521,049, mailed May 14, 2008.
Office Action received in U.S. Appl. No. 10/521,049, mailed Nov. 13, 2008.
Office Action received in U.S. Appl. No. 10/521,140, mailed Nov. 10, 2009.
Office Action received in U.S. Appl. No. 10/521,140, mailed Apr. 2, 2009.
Office Action received in U.S. Appl. No. 10/521,140, mailed Sep. 8, 2008.
Office Action received in U.S. Appl. No. 10/521,140, mailed Feb. 7, 2008.
Office Action received in U.S. Appl. No. 10/521,140, mailed Aug. 17, 2007.
Office Action received in U.S. Appl. No. 10/521,140, mailed Apr. 11, 2007.
Parsons, "Peptide hormones," University Park Press, 1-7, 1976.
Philippe et al., "Generation of a monoclonal antibody to the carboxy-terminal domain of tau by immunization with the amino-terminal domain of the amyloid precursor protein," *J of Neuroscience Research*, 46:709-719, 1996.
Quinn, "Neuronal-specific gene expression—the interaction of both positive and negative transcriptional regulators," *Prog. Neurobiol.*, 50(4):363-379, 1996.
Richa, "Production of transgenic mice," In: *Methods in Molecular Biology*, 136:427-434, 2000.
SantaCruz et al., "Tau suppression in a neurodegenerative mouse model improves memory function," *Science*, 309:476-481, 2005.
Shuman, "Production of transgenic birds," *Experentia*, 47:897-905, 1991.
Sigmund, "Viewpoint: are studies in genetically altered mice out of control?" *Arterioscler. Throm. Vase. Biol.*, 20 (6): 1425-1429, 2000.
Si-Hoe and Murphy, "Production of transgenic rodents by the microinjection of cloned DNA into fertilized one-celled eggs," In: *Methods in Molecular Biology*, 97:61-100, 2001.
Ugolini et al., "Co-localization of truncated tau and dna fragmentation in alzheimer's disease neurones," *NeuroReport*, 8:3709-3712, 1997.
Vechterova et al., "DCII: a novel monoclonal antibody revealing Alzheimer's disease-specific tau epitope," *Neuroreport*, 14:87-91, 2003.
Vercauteren et al., "Early dysregulation of hippocampal proteins in transgenic rats with Alzheimer's disease-linked mutations in amyloid precursor protein and presenilin 1," *Molecular Brain Research*, 132:241-259, 2004.
Voet et al., "Chemical Evolution," *Biochemistry*, John Wiley and Sons, 126-128, 1990.
Wang et al., "Diverse stabilities of expression in the rat brain from different cellular promoters in a helper virus-free herpes simplex virus type 1 vector system," *Human Gene Therapy*, 10:1763-1771, 1999.
Williams et al., "Transgenic animals in integrative biology: approaches and interpretations of outcome," *Appl. Physiol.*, 88: 1119-1126, 2000.
Zemlan et al., "Quantification of axonal damage in traumatic brain injury: affinity purification an dcharacterization of cerebrospinal fluid tau proteins," *J of Neurochemicstry*, 72:741-750, 1999.
Zilka et al., "Truncated tau from sporadic Alzheimer's disease suffices to drive neurofibrillary degeneration in vivo," *FEBS Lett.*, 580(15):3582-3588, 2006.

* cited by examiner

| Deletion mutant | Epitope deleted | Apparent affinity [nM] |
|---|---|---|
| SEQ ID NO 1 (239-333, R4) | - | 10 |
| SEQ ID NO 22 (248-333, R4; del 239-247) | A1 | 20 |
| SEQ ID NO 23 (258-333, R4; del 239-257) | A2 | 40 |
| SEQ ID NO 24 (263-333, R4; del 239-262) | A3 | 200 |
| SEQ ID NO 25 (239-333, R4; del 248-262) | A4 | 100 |
| SEQ ID NO 26 (239-333, R4; del 256-262) | A5 | 40 |
| SEQ ID NO 27 (239-333, R4; del 263-267) | A6 | 300 |
| SEQ ID NO 21 (268-333, R4; del 239-267) | A | 10000 |

Construction of recombinant tau type I-II (SEQ ID 1-24):

Construction of recombinant tau type II (SEQ ID 25-27):

Selection of drug candidates not inhibiting healthy tau

| Mabs | ELISA(A492nm) AD – *tau* | healthy *tau* | Immunogen | Epitope | Isotype |
| --- | --- | --- | --- | --- | --- |
| DC44# | 1,42 | 0,31 | AD(Fr.#19)* | aa300-317 | IgM/κ |
| DC82 | 1,81 | 0,12 | AD(Fr.#19)* | aa300-317 | IgG2b/κ |
| DC136 | 1,52 | 0,18 | AD(Fr.#19)* | aa300-317 | IgG2a/κ |
| DC25 | 1,91 | 1,81 | tau43 | aa347-353 | IgG1/κ |
| DC20 | 0,18 | 0,12 | IFNα | ND | IgG1/κ |

ELISA (A492 nm)

| Mabs | Recombinant forms of tau molecules | | |
|---|---|---|---|
| | Double truncated proteins | | Full length |
| | TypeIA (SEQIDNO:1) | TypeIIA (SEQIDNO:12) | six isoforms |
| DC44 | 1,72 | 1,61 | 0,21 |
| DC82 | 1,51 | 1,52 | 0,17 |
| DC136 | 1,59 | 1,78 | 0,13 |
| DC25 | 1,71 | 1,51 | 1,98 |
| DC20 | 0,11 | 0,07 | 0,09 |

DC 20: monoclonal antibody with irrelevant specificity
Shown data represent mean values from three paralles

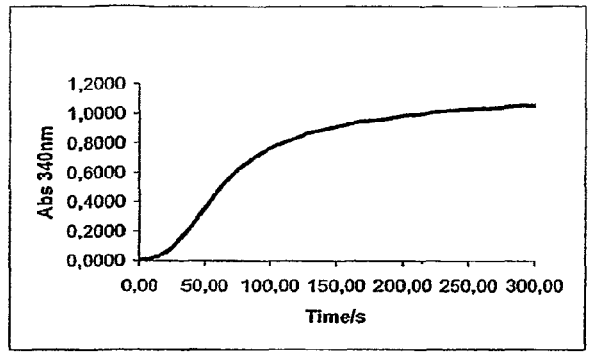

Mikrotubuli-assembly – (Seq. ID 10 und 12) end concentration 100ug/ml; tubulin:

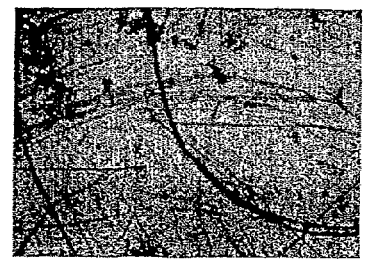

Elektron microscopic analysis of assembled microtubuli in the presence of tau Type IIA (Beispiel - Seq. ID 12). magnification 2600x.

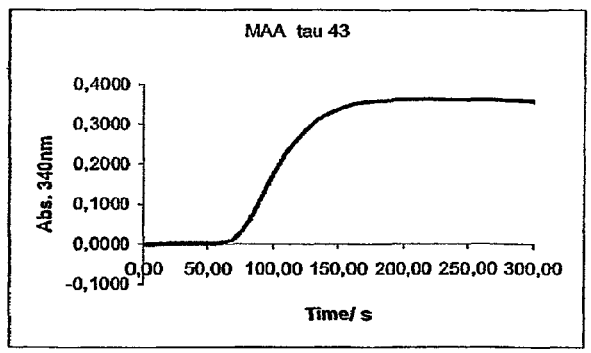

Tau: recombinant isoform Tau 43; end concentration 200ug/ml
Tubulin: end concentration 2mg/ml

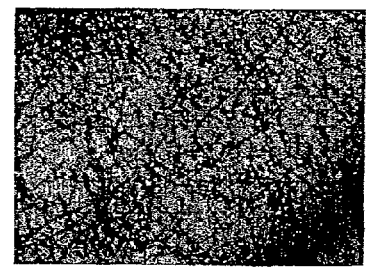

Elektron microscopic analysis of assembled microtubuli in the presence of recombinant tau 43. magnification 2600x.

Fig. 28C

TRUNCATED TAU PROTEINS

CROSS REFERENCE TO RELATED APPLICATIONS

This application is a divisional of U.S. application Ser. No. 10/521,140 filed Oct. 31, 2005, now abandoned which is a national phase application under 35 U.S.C. §371 of International Application No. PCT/EP2003/007389 filed 9 Jul. 2003, which claims priority to Austrian Application No. A 1053/2002 filed 12 Jul. 2002, the contents of which applications are incorporated herein by reference in their entirety.

BACKGROUND OF THE INVENTION

The invention relates to N- and C-terminally truncated diseased forms of tau proteins discovered specifically in Alzheimer's disease and related disorders.

The invention further relates to methods for screening and testing potential drugs effective in inhibiting, neutralising and eliminating N- and C-terminally double truncated tau proteins or preventing the formation of thereof and to procedures for screening and testing potential drugs of which the mode of action is based on neutralising the modification of microtubule assembly and/or dynamics caused by said double truncated diseased forms of tau proteins.

Alzheimer's disease is the most common cause of dementia. In less than 5% of the cases Alzheimer's disease cosegregates almost completely with one or more specific mutations in the amyloid precursor protein, presenilin-1 or presenilin-2 genes (1) and in over 95% of the cases, the exact disease cause is not clear.

Independent of etiology, Alzheimer's disease is characterized histopathologically by the presence of numerous neurons with neurofibrillary tangles of paired helical filaments (PHF) and extracellular deposits of amyloid β as the major component of senile plaques in the brain. Although the exact nature of a direct relationship, if any, between these two hallmark lesions of Alzheimer's disease is presently not understood, the presence of neurofibrillary degeneration appears to be required for the clinical expression of the disease, i.e. dementia (2, 3, 4). Neurofibrillary degeneration is represented by neurofibrillary tangles, dystrophic neurites and neuropil threads. The major protein subunit of these structures is microtubule associated protein tau (5,6).

In healthy human brain tau appears in six protein isoforms generated by alternative mRNA splicing of a transcript derived from a single gene locus. tau proteins differ whether they contain three (t3L, t3S, or t3) or four (t4L, t4S, or t4) tubulin binding domains (repeats, R) of 31 or 32 amino acids near the C-terminal and two (t3L, t4L), one (t3S, t4S), or no (t3, t 4) inserts of 29 amino acids each in the N-terminal part of the molecule (7,8). Under physiological conditions tau protein is involved in assembly, spatial organisation, stabilisation and behaviour of microtubules. Under physiological conditions the protein appears in six isoforms in healthy human brains. However in AD, tau protein is known to undergo a number of different post-translational modifications (hyperphosphorylation, ubiquitination, glycosylation). The recent discovery of cosegregation of specific mutations in the tau gene with the disease frontotemporal dementia with Parkinsonism linked to chromosome 17 (FTDP-17) has confirmed that certain abnormalities in the tau protein can be a primary cause of neurodegeneration and dementia in affected individuals (9,10). The molecular events leading to tau modification and paired helical filament (PHF) formation in Alzheimer's disease are unknown. This explains the observation of a broad spectrum of pathophysiological events such as pathological redistribution of tau protein, failure of axonal transport or a failure to maintain axonal microtubule function (11, 12, 13). To date the significance of PHF fibril formation in Alzheimer's disease is questioned in the light of the recent discovery that any protein can form fibrils in vitro (14).

Many authors believe that formation of paired helical fibrils in Alzheimer's disease represents a primary event in neurofibrillary pathology which is based on abnormal phosphorylation. PHF assembled tau protein reacts with certain antibodies in a phosphorylation dependent manner, suggesting a special phosphorylation status (15,16). Furthermore it has been observed that PHF derived tau protein shows a reduced electrophoretic mobility in SDS gels which may be related to its phosphorylation pattern (Steiner et al., EMBO J. 9 (1990), 3539-3544). Similarly it has been suggested that due to phosphorylation, PHF derived tau has lower affinity for microtubules compared to normal tau protein, since a similar effect was found when normal tau was phosphorylated in vitro by certain kinases (17,18). tau is one of the most soluble proteins known (19, 20, 21) and therefor its aggregation in Alzheimer's disease is particularly enigmatic. On the other side the mechanisms by which tau protein is modified in a manner which leads to filament formation in Alzheimer's disease are unknown. Phosphorylation of tau affects the potential of tau to form aggregates, producing either stimulatory or inhibitory effects on microtubule polymerisation, presumably depending on the site of phosphorylation (22-27). Many in vitro studies demonstrate that in the presence of the reducing agent dithiothreitol (DTT), unsaturated free fatty acids, RNA or glycosaminoglycans, normal tau can be transformed into filaments (28-31,38). Furthermore, the process of filament formation can also be accelerated by the presence of cross-linked tau generated through oxidation at Cys322 (32). The parameters that varied in different filament assembly studies including tau protein concentration, pH and ionic strength were manifold higher than in the cytoplasm under physiological conditions. Examination of in vitro formed tau filaments by scanning transmission electron microscopy (STEM) showed, that these filaments differ from native paired helical filaments (33). In the absence of glycans or RNA, no PHF-like filaments are detectable in samples containing unphosphorylated or phosphorylated wild type tau. Moreover it has been suggested that phosphorylation could play a protective role in Alzheimer's disease (34). Similar suggestions for modification of tau leading to assembly of PHF with resulting microtubule disassembly and interference with vital neuronal processes, such as axonal transport, were made for ubiquitination and glycosylation (30, 35, 36, 37). However none of above mentioned post-translational modifications alone could provide molecular explanation for the initiation of tau changes leading to its malfunction that correlate with clinical expression in Alzheimer's disease.

Therefore it remains unclear which of above mentioned modifications of tau are involved in the pathogenesis of Alzheimer's disease.

To date no reliable data on the mode or regulation of post-translational events leading to the formation of early tau protein complexes are available. For the prevention of the formation of such complexes and for neutralisation of any associated pathogenic effects thereof, the precise molecular nature of diseased tau and the regulatory mechanism trans-forming normal tau to its N- and C-terminally double truncated forms need to be clarified. This detailed knowledge would allow to construct tools for Alzheimer therapeutics and diagnostics.

Zelman et al. (J.P. Neurochem. 72(2) (1999), 741-750) suggest that the cleavage product of microtubule binding protein tau occurs in cerebrospinal fluid of persons with traumatic brain injury and reflects damage of neurons. A connection with Alzheimer's disease, however, is not made in this report.

Novak (Acta Virologica 38 (1994), 173-189) reports in this review article concerning "Tauons" the minimal protease resistant unit of PHFs ("paired helical filaments") produced artificially with broad spectrum protease "Pronase".

Kontsekova et al. (J. Immunol. Meth. 185 (1995), 245-248) disclose a quick purification method of recombinant human truncated tau proteins for immunoanalysis in which heat resistancy of human tau protein is used. Neither structural nor biological properties or functions of recombinant tau analoga used therein have been described.

In Novak et al. (EMBO J. 12(1) (1993), 365-370) paired helical filaments (PHF core) have been prepared in vitro artificially, wherein a minimal protease resistant tau unit was recovered by in vitro digestion with the protease pronase. Monoclonal antibody MN423 was used to detect the minimal protease resistant tau unit. The tau polypeptides described in this article, however, do not have biological structural pathological properties common with "real world" tau proteins, especially tau proteins being connected with Alzheimer's disease.

Fasulo et al. (Alzheimer's Research 2(5) (1996), 195-200) report that over-expression of recombinant analogue of PHF core tau is not sufficient to induce tau aggregation and assembly thereof in paired helical filaments. These data are in contrast to a publication of Abraha et al. (J. Cell. Science (113) (21) (2000), 3737-3745) obviously due to the unusual non-physiological assay system described in this publication (cell lines from monkey kidneys).

Fasulo et al (J. Neurochem. 75 (2000), 624-633) describe tau fragments which induce apoptosis. However, none of the Alzheimer's disease related tau proteins described in the present invention can induce apoptosis.

Esposito et al. (J. Peptide Science 6 (2000), 550-559) describe the C terminal 19 amino acids of tau protein and normal healthy tau protein. The articles of Novak et al. (Chem. Papers 52 (1998), 429-430) and Ugolini et al. (Neuro Report 8 (1997) 3709-3712) also relates to the C terminal truncated tau protein also with respect to apoptosis. More recent publications show that Alzheimer's disease is not related to apoptosis processes.

In Abraha et al. (J. Cell Science 113 (21) (2000), 3737-3745) in vitro experiments are described in order to show the contribution of single domains of tau protein for formation of filaments. Therefore a set of recombinant tau molecules have been assembled which have been produced in vitro. Neither biological nor pathological activities of these proteins in bacteria have been generated or determined. Moreover, no data with respect to tau proteins derived from brains from Alzheimer's disease patients have been described in this article.

In Jicha et al. (J. Neuroscience Research 55 (1999), 713-723) a molecular analysis of the epitope of the monoclonal antibodies Alz50 and MC-1 is described. Both antibodies depend on a functional N-terminus of tau molecule, especially amino acid positions 7-9. Tau truncations are not mentioned in this document.

Brandt et al. (J. Biol. Chem. 268 (1993), 3414-3419) have analysed different domains of normal healthy human tau proteins. For this, recombinant tau fragments have been produced in bacteria. Alzheimer related truncated tau fragments, however, are not described in this document.

Philippe et al. (J. Neuroscience Research 46 (1996), 709-719) disclose monoclonal anti amyloid precursor protein antibodies. The authors describe the generation of a tau reactive antibody, although this antibody originally was raised against amyloid precursor protein. Pathology related Alzheimer tau fragments are not disclosed in this document.

WO 94/18560 A1 discloses an immuno assay for detecting human tau protein in a cerebrospinal fluid for detecting patients with cell central nervous cytopathies. This assay does not discriminate between normal tau and tau of patients with central nervous cytopathis but detects the total amount of tau protein in a sample.

It is therefore an object of the present invention to provide such reliable markers correlated with pathological dysfunction of Alzheimer's disease neurons. Moreover, suitable tools for verifying the presence and assaying the activity of such tau derived polypeptides would be valuable means for Alzheimer diagnostics and therapeutics.

The present invention therefore provides N- and C-terminally double truncated tau molecules, which are characterized by the following features ("type IA tau molecules"):
the molecules have at least the first 236 N-terminal amino acids and at least the last 45 C-terminal amino acids of the 4 repeat containing tau43 truncated,
the molecules are detectable in Alzheimer's diseased brain tissue whereas the molecules are not detectable in normal healthy brain tissue and
the molecules prevent normal tau protein from promoting microtubule assembly in an in vitro microtubule assembly assay,
said prevention of the promotion of microtubule assembly can be eliminated by specific inhibitory, neutralising monoclonal antibodies against said molecules in a microtubule assembly assay.

In the following the designation 'N- and C-terminally double truncated tau proteins' is used to describe two groups of truncated tau derivatives which appear in Alzheimer's disease brains and which are closely correlated with pathological dysfunction of Alzheimer's disease neurons. In particular, these proteins represent a group of molecules which exert their pathological function by modifying microtubule associated biological functions such as microtubule assembly or intracellular transport.

In the following the term 'protein complexes' is used for N- and C-terminally double truncated tau proteins in the form of homo-dimeric, heterodimeric or multimeric complexes that are composed of molecules that are physically associated with tau and/or double truncated tau proteins.

As used herein, the term 'tau' refers to the group of shortest naturally occurring isoforms present in healthy human brain containing three repeats (tau44) and four repeats (tau43) in their microtubule binding domain as previously described (39, 40):
tau43 (383 amino acids, missing exons 2 and 3 [pos 45-102])
tau44 (352 amino acids, missing exons 2, 3 and 10 [pos 45-102 and 275-307, resp.]). In the following text the term "wild type tau" is used synonymously for "normal tau protein" and refers to tau protein derived from healthy brains.

Suitable microtubule assembly assays (alternatively often also termed "microtubule polymerisation assays") are e.g. described in (19) and (20). The term "preventing" includes any significant inhibition of 20% or more, preferably 50% or more of normal tau promoting activity.

Specifically preferred type IA tau molecules according to the present invention comprise an amino acid sequence selected from the group of SEQ ID NOs 1 to 3.

Further, the present invention provides N- and C-terminally double truncated tau molecules, which are characterized by the following features ("type IB tau molecules"):
  the molecules have at least the first 238 N-terminal amino acids and at least the last 40 C-terminal amino acids of the 4 repeat containing tau43 or the first 207 N-terminal amino acids and at least the last 50 C-terminal amino acids of the 3 repeat containing tau44 truncated,
  the molecules are detectable in Alzheimer's diseased brain tissue whereas the molecules are not detectable in normal healthy brain tissue and
  the molecules do not prevent wild type tau from promoting microtubule assembly in an in vitro microtubule assembly assay.

Preferred type IB tau molecules are characterized in that the comprise an amino acid sequence selected from the group of SEQ ID NOs 4 to 10.

The present invention also provides N- and C-terminally double truncated tau molecules, which are characterized by the following features ("type IIA tau molecules"):
  the molecules have at least the first 68 N-terminal amino acids and at least the last 40 C-terminal amino acids of the 4 repeat containing tau43 or the first 68 N-terminal amino acids and at least the last 20 C-terminal amino acids of the 3 repeat containing tau44 truncated,
  the molecules are detectable in Alzheimer's diseased brain tissue, whereas the molecules are not detectable in normal healthy brain tissue,
  the molecules have a higher microtubule assembly promoting activity than wild type tau in an in vitro microtubule assembly assay,
  said microtubule assembly promoting activity can be eliminated by specific inhibitory, neutralising monoclonal antibodies against said molecules in a microtubule assembly assay and
  the pathologic activity of said molecules relies their binding to the microtubular network defined by the microtubule polymerisation promoting activity.

Preferably, the enhanced microtubule assembly promoting activity is at least 20% higher, especially at least 50% higher than wild type tau when measured spectrophotometrically.

Preferred type IIA tau molecules are characterized in that the comprise an amino acid sequence selected from the group of SEQ ID NOs 11 to 18.

Moreover, the present invention provides N- and C-terminally double truncated tau molecules, which are characterized by the following features ("type IIB tau molecules"):
  the molecules have at least the first 68 N-terminal amino acids and at least the last 40 C-terminal amino acids of the 4 repeat containing tau43 or the first 68 N-terminal amino acids and at least the last 20 C-terminal amino acids of the 3 repeat containing tau44 truncated,
  the molecules are detectable in Alzheimer's diseased brain tissue, whereas the molecules are not detectable in normal healthy brain tissue,
  the molecules have a pathological microtubule assembly promoting activity different from wild type tau in an in vitro microtubule assembly assay.

Preferred type IIB tau molecules according to the present invention are characterized in that they comprise an amino acid sequence selected from the group of SEQ ID NOs 19 and 20.

The novel tau polypeptides according to the present invention (IA, IB, IIA and IIB) have typical and unique localisation characteristics since they exclusively localize in Alzheimer's diseased brain tissue. Moreover, also the interaction of these polypeptides with non-polymerized tubulin (alpha/beta dimers) and polymerized form (as microtubule) is unique.

According to another aspect, the present invention provides a method for the preparation of molecules according to the present invention (type IA, IB, IIA, IIB), characterized in by the following steps:
  a) construction of a recombinant prokaryotic expression plasmids carrying coding sequences for a double truncated tau molecule with deletions covering at least the first 236 and the last 40 amino acids or the first 68 and the last 20 amino acids or combinations thereof,
  b) growing said bacteria under conditions allowing expression of said N- and C-terminally double truncated tau molecule,
  c) collecting of bacteria, preferably by centrifugation,
  d) resuspending the bacterial pellet,
  e) sonicating said bacteria,
  f) fractionating said sonicated bacteria by gel filtration and
  g) monitoring the activity of the obtained fractions by a microtubule assembly assay thereby identifying the different activities of type I and type II tau molecules.

Preferably, the truncations are as defined above for type IA, IB, IIA and IIB molecules. The microtubule assembly assay activity is preferably as defined above, especially as for IA.

Moreover the present invention provides a method for the preparation of molecules according to the present invention, characterized in by the following steps:
  a) providing Alzheimer's diseased brain tissue,
  b) homogenising said diseased brain tissue in a buffer, especially in Tris buffer,
  c) ammonium sulfate precipitation of said homogenized brain tissue,
  d) redissolving in PIPES buffer,
  e) fractionating said redissolved material by gel filtration and
  f) monitoring the activity of the obtained fractions by a microtubule assembly assay thereby identifying the different activities of type I and type II tau molecules.

The microtubule assembly assay activity is preferably as defined above, especially as for IA.

The present invention further provides a method for testing substances effective in disassembling a complex of type IA molecules and tubulin, comprising the following steps:
  a) allowing the formation of protein complexes between type IA molecules and tubulin and
  b) incubating the protein complexes with a substance to be tested and identifying those substances which allow the restoration of the microtubule assembly promoting capacity of wild type tau.

Further, the present invention also provides a method for testing substances effective in inhibiting type IA molecules from initiating the formation of complexes with tubulin in a cellular system expressing wild type tau comprising the following steps:

a) introducing a functional gene encoding a type IA molecule under the control of suitable regulatory regions into a cell expressing normal tau protein,
b) allowing the formation of protein complexes between type IA molecules and tubulin molecules,
c) applying the substance to be tested to the cells harboring said complexes an
d) examining the effect of said substance on type IA biological activity as defined above.

The present invention also provides a method for in vitro conversion of microtubules into a pathological state characterized by incubating tubulin protein with type IIA under physiological conditions which allow the interaction of said type IIA molecules with microtubules generating pathological microtubules.

According to another aspect, the present invention provides a method for screening substances capable of neutralising the pathological effects of a type IIA molecules for their property to eliminate and/or neutralize type IIA molecules and to restore physiological microtubule parameters and functions caused by type II molecules comprising the following steps:
a) formation of pathological microtubules in the presence of type IIA molecules and tubulin,
b) incubation of a mixture of the substance, type IIA and tubulin with the substance to be screened and
c) examination of the result with respect to diminishing the formation of pathological microtubules caused by type IIA molecules.

According to the present invention, also a method for testing substances effective in inhibiting the in vivo activity of type IIA molecules in promoting abnormal microtubule formation and function in a cellular system expressing type IIA molecules is provided, which comprises the following steps:
a) introducing a functional gene encoding type IIA molecules under the control of suitable regulatory regions into a cell expressing wild type tau,
b) allowing the formation of complexes between type IIA tau molecules and microtubules, whereby said complexes are involved in the formation of pathological microtubules,
c) applying the substance to be tested to the cells harboring said complexes and
d) examining the effect of said substance on type IIA biological activity, especially on the modifications of the microtubule network and its associated functions.

According to another aspect, the present invention also provides transgenic animals expressing a molecule according to the present invention (type IA, IB, IIA or IIB), especially IA an/or IIA.

The present invention also relates to the use of a transgenic animal according to the present invention as animal model for Alzheimer's disease, especially for screening and testing drugs for the treatment of Alzheimer's disease.

With the present invention a vaccine is provided which comprises a molecule according to the present invention (IA, IB, IIA or IIB), especially IA and IIA, and a pharmaceutically acceptable carrier, especially an adjuvant.

The present invention also provides inhibitor of the initiation of the formation of complexes of a type IA molecule with wild type tau. A specific example for such inhibitors are substances comprising a binding moiety as the monoclonal antibody DC44 deposited under the deposition number 02060767 at the European Collection of Cell Cultures (ECACC), Porton Down, Salisbury, UK, especially DC44 or binding fragments thereof, such as the Fab.

Thus, the present invention provides:
(1) molecular and functional identification and characterisation of N- and C-terminally truncated diseased forms of tau proteins. These molecules exert their pathological function in Alzheimer's disease by modifying microtubule associated biological functions such as microtubule assembly or intracellular transport.
(2) antibodies specific for the protein epitopes
(3) antibodies neutralising pathological activities of said proteins
(4) methods for screening and testing therapeutic drug candidates (including antibodies) effective in inhibiting, neutralising and eliminating N- and C-terminally double truncated tau proteins or preventing formation thereof
(5) the development of animal models bearing gene constructs encoding for the respective double truncated tau proteins as transgene or transgene-combinations which can be used for drug screening
(6) pharmaceutical compositions comprising inhibitors to said double truncated tau proteins and to proteases involved in their origin
(7) methods for screening molecules which generate N- and C-terminally double truncated tau molecules
(8) diagnostic and therapeutic compositions recognising and/or interacting with said molecules
(9) the development of vaccines based on the antigenicity of said double truncated proteins
(10) methods involving said proteins and their epitopes and/or antibodies or other specific probes for in vitro and in vivo diagnosis of Alzheimer's disease and other disorders related to pathological changes of tau.

Accordingly, the present invention relates to the characterisation of N- and C-terminally double truncated forms of pathological tau protein and their epitopes which are specifically occurring in Alzheimer's disease.

Degradation of proteins is a general phenomenon occurring during physiological elimination of proteins encompassing production of intermediate truncation products of various size, usually of short half life. at protein is no exception and undergoes this process in healthy brains containing wt (=wild type) tau. In the following the term 'wt at covers all 6 naturally occurring isoforms of tau protein normally found in the brain of healthy individuals. Various short truncation forms of at found in Alzheimer diseased brain were produced in bacteria, purified to various extent with aim to probe physiological function of at proteins, to map their domains and phosphorylation epitopes or in experiments trying to understand the mechanisms of paired helical assembly in Alzheimer's disease and other neurodegenerative disorders, with equivocal results (23-27, 34, 41, 42). The general term "N- and C-terminally double truncated forms of tau proteins" refers to any tau protein in Alzheimer's disease with loss at least one of its amino acids at both ends of molecule. Throughout the analysis of double truncated tau in extracts from Alzheimer diseased brains it was found in the course of the present invention that some of these molecules displayed structurally and functionally distinct characteristics which allowed to discriminate them from other tau fragments found in Alzheimer's diseased brain tissue. On the basis of this discrimination a novel scheme was provided which defines two major classes of pathogenic molecules of N- and C-terminally double truncated tau molecules distinct from healthy tau: Type I and Type II tau molecules. These groups can further be subdivided into two subclasses each based on the molecular structure and are designated type IA and B, and type IIA and B, respectively.

Type IA and type IIA represent structurally and functionally distinct types of diseased molecules derived from microtubule associated protein tau generated by pathological processing. N- and C-terminally truncated tau molecules, represent diseased molecules, derived from microtubule associated protein tau and emerging during specific pathological processes characteristic of Alzheimer's disease. This is a common feature of all four groups of tau derived proteins. Further common features of all groups are an N- and C-terminal truncations, their intra- and extraneuronal localisation and functional distinction from normal, healthy tau.

The group of molecules designated 'type IA' is described by the examples SEQ ID 1-3. These truncated tau molecules differ from normal tau in acting as key (central), active units, and driving force for interaction of pathological tau and tubulin. Type IA as well as type IB molecules do not have any promoting activity in microtubule assembly. Surprisingly type IA is able to prevent normal tau from promoting microtubule assembly (Example 1). Despite of similar primary sequence features and molecular masses, type IB, does not show this functional activity in vitro (Example 2). This is suggestive for a strong binding activity of type IA to tubulin and thereby providing a dominant negative effect on tau physiology. Type IA molecules are therefore most likely responsible for continuous, chronic depletion of neurons from functional microtubular network and for taking part in neurofibrillary structures which directly correlate with the clinical severeness of Alzheimer's disease. Unexpectedly, type IB (e.g. SEQ. ID. NO: 4-10), despite having similar molecular mass and sequences as the type IA group of molecules, display none of pathological activities of group IA members (see Example 2). As opposed to these groups, type IIA double truncated tau derivatives bind microtubules and promote their pathological assembly (Example 3). In the following Type IIA promoted microtubules are referred to as 'pathological microtubules'. Surprisingly molecules with similar sequences and ranges of molecular weights (Type IIB) are lacking these high microtubule polymerisation capabilities. In microtubule assembly assays they perform to the levels seen with full length tau protein (see Example 3).

N- and C-terminally truncated tau derivatives of both groups (type IIA and B) interfere at the cellular level with axonal transport leading to synaptic loss which ultimately results in neuronal dysfunction and cognitive impairment in Alzheimer's disease patients. Simultaneously, afflicted neurons are vulnerable to various forms of stress such as oxidative stress (Example 4). Type IIB despite of having similar molecular sizes than type IIA additionally promote microtubule assembly to levels seen for full length healthy tau (wild type tau) when measured spectrophotometrically.

In a further preferred embodiment of the type IA and -B and type IIA and B molecules of the invention the recombinant versions of said molecules can be obtained by carrying out the following steps:

(a) Construction of a recombinant prokaryotic expression plasmids carrying coding sequences for said double truncated tau molecules (type I and II)
(b) growth of bacteria under conditions allowing expression an N- and C-terminally double truncated tau molecules (type I and II)
(c) collecting of bacteria by centrifugation
(d) resuspending the bacterial pellet from 500 ml cultivation in buffer A: (20 mM PIPES pH 6.9, 50 mM NaCl, 1 mM EGTA, 1 mM MgSO$_4$, 2 mM DTT, 0.1 mM PMSF)
(e) sonication on ice for 1 min (3 times) centrifugation at 45 000 rpm, 15 min at +2° C. (rotor TLA-120,2, Beckmann Optima TLX)
(f) chromatography on Phosphocellulose, or MONO S HR 5/5 or 5 ml HiTrap SP Sepharose HP column in linear gradient 0-1M NaCl in buffer "A" identifying the obtained proteins by SDS-PAGE and Western blot analysis.

In a preferred embodiment of the invention, said type IA group of N- and C-terminally double truncated members comprises the following amino acid sequences:

```
Derivatives from four repeat tau (tau 43) will be
labeled R4
(239-333, R4)
                                         SEQ ID NO: 1
ile lys his val pro gly gly gly ser val gln ile
val tyr lys pro val asp leu ser lys val thr ser
lys cys gly ser leu gly asn ile his his lys pro
gly gly gly gln val glu val lys ser glu lys leu
asp phe lys asp arg val gln ser lys ile gly ser
leu asp asn ile thr his val pro gly gly gly asn
lys lys ile glu thr his lys leu thr phe arg glu
asn ala lys ala lys thr asp his gly ala glu (237-333, R4)
                                         SEQ ID NO: 2
asp asn ile lys his val pro gly gly gly ser val
gln ile val tyr lys pro val asp leu ser lys val
thr ser lys cys gly ser leu gly asn ile his his
lys pro gly gly gly gln val glu val lys ser glu
lys leu asp phe lys asp arg val gln ser lys ile
gly ser leu asp asn ile thr his val pro gly gly
gly asn lys lys ile glu thr his lys leu thr phe
arg glu asn ala lys ala lys thr asp his gly ala
glu (239-318, R4)
                                         SEQ ID NO: 3
ile lys his val pro gly gly gly ser val gln ile
val tyr lys pro val asp leu ser lys val thr ser
lys cys gly ser leu gly asn ile his his lys pro
gly gly gly gln val glu val lys ser glu lys leu
asp phe lys asp arg val gln ser lys ile gly ser
leu asp asn ile thr his val pro gly gly gly asn
lys lys ile glu thr his lys leu
```

In a preferred embodiment of the invention, said type IB group of N- and C-terminally double truncated members comprises the following amino acid sequences:

```
(239-326, R4)
                                         SEQ ID NO: 4
ile lys his val pro gly gly gly ser val gln ile
val tyr lys pro val asp leu ser lys val thr ser
lys cys gly ser leu gly asn ile his his lys pro
gly gly gly gln val glu val lys ser glu lys leu
asp phe lys asp arg val gln ser lys ile gly ser
leu asp asn ile thr his val pro gly gly gly asn
lys lys ile glu thr his lys leu thr phe arg glu
asn ala lys ala (239-328, R4)
                                         SEQ ID NO: 5
ile lys his val pro gly gly gly ser val gln ile
val tyr lys pro val asp leu ser lys val thr ser
lys cys gly ser leu gly asn ile his his lys pro
gly gly gly gln val glu val lys ser glu lys leu
asp phe lys asp arg val gln ser lys ile gly ser
leu asp asn ile thr his val pro gly gly gly asn
lys lys ile glu thr his lys leu thr phe arg glu
asn ala lys ala lys thr
```

```
(239-331, R4)
                                                 SEQ ID NO: 6
ile lys his val pro gly gly gly ser val gln ile
val tyr lys pro val asp leu ser lys val thr ser
lys cys gly ser leu gly asn ile his his lys pro
gly gly gly gln val glu val lys ser glu lys leu
asp phe lys asp arg val gln ser lys ile gly ser
leu asp asn ile thr his val pro gly gly gly asn
lys lys ile glu thr his lys leu thr phe arg glu
asn ala lys ala lys thr asp his gly (239-334, R4)
                                                 SEQ ID NO: 7
ile lys his val pro gly gly gly ser val gln ile
val tyr lys pro val asp leu ser lys val thr ser
lys cys gly ser leu gly asn ile his his lys pro
gly gly gly gln val glu val lys ser glu lys leu
asp phe lys asp arg val gln ser lys ile gly ser
leu asp asn ile thr his val pro gly gly gly asn
lys lys ile glu thr his lys leu thr phe arg glu
asn ala lys ala lys thr asp his gly ala glu ile (239-340, R4)
                                                 SEQ ID NO: 8
ile lys his val pro gly gly gly ser val gln ile
val tyr lys pro val asp leu ser lys val thr ser
lys cys gly ser leu gly asn ile his his lys pro
gly gly gly gln val glu val lys ser glu lys leu
asp phe lys asp arg val gln ser lys ile gly ser
leu asp asn ile thr his val pro gly gly gly asn
lys lys ile glu thr his lys leu thr phe arg glu
asn ala lys ala lys thr asp his gly ala glu ile
val tyr lys ser pro val (239-343, R4)
                                                 SEQ ID NO: 9
ile lys his val pro gly gly gly ser val gln ile
val tyr lys pro val asp leu ser lys val thr ser
lys cys gly ser leu gly asn ile his his lys pro
gly gly gly gln val glu val lys ser glu lys leu
asp phe lys asp arg val gln ser lys ile gly ser
leu asp asn ile thr his val pro gly gly gly asn
lys lys ile glu thr his lys leu thr phe arg glu
asn ala lys ala lys thr asp his gly ala glu ile
val tyr lys ser pro val val ser gly Derivatives from three repeat tau (tau 44) will be
labeled R3
(208-302, R3)
                                                 SEQ ID NO: 10
leu lys his gln pro gly gly gly lys val gln ile
val tyr lys pro val asp leu ser lys val thr ser
lys cys gly ser leu gly asn ile his his lys pro
gly gly gly gln val glu val lys ser glu lys leu
asp phe lys asp arg val gln ser lys ile gly ser
leu asp asn ile thr his val pro gly gly gly asn
lys lys ile glu thr his lys leu thr phe arg glu
asn ala lys ala lys thr asp his gly ala glu
```

There may be one or more epitopes of tau protein which specifically occur in type IA or type IIA members in N- and C-terminally double truncated diseased forms of tau proteins.

In the present embodiment of the invention, said epitopes are specifically located within the primary structure of type IA (SEQ ID 1-3) and type IIA (SEQ ID 11-18) group members and their number, heterogeneity and specificity depends on and is added by specific structural conformation of each individual group member. Therefore the singularity of each molecule is not solely based on its primary structure together with its effects on microtubule assembly, but also on its secondary and ternary structure which makes up its epitopes. Some of them can form particularly important "conformational regions" contributing significantly to the activity of said molecules.

The term "conformational region" as used herein refers to epitopes clustered to one region of molecule contributing to its activity.

In a particularly preferred embodiment the conformational region encompassed in type I and type II molecules comprising amino acids "ile lys his val pro gly gly gly ser val gln ile val tyr lys pro val asp leu ser lys val thr ser lys cys gly ser leu" is corresponding to residues 239-267 (SEQ ID NO: 1-9 and 11-14, 19 R4) and comprising amino acids "val gln ile val tyr lys pro val asp leu ser lys val thr ser lys cys gly ser leu" corresponding to residues 217-236 (SEQ ID NO: 10.15-18, 20 R3) was designated sequence A.

In still another preferred embodiment of the invention said epitopes in said conformational region were identified and their relative contribution determined by deletion mutagenesis. The significance of all these epitopes and their relationship to function on microtubules are demonstrated by the mutant forms which showed that they are contributing at various extent to the activity of type IA molecules (Example 5). These individual epitopes comprise the following amino acid sequences:

```
A: ile lys his val pro gly gly gly ser val gln ile
val tyr lys pro val asp leu ser lys val thr ser
lys cys gly ser leu
(corresponding to residues 239-267 in SEQ ID NO:
1-9 and 11-14, 19). The epitope deletion mutant
has SEQ ID NO: 21 (268-333, R4; del 239-267)
gly asn ile his his lys pro gly gly gly gln val
glu val lys ser glu lys leu asp phe lys asp arg
val gln ser lys ile gly ser leu asp asn ile thr
his val pro gly gly gly asn lys lys ile glu thr
his lys leu thr phe arg glu asn ala lys ala lys
thr asp his gly ala glu A1: ile lys his val pro gly gly gly ser
(corresponding to residues 239-247 in SEQ ID NO:
1-9 and 11-14, 19). The deletion mutant has SEQ ID
NO: 22 (248-333, R4; del 239-247)
val gln ile val tyr lys pro val asp leu ser lys
val thr ser lys cys gly ser leu gly asn ile his
his lys pro gly gly gly gln val glu val lys ser
glu lys leu asp phe lys asp arg val gln ser lys
ile gly ser leu asp asn ile thr his val pro gly
gly gly asn lys lys ile glu thr his lys leu thr
phe arg glu asn ala lys ala lys thr asp his gly
ala glu A2: ile lys his val pro gly gly gly ser val gln
ile val tyr lys pro val asp leu
(corresponding to residues 239-257 in SEQ ID NO:
1-9 and 11-14, 19). The deletion mutant has SEQ ID
NO: 23 (258-333, R4; del 239-257)
ser lys val thr ser lys cys gly ser leu gly asn
ile his his lys pro gly gly gly gln val glu val
lys ser glu lys leu asp phe lys asp arg val gln
ser lys ile gly ser leu asp asn ile thr his val
pro gly gly gly asn lys lys ile glu thr his lys
leu thr phe arg glu asn ala lys ala lys thr asp
his gly ala glu A3: ile lys his val pro gly gly gly ser val gln
ile val tyr lys pro val asp leu ser lys val thr
ser
(corresponding to residues 239-262 in SEQ ID NO:
1-9 and 11-14, 19). The deletion mutant has SEQ ID
NO: 24 (263-333, R4; del 239-262)
lys cys gly ser leu gly asn ile his his lys pro
gly gly gly gln val glu val lys ser glu lys leu
asp phe lys asp arg val gln ser lys ile gly ser
leu asp asn ile thr his val pro gly gly gly asn
lys lys ile glu thr his lys leu thr phe arg glu
asn ala lys ala lys thr asp his gly ala glu
```

-continued

A4: ser val gln ile val tyr lys pro val asp leu
ser lys val thr ser
(corresponding to residues 246-262 in SEQ ID NO:
1-9 and 11-14, 19). The epitope deletion mutant
has SEQ ID NO: 25 (239-333, R4;

of synthetic surfaces of phages or bacteria or ribosomes (ribosomal display) and similar technologies known in the art.

A further object of the invention is to provide a method for testing molecules and compounds effective in disassembling type IA complexes (type I in vitro assay) comprising the following steps:
a) allowing the formation of protein complexes between type IA molecules or peptides derived thereof and tubulin or other molecules interacting with type IA molecules
b) incubating the protein complexes with drug to be tested
c) examining the result of the incubation of step (b) with respect to the restoration of the microtubule assembly promoting capacity of the healthy tau isoforms.

Still another object of the invention is to provide a method for testing drugs effective in the prevention or reduction of the inhibition of normal in vitro activity of healthy tau isoforms comprising the following steps:
a) A given drug to be tested in combination with type IA molecules or peptides derived thereof is expected not to interfere with normal tau and its in vitro functions.
b) Incubation of a type IA molecule with a drug to be tested in the presence of normal tau and tubulin
c) Examining the result of the incubation of step a) and b) with respect to the presence or absence of inhibiting activity of type IA molecules on microtubule polymerisation (Example 8).

The term "allowing the formation of complexes between type IA molecules or peptides derived thereof and tubulin" in the absence of said drug refers to condition which allows interaction of type IA molecule with said tubulin resulting in inhibition of microtubule formation.

The person skilled in the art knows how to employ the method of the present invention for a variety of different purposes which all fall under the scope of protection of the present invention.

In a further aspect, the present invention relates to a method for testing drugs effective in inhibiting type IA molecules from initiating the formation of complexes in a cellular system expressing tau or tau derived proteins (type I cellular assay) comprising the following steps:
a) introducing a functional gene encoding type IA molecules under the control of suitable regulatory regions into a cell expressing normal tau protein
b) allowing the formation of protein complexes between type IA tau and tubulin molecules
c) applying the drug to be tested to the cells harboring said complexes
d) examining the effect of said drug on type IA biological activity such as structural and functional modifications of microtubules.

The term 'cell expressing tau protein' as used in step (a), refers to cells which have the capacity to express N- and C-terminally double truncated tau forms from a gene construct encoding a type IA molecule or a derivative thereof. The person skilled in the art is aware of the fact that the sequence of experimental steps of the introduction of the genes encoding the type IA molecules is irrelevant for the purpose of the method of the invention.

Said method is particularly advantageous since the screening system is based on the continuously growing cell lines which provide a close image of the in vivo situation. Moreover, ample supply of type IA molecules located intracellularly allows screening for drugs effective in inhibiting the biological effects of type IA molecules.

In a preferred embodiment said cell expressing type IA molecules is a neuroblastoma, or pheochromocytoma cell or a primary culture of nerve cells derived from transgenic animal expressing type IA molecules.

The group of molecules designated 'type II' consists of N- an C-terminally double truncated tau protein molecules (e.g. sequences described in SEQ ID 11-20). Representatives of this group localize intra- and extraneuronally and are functionally different from normal, healthy tau.

The discovery and isolation of this group of proteins underlying the present invention provides (1) a molecular description and characterisation of tau modifications leading to specific microtubule binding and abnormal promotion of microtubule assembly (Example 3) with pathological consequences to its carrier (Example 4), (2) antibodies specific for the protein epitopes and (3) antibodies neutralising pathological activities of said type II molecules (Example 12), (4) methods for screening and testing therapeutic drug candidates effective in inhibiting, neutralising and eliminating said type II proteins or (5) methods screening and testing therapeutic drug candidates effective in inhibiting formation of tau derived proteins such as type II molecules, (6) the development of animal models bearing gene constructs encoding for the respective N- and C-terminally double truncated tau proteins as a transgene or transgene-combinations which can be used for drug screening (7) pharmaceutical compositions comprising inhibitors to said double truncated tau proteins and their proteases, (8) diagnostic and therapeutic compositions recognising/interacting with said molecules, (9) the development of vaccines based on said double truncated proteins (10) methods involving said proteins and their epitopes and/or antibodies or other specific probes for in vitro and in vivo diagnosis of Alzheimer's disease and other disorders related to pathological changes of tau.

As opposed to the groups type IA and B, type IIA molecules promote pathological microtubule assembly significantly higher than microtubule assembly promoted by normal healthy tau isoforms when measured spectrophotometrically (see Examples 1 and 3, resp.). Surprisingly a subgroup of N- and C-terminally double truncated tau molecules with similar sequences and ranges of molecular weights (type IIB) are lacking these "high" microtubule polymerisation capabilities. In microtubule assembly assays, this subgroup of molecules performs to the levels seen with full length tau protein (Example 3).

Accordingly, the present invention relates to a new type of modified tau protein found in Alzheimer's disease, called type IIA group of tau proteins. The group consist of N- and C-terminally double truncated tau molecules (SEQ ID 11-18).

The term type II molecules refers to members of the group significantly different in structure and function not only from normal healthy tau but from type IA and -B tau group as well. Molecules of this subgroup bind microtubules and promote their pathological assembly that is significantly more pronounced than normal microtubule assembly by healthy tau isoforms (Example 3). Type IIA N- and C-terminally double truncated tau molecules interfere at the cellular level with axonal transport of constituents leading to synaptic loss and neuronal malfunction ultimately leading to cognitive impairment of the whole organism in Alzheimer's disease neurons and under experimental conditions (Examples 15 and 16, resp.). Simultaneously, afflicted neurons are vulnerable to various forms of stress such as for example oxidative stress (Example 4).

In a preferred embodiment of the invention, said type IIA group of N- and C-terminally double truncated members comprises the amino acid sequences:

Derivatives from four repeat tau (tau 43) are labeled R4

(69-333, R4)

SEQ ID NO: 11 met val ser lys ser lys asp gly thr gly ser asp
asp lys lys ala lys gly ala asp gly lys thr lys
ile ala thr pro arg gly ala ala pro pro gly gln
lys gly gln ala asn ala thr arg ile pro ala lys
thr pro pro ala pro lys thr pro pro ser ser gly
glu pro pro lys ser gly asp arg ser gly tyr ser
ser pro gly ser pro gly thr pro gly ser arg ser
arg thr pro ser leu pro thr pro pro thr arg glu
pro lys lys val ala val val arg thr pro pro lys
ser pro ser ser ala lys ser arg leu gln thr ala
pro val pro met pro asp leu lys asn val lys ser
lys ile gly ser thr glu asn leu lys his gln pro
gly gly gly lys val gln ile ile asn lys lys leu
asp leu ser asn val gln ser lys cys gly ser lys
asp asn ile lys his val pro gly gly gly ser val
gln ile val tyr lys pro val asp leu ser lys val
thr ser lys cys gly ser leu gly asn ile his his
lys pro gly gly gly gln val glu val lys ser glu
lys leu asp phe lys asp arg val gln ser lys ile
gly ser leu asp asn ile thr his val pro gly gly
gly asn lys lys ile glu thr his lys leu thr phe
arg glu asn ala lys ala lys thr asp his gly ala
glu (93-333, R4)

SEQ ID NO: 12 ile ala thr pro arg gly ala ala pro pro gly gln
lys gly gln ala asn ala thr arg ile pro ala lys
thr pro pro ala pro lys thr pro pro ser ser gly
glu pro pro lys ser gly asp arg ser gly tyr ser
ser pro gly ser pro gly thr pro gly ser arg ser
arg thr pro ser leu pro thr pro pro thr arg glu
pro lys lys val ala val val arg thr pro pro lys
ser pro ser ser ala lys ser arg leu gln thr ala
pro val pro met pro asp leu lys asn val lys ser
lys ile gly ser thr glu asn leu lys his gln pro
gly gly gly lys val gln ile ile asn lys lys leu
asp leu ser asn val gln ser lys cys gly ser lys
asp asn ile lys his val pro gly gly gly ser val
gln ile val tyr lys pro val asp leu ser lys val
thr ser lys cys gly ser leu gly asn ile his his
lys pro gly gly gly gln val glu val lys ser glu
lys leu asp phe lys asp arg val gln ser lys ile
gly ser leu asp asn ile thr his val pro gly gly
gly asn lys lys ile glu thr his lys leu thr phe
arg glu asn ala lys ala lys thr asp his gly ala
glu (69-363, R4)

SEQ ID NO: 13 met val ser lys ser lys asp gly thr gly ser asp
asp lys lys ala lys gly ala asp gly lys thr lys
ile ala thr pro arg gly ala ala pro pro gly gln
lys gly gln ala asn ala thr arg ile pro ala lys
thr pro pro ala pro lys thr pro pro ser ser gly
glu pro pro lys ser gly asp arg ser gly tyr ser
ser pro gly ser pro gly thr pro gly ser arg ser
arg thr pro ser leu pro thr pro pro thr arg glu
pro lys lys val ala val val arg thr pro pro lys
ser pro ser ser ala lys ser arg leu gln thr ala
pro val pro met pro asp leu lys asn val lys ser
lys ile gly ser thr glu asn leu lys his gln pro
gly gly gly lys val gln ile ile asn lys lys leu
asp leu ser asn val gln ser lys cys gly ser lys
asp asn ile lys his val pro gly gly gly ser val
gln ile val tyr lys pro val asp leu ser lys val
thr ser lys cys gly ser leu gly asn ile his his
lys pro gly gly gly gln val glu val lys ser glu
lys leu asp phe lys asp arg val gln ser lys ile
gly ser leu asp asn ile thr his val pro gly gly
gly asn lys lys ile glu thr his lys leu thr phe
arg glu asn ala lys ala lys thr asp his gly ala
glu ile val tyr lys ser pro val val ser gly asp
thr ser pro arg his leu ser asn val ser ser thr
gly ser ile asp met val asp (93-363, R4)

SEQ ID NO: 14 ile ala thr pro arg gly ala ala pro pro gly gln
lys gly gln ala asn ala thr arg ile pro ala lys
thr pro pro ala pro lys thr pro pro ser ser gly
glu pro pro lys ser gly asp arg ser gly tyr ser
ser pro gly ser pro gly thr pro gly ser arg ser
arg thr pro ser leu pro thr pro pro thr arg glu
pro lys lys val ala val val arg thr pro pro lys
ser pro ser ser ala lys ser arg leu gln thr ala
pro val pro met pro asp leu lys asn val lys ser
lys ile gly ser thr glu asn leu lys his gln pro
gly gly gly lys val gln ile ile asn lys lys leu
asp leu ser asn val gln ser lys cys gly ser lys
asp asn ile lys his val pro gly gly gly ser val
gln ile val tyr lys pro val asp leu ser lys val
thr ser lys cys gly ser leu gly asn ile his his
lys pro gly gly gly gln val glu val lys ser glu
lys leu asp phe lys asp arg val gln ser lys ile
gly ser leu asp asn ile thr his val pro gly gly
gly asn lys lys ile glu thr his lys leu thr phe
arg glu asn ala lys ala lys thr asp his gly ala
glu ile val tyr lys ser pro val val ser gly asp
thr ser pro arg his leu ser asn val ser ser thr
gly ser ile asp met val asp Derived from three repeat tau (tau 44) are labeled R3

(93-302, R3)

SEQ ID NO: 15 ile ala thr pro arg gly ala ala pro pro gly gln
lys gly gln ala asn ala thr arg ile pro ala lys
thr pro pro ala pro lys thr pro pro ser ser gly
glu pro pro lys ser gly asp arg ser gly tyr ser
ser pro gly ser pro gly thr pro gly ser arg ser
arg thr pro ser leu pro thr pro pro thr arg glu
pro lys lys val ala val val arg thr pro pro lys
ser pro ser ser ala lys ser arg leu gln thr ala
pro val pro met pro asp leu lys asn val lys ser
lys ile gly ser thr glu asn leu lys his gln pro
gly gly gly lys val gln ile val tyr lys pro val
asp leu ser lys val thr ser lys cys gly ser leu
gly asn ile his his lys pro gly gly gly gln val
glu val lys ser glu lys leu asp phe lys asp arg
val gln ser lys ile gly ser leu asp asn ile thr
his val pro gly gly gly asn lys lys ile glu thr
his lys leu thr phe arg glu asn ala lys ala lys
thr asp his gly ala glu (69-302, R3)

SEQ ID NO: 16 met val ser lys ser lys asp gly thr gly ser asp
asp lys lys ala lys gly ala asp gly lys thr lys
ile ala thr pro arg gly ala ala pro pro gly gln
lys gly gln ala asn ala thr arg ile pro ala lys
thr pro pro ala pro lys thr pro pro ser ser gly
glu pro pro lys ser gly asp arg ser gly tyr ser
ser pro gly ser pro gly thr pro gly ser arg ser
arg thr pro ser leu pro thr pro pro thr arg glu
pro lys lys val ala val val arg thr pro pro lys
ser pro ser ser ala lys ser arg leu gln thr ala
pro val pro met pro asp leu lys asn val lys ser
lys ile gly ser thr glu asn leu lys his gln pro
gly gly gly lys val gln ile val tyr lys pro val
asp leu ser lys val thr ser lys cys gly ser leu
gly asn ile his his lys pro gly gly gly gln val
glu val lys ser glu lys leu asp phe lys asp arg
val gln ser lys ile gly ser leu asp asn ile thr
his val pro gly gly gly asn lys lys ile glu thr
his lys leu thr phe arg glu asn ala lys ala lys
thr asp his gly ala glu (93-332, R3)

SEQ ID NO: 17 ile ala thr pro arg gly ala ala pro pro gly gln
lys gly gln ala asn ala thr arg ile pro ala lys
thr pro pro ala pro lys thr pro pro ser ser gly
glu pro pro lys ser gly asp arg ser gly tyr ser
ser pro gly ser pro gly thr pro gly ser arg ser
arg thr pro ser leu pro thr pro pro thr arg glu
pro lys lys val ala val val arg thr pro pro lys -continued ser pro ser ser ala lys ser arg leu gln thr ala
pro val pro met pro asp leu lys asn val lys ser
lys ile gly ser thr glu asn leu lys his gln pro
gly gly gly lys val gln ile val tyr lys pro val
asp leu ser lys val thr ser lys cys gly ser leu
gly asn ile his his lys pro gly gly gly gln val
glu val lys ser glu lys leu asp phe lys asp arg
val gln ser lys ile gly ser leu asp asn ile thr
his val pro gly gly gly asn lys lys ile glu thr
his lys leu thr phe arg glu asn ala lys ala lys
thr asp his gly ala glu ile val tyr lys ser pro
val val ser gly asp thr ser pro arg his leu ser
asn val ser ser thr gly ser ile asp met val asp (69-332, R3)

SEQ ID NO: 18 met val ser lys ser lys asp gly thr gly ser asp
asp lys lys ala lys gly ala asp gly lys thr lys
ile ala thr pro arg gly ala ala pro pro gly gln
lys gly gln ala asn ala thr arg ile pro ala lys
thr pro pro ala pro lys thr pro pro ser ser gly
glu pro pro lys ser gly asp arg ser gly tyr ser
ser pro gly ser pro gly thr pro gly ser arg ser
arg thr pro ser leu pro thr pro pro thr arg glu
pro lys lys val ala val val arg thr pro pro lys
ser pro ser ser ala lys ser arg leu gln thr ala
pro val pro met pro asp leu lys asn val lys ser
lys ile gly ser thr glu asn leu lys his gln pro
gly gly gly lys val gln ile val tyr lys pro val
asp leu ser lys val thr ser lys cys gly ser leu
gly asn ile his his lys pro gly gly gly gln val
glu val lys ser glu lys leu asp phe lys asp arg
val gln ser lys ile gly ser leu asp asn ile thr
his val pro gly gly gly asn lys lys ile glu thr
his lys leu thr phe arg glu asn ala lys ala lys
thr asp his gly ala glu ile val tyr lys ser pro
val val ser gly asp thr ser pro arg his leu ser
asn val ser ser thr gly ser ile asp met val asp In a preferred embodiment of the invention, said type II B group of N- and C-terminally double truncated members comprises the amino acid sequences:

(6-378, R4)

SEQ ID NO: 19 gln glu phe glu val met glu asp his ala gly thr
tyr gly leu gly asp arg lys asp gln gly gly tyr
thr met his gln asp gln glu gly asp thr asp ala
gly leu lys ala glu gln ala gly ile gly asp thr
pro ser leu glu asp glu ala ala gly his val thr
gln ala arg met val ser lys ser lys asp gly thr
gly ser asp asp lys lys ala lys gly ala asp gly
lys thr lys ile ala thr pro arg gly ala ala pro
pro gly gln lys gly gln ala asn ala thr arg ile
pro ala lys thr pro pro ala pro lys thr pro pro
ser ser gly glu pro pro lys ser gly asp arg ser
gly tyr ser ser pro gly ser pro gly thr pro gly
ser arg ser arg thr pro ser leu pro thr pro pro
thr arg glu pro lys lys val ala val val arg thr
pro pro lys ser pro ser ser ala lys ser arg leu
gln thr ala pro val pro met pro asp leu lys asn
val lys ser lys ile gly ser thr glu asn leu lys
his gln pro gly gly gly lys val gln ile ile asn
lys lys leu asp leu ser asn val gln ser lys cys
gly ser lys asp asn ile lys his val pro gly gly
gly ser val gln ile val tyr lys pro val asp leu
ser lys val thr ser lys cys gly ser leu gly asn
ile his his lys pro gly gly gly gln val glu val
lys ser glu lys leu asp phe lys asp arg val gln
ser lys ile gly ser leu asp asn ile thr his val
pro gly gly gly asn lys lys ile glu thr his lys
leu thr phe arg glu asn ala lys ala lys thr asp
his gly ala glu ile val tyr lys ser pro val val
ser gly asp thr ser pro arg his leu ser asn val
ser ser thr gly ser ile asp met val asp ser pro
gln leu ala thr leu ala asp glu val ser ala ser
leu (6-347, R3)

SEQ ID NO: 20 gln glu phe glu val met glu asp his ala gly thr
tyr gly leu gly asp arg lys asp gln gly gly tyr
thr met his gln asp gln glu gly asp thr asp ala
gly leu lys ala glu gln ala gly ile gly asp thr
pro ser leu glu asp glu ala ala gly his val thr
gln ala arg met val ser lys ser lys asp gly thr
gly ser asp asp lys lys ala lys gly ala asp gly
lys thr lys ile ala thr pro arg gly ala ala pro
pro gly gln lys gly gln ala asn ala thr arg ile
pro ala lys thr pro pro ala pro lys thr pro pro
ser ser gly glu pro pro lys ser gly asp arg ser
gly tyr ser ser pro gly ser pro gly thr pro gly
ser arg ser arg thr pro ser leu pro thr pro pro
thr arg glu pro lys lys val ala val val arg thr
pro pro lys ser pro ser ser ala lys ser arg leu
gln thr ala pro val pro met pro asp leu lys asn
val lys ser lys ile gly ser thr glu asn leu lys
his gln pro gly gly gly lys val gln ile val tyr
lys pro val asp leu ser lys val thr ser lys cys
gly ser leu gly asn ile his his lys pro gly gly
gly gln val glu val lys ser glu lys leu asp phe
lys asp arg val gln ser lys ile gly ser leu asp
asn ile thr his val pro gly gly gly asn lys lys
ile glu thr his lys leu thr phe arg glu asn ala
lys ala lys thr asp his gly ala glu ile val tyr
lys ser pro val val ser gly asp thr ser pro arg
his leu ser asn val ser ser thr gly ser ile asp
met val asp ser pro gln leu ala thr leu ala asp
glu val ser ala ser leu In a preferred embodiment of the invention, said type IIA diseased tau proteins have the following properties:
a) the proteins are N- and C-terminally truncated (Example 6)
b) are efficient pathological promoters of microtubule assembly (Example 3; FIG. 28C)
c) their pathological microtubule assembly promoting activity can be removed by specific compounds such as for example inhibitory monoclonal antibodies or derivatives thereof (Example 12)
d) the proteins are not present in normal healthy brain (Example 6)
e) significantly impair intracellular transport functions (Example 16)
f) their pathologic activity relies on high affinity binding to microtubular network and its functional impairment (Example 3)
g) they appear to be are conformationally different from normal tau (Example 6).

In another preferred embodiment of the invention type IIB molecules have the following properties:
a) the proteins are N- and C-terminally truncated
b) are less effective in promoting microtubule assembly than type IIA
c) the proteins are not present in normal healthy brain
d) are likely to impair microtubule function by binding to it however to a lesser extent than observed for type IIA
e) They appear to be conformationally different from normal tau.

In still another preferred embodiment of the invention the epitopes of type IIA and B molecules were identified in a similar way as described for type I molecules. The significance for type II molecules of all these epitopes and their relationship to function on microtubules are demonstrated by the mutant forms which showed that they are contributing at various extent to the activity of N- and C-terminally double truncated tau molecules such as shown in the example of type IA.

An inhibitor useful in the composition of the present invention is therefore any inhibitor capable of modulating the pathological interaction of type IIA molecules with microtubules resulting in, pathological microtubules'. The term, pathological microtubules' as used herein refers to microtubules modified by type II molecules. The mode of action of such an inhibitory molecule consists of an interaction with either microtubules, microtubule associated molecules including tau and pathological derivatives thereof. As a source of inhibitors can be used libraries of small molecules of defined chemical structure and composition, peptide libraries, antibody libraries free in the solution or displayed on synthetic surfaces, or on phages or bacteria or ribosomes (ribosomal display) and similar technologies known in the art.

In a preferable embodiment these 'inhibitors' may be specific for the epitope or epitopes encompassed in type IIA molecules, by e.g. blocking the epitope or may be directed to various domains on type IIA molecules, as long as they prevent or disturb its pathological or biological activity in vitro or in vivo. The inhibitory effect can be defined quantitatively e.g. by measuring residual microtubule assembly promoting activity by normal tau or by measuring intracellular microtubule parameters such as outgrowth, stability or intracellular transport.

In another embodiment type IIA molecules can be inhibited or neutralized by derivatives thereof for example as dominant negative proteins expressed in the respective cell. As described in the present invention for screening inhibitory molecules, type IIA peptides and derivatives thereof such as peptides containing deletions or mutations can be tested or screened for their effects on inhibiting the pathological effects of N- and C-terminally double truncated tau molecules.

The therapeutic effect is achieved by inhibiting impairment of microtubule structure and functions.

Accordingly, another object of the invention is to provide pharmaceutical compositions containing a specific inhibitor for the type IIA tau molecules of the invention, optionally in combination with a pharmaceutically acceptable carrier and/or diluent.

In another preferred embodiment the present invention relates especially to SEQ ID NO: 11 as a prototype of type IIA group molecules.

Still another object of the invention is to provide a method for the in vitro conversion of normal microtubules into a pathological state wherein normal tau protein is incubated with type IIA or -B of the present invention under physiological conditions which allow the interaction of said type IIA or -B with microtubules generating pathological microtubules.

The invention further relates to a screening assay allowing screening any molecule libraries for compounds capable of neutralising the pathological effects of type IIA molecules. In the present test molecules are screened for their property to eliminate and/or neutralize type IIA molecules and to restore physiological microtubule parameters and functions caused by type II molecules. The drug screening assay consists of the following steps:

(1) formation of pathological microtubules in the presence of type IIA molecules and tubulin under appropriate conditions (Examples 3 and 4, resp.).
(2) incubation of these pathological microtubules with the candidate drug to be tested
(3) examination of the result with respect to neutralising the effect of type IIA molecules on microtubules. (Examples 9 and 12, resp.).

An in vitro screening system for inhibitors may be established which alleviates its effect on microtubules caused by pathological, N- and C-terminally double truncated tau type IIA. These 'inhibitors' may be specific for the epitope or epitopes encompassed in type IIA molecules, by e.g. blocking the epitope or may be directed to various domains on type IIA molecules, as long as they prevent or disturb its activity. The inhibitory effect can be quantified by measuring microtubule assembly dynamics. As a source of inhibitors can be used libraries of small molecules of defined chemical structure and composition, peptide libraries, antibody libraries free in the solution or displayed on the surface of synthetic surfaces of phages or bacteria or ribosomes (ribosomal display) and similar technologies known in the art.

For the object of the present invention it is sufficient that the drug to be tested is effective in reducing the amount of type IIA molecules and/or their activity, thus fulfilling a supplementary therapeutic effect, although a total removal of the type IIA activity is preferred.

The person skilled in the art knows how to employ the method of the present invention for a variety of different purposes which all fall under the scope of protection of the present invention.

A further object of the invention is to provide a method for the validation of drugs in living cells i.e. neurons or neurone like cells expressing type II molecules (type II Cellular assay). Alternatively primary neuronal culture derived from transgenic animals or other primary neuronal cells derived from various sources expressing type IIA molecules can be used.

The term "neurons expressing type II molecules" as used above, refers to cells which stably express the molecules or which have the capacity to express type IIA molecules and into which a functional type IIA gene has been introduced either by cell culture techniques or via transgenesis as exemplified below.

In a preferred embodiment said cell expressing type IIA molecules is a neuroblastoma, or pheochromocytoma cell or a primary culture of nerve cells derived from transgenic animal expressing type IIA molecules.

The person skilled in the art is aware of the fact that the sequence of the introduction of the genes encoding the type IIA molecules is irrelevant for the purpose of the method of the invention.

The present invention relates to a method for testing drugs effective in inhibiting type IIA in promoting abnormal microtubule formation and function in a cellular system expressing type IIA molecules comprising the following steps:

a) introducing a functional gene encoding type II molecules under the control of suitable regulatory regions into a cell expressing normal tau protein
b) allowing the formation of complexes between type IIA tau and microtubules (pathological microtubules)
c) applying the drug to be tested to the cells harboring the resulting complexes
d) examining the effect of said drug on type IIA biological activity such as modifications of the microtubule network and its associated functions.

In still another most preferable embodiment of the present invention is the phenotype of neurons expressing type IIA molecules. Neurons expressing these molecules under appropriate conditions causes the perturbance of intracellular transport processes. Furthermore neurons expressing type IIA molecules undergo cell death under appropriate stress conditions (Example 4).

Said method is particularly advantageous, since the system involved which is based on the use of continuously growing cell lines which provide a close image of the in vivo situation provide an ample supply of type IIA molecules located intracellularly is generated allowing drug screening for compounds effective in alleviation of intracellular type IIA effects.

In a preferred embodiment the readout of this cellular assay is adapted for low- or high throughput quantification systems. The term "appropriate conditions" in connection with mentioned phenotypes leading to disruption or impairment of microtubular transport and/or to neuronal death refers to any condition which allows appearance of said phenotypes as shown in the example.

For the object of the present invention it is sufficient that the potential drug either screened by this system, or validated in the system or drug of the third origin, is effective in the reduction of the scale of the phenotypes, thus fulfilling a supplementary function in therapy, although a total elimination or reduction of the diseased phenotypes by the drug is preferred.

In addition to stably growing cell lines or primary cells, the respective invention can also be extended to an analogous readout system using cells derived from whole animals which express type IIA or -B molecules in their neurons (The transgenic animal model will be exemplified below).

The person skilled in the art knows how to employ the method of the present invention for a variety of different purposes which all fall under the scope of protection of the present invention.

In a preferred embodiment said cells and transgenic animals stably expressing N- and C-terminally double truncated type IIA tau forms allow mapping of disease pathways yielding precious information leading to new molecules relevant to pathogenesis of Alzheimer's disease, its diagnosis and treatment. These screening and identification procedures include mRNA expression based screening technologies as well as protein based technologies.

In a preferred embodiment said type I and type IIA and -B molecules or derivatives thereof provide also a recombinant DNA construct which can be introduced into the genome of non-human animals for the purpose of providing a transgenic animal model carrying and expressing the pathogenic N- and C-terminally double truncated forms of type IA, type IIA and -B described above. Transgenic animals according to the invention include animals into which the construct has been introduced directly as well as progeny of such animals which retain the ability to express the construct. The transgene sequence is a polynucleotide sequence functionally linked to a ubiquitously expressed or otherwise to a tissue specific promoter. The transgene DNA encoding type IA and type IIA and -B molecules is preferentially cDNA and/or genomic DNA derived from either animal or human sources.

Transgenic animals expressing said type I and type IIA and -B molecules are expected to develop functional changes at the cellular and/or the organ level which are phenotypically related to Alzheimer's disease. These include histological changes, RNA expression changes, changes of cellular physiological parameters and preferably behavioural changes characteristic of AD. In mature neurons of transgenic animals the expression of Type I type and IIA and -B molecules has not previously been tested.

It is to expect that the level at which type I, type IIA and -B transgenes are expressed in the transgenic animal (i.e. the level of transgene mRNA), is an important parameter for obtaining consistent pathophysiological defects in the transgenic animal. By breeding and intercrossing animals carrying the transgenes, the pathological features can be enhanced, attenuated or otherwise modulated such as e.g. by introducing the transgene into animal strains currently serving as disease models, animals expressing other transgenes or animals lacking functional expression of genes (see Example 14).

More particularly the present invention provides a transgenic non-human animal cell, wherein DNA encoding a human type I and type IIA and -B molecule is expressed under the transcriptional control of suitable ubiquitous or otherwise tissue specific promoters including regulable modifications thereof.

Cells manipulated according to the invention may be prepared by any known transfection technique. The DNA sequence may be introduced by direct genetic manipulation or into an earlier generation of the cell. Thus, the cells may be obtained from transgenic animals and cultured in vitro. Also the transgenic animals may be generated according to well established methods, such as manipulation of embryos, e.g. by gene transfer into embryonic stem cells, retroviral infection of early embryos or pronuclear microinjection. The pronuclear microinjection technique is preferred. Transcription units obtained from a recombinant DNA construct of the invention are injected into pronuclei of animal embryos and the obtained founder transgenics are bred.

The results obtained in the offspring can be analysed using various techniques well known in the art. Models based on cells and animals of the invention may be used for example to identify and assess the efficacy of potential therapeutic agents in neurodegenerative diseases where tau and N- and C-terminally double truncated tau derived molecules but also other molecules related to Alzheimer's disease such as APP and derivatives thereof can be analysed. In particular such models may be used in screening or characterisation assays for detecting agents likely to prevent the pathogenic effects of N- and C-terminally double truncated tau derived molecules described here.

Accordingly in a further aspect the invention comprises a method for testing a potential therapeutic agent for a specified condition, in particular a neurodegenerative disease, preferably AD, wherein a cell derived from a transgenic animal expressing the said double truncated forms of tau is used as target cell. More particularly it comprises such a method, wherein the therapeutic agent such as e.g. antibodies or their derivatives is administered to a transgenic animal of the invention or introduced by crossbreeding or genetic manipulation and further tested by assay systems presented above. Moreover the invention comprises a screening or characterisation assay consisting in or including such a method, as well as a screening assay kit comprising cells of the invention. Methods for screening potential therapeutic agents using cell lines expressing type I and type IIA and -B molecules of the present invention are given in the present invention (see Example 15). The cells and animals of the present invention may be used in analogous manner.

Another object of the invention is to provide pharmaceutical compositions containing a specific inhibitor for N- and C-terminally double truncated forms of tau proteins optionally in combination with pharmaceutically acceptable carrier and/or diluent.

The term 'specific inhibitor for the N- and C-terminally double truncated tau' refers to substances which specifically inhibit the actions of said double truncated tau proteins. The nature of an inhibitor can be an antibody, an engineered, derived molecule thereof, any peptide or defined chemical composition exhibiting the desired inhibitory activity in the test systems of the present invention.

Another object of the invention is an antibody or derivative thereof which specifically recognises an epitope of the invention and is able to partially or completely inhibit the pathological activities of N- and C-terminally double truncated tau molecules.

The term 'oligo- or polypeptide comprising an epitope, or epitopes of the invention' refers to peptides which in their two- or three-dimensional structure reconstitute the epitope of the invention which is specifically recognized by an antibody directed thereto. Moreover, said oligo- or polypeptides may solely consist of the amino acids representing said epitope(s) or they may comprise additional amino acids. The construction of such oligo- or polypeptides is well known in the art.

In a preferred embodiment the present invention relates to monoclonal antibodies and derivatives thereof either native or recombinant, immobilised, free in solution or displayed on the surface of various molecules or bacteria, viruses, or other surfaces. The antibodies and their derivatives are able to partially or completely inhibit the biologic activities of N- and C-terminally double truncated tau molecules. Such a specific antibody activity has been shown using the monoclonal antibody DC44 raised against said double truncated tau molecules isolated from Alzheimer diseased brain tissue (Examples 10 and 11, resp.).

Said antibody(-ies) has many other variants (DC82, DC136, etc.) and may be a serum derived or a monoclonal antibody or any derivative thereof. The production of both monoclonal and polyclonal antibodies to a desired epitope is well known in the art (43). Furthermore, said antibody may be a natural or an antibody derived by genetic engineering, such as a chimeric antibody derived by techniques which are well understood in the art. Moreover, said antibody also refers to a fragment of an antibody which has retained its capacity to bind the specific epitope, such as a Fab fragment or single chain Fv mini-body, or intracellularly expressed single chain antibodies called intrabodies.

In a most preferred embodiment the present invention relates to a pharmaceutical composition for use in the treatment of Alzheimer's disease.

Again, said pharmaceutical composition may be administered to a patient in need thereof by route and in dosage which is deemed appropriate by the physician handling the case.

In another preferred embodiment of the present invention, said pharmaceutical composition contains as the specific inhibitor at least one monoclonal antibody or small molecule or derivative thereof binding any part or group of epitopes listed above leading to their alteration and/or neutralisation, partial or complete thereof (see Examples 10, 11 and 12, resp.).

Another object of the invention is to provide diagnostic compositions for the detection and/or monitoring of Alzheimer's disease comprising a) an epitope(s) of the invention; b) an antibody of the invention or a derived molecule thereof.

The diagnostic composition of the invention may comprise for example an antibody of the invention which specifically recognizes one member of type IA or type II group molecule or its epitope(s) or an enhanced level of type IA or type IIA molecules in a sample to be tested. In another embodiment, said diagnostic composition may comprise an antibody of the invention directed to one of the epitopes of the invention. Thus an Alzheimer disease state correlating sample may be detected by treating said sample with an antibody recognising the epitope of the invention. The antibody—epitope (hapten) complex may be visualized using a second antibody directed to the antibody of the invention and being labelled according to methods known in the art (43).

In still another embodiment of the present invention, said diagnostic composition may consist of an epitope of the invention and an antibody of the invention. Treatment of a sample with said antibody may give rise to conclusions with regard to the disease state of the corresponding patent, if the binding of said antibody to said sample is brought in relation to binding of said antibody to said epitope of the invention used as a reference sample.

In still another embodiment, the diagnostic composition may comprise type IA or type IIA molecules and an antibody of the invention. Activity of both types of molecules may be monitored with respect to normal tau neutralising capacity of the sample, compared to the recombinant type IA molecule (e.g. SEQ ID NO:1) and IIA molecules (SEQ. ID NO: 11-18) of the invention. From the quantified aberrant activity of type I molecule, the level of the molecules contained in said sample and therefore the disease state of the patient may be deduced. The type IA activity may e.g. be deduced by measuring the residual activity of normal tau left unreacted with type I molecules. Type II activity may be deduced by measuring further activity of type II molecules in a microtubule-assembly assay.

The person skilled in the art is in the position to design other test systems which combine any of the above objects of the invention. It is to be understood that all conceivable combinations fall within the scope of protection of the present invention.

Another object of the invention is to provide a method for the in vitro diagnosis and/or monitoring of Alzheimer's disease comprising assaying cerebrospinal fluid isolates of a patient, carrying out a biopsy of nerve tissue for the presence of N- and C-terminally double truncated tau molecules of type IA and type IIA molecule or its epitope(s) and for the level of their normal tau inhibitory activity.

The 'cerebrospinal fluid isolate of a patient' is obtained by standard medical procedures.

In a further embodiment the invention relates to type I and type II molecules that are identical or homologous to the said amino acid sequence of type IA and type IIA, respectively molecules and immunogenic fragments derived thereof capable of inducing an immune response in animals. In accordance with the present invention, it was found that both type I and type II molecules can be used (a) as immunogens for production of inhibitory antibodies and as central part of vaccines used for immunisation against the disease.

Upon parenteral application, all sequences and epitopes listed above and type I and II isolated from diseased brain tissue are immunogenic and lead to the production of antibodies specifically directed against said type I and II proteins and derivatives thereof (Examples 10 and 13, resp.).

In a most preferred embodiment type I and II molecules or derivatives thereof are capable of inducing an immune response directed against the primary, secondary and/or the ternary structure of said molecules. In the host, the resulting immune response is therefore capable of distinguishing between healthy and diseased forms of tau and its derivatives. This characteristic of the invention can be used as vaccine emphasizing on the unique quality of these N- and C-terminally double truncated tau forms in inducing a disease-specific immune response.

It is understood that, for the pathogenic N- and C-terminally double truncated tau polypeptides embraced herein, natural variations are existing amongst individual cases of Alzheimer's diseases. These variations may exist in (an)

amino acid difference(s) in the overall sequence or by deletions, substitutions, insertions, inversions or additions of (an) amino acid(s) in said sequence. Such amino acid substitutions of the exemplary embodiments of this invention are within the scope of the invention. Thus, natural variations not essentially influencing the immunogenicity of the polypeptide, are considered immunologically equivalent variants of the said double truncated forms of tau polypeptides according to the invention.

When a type IA and IIA N- and C-terminally double truncated tau polypeptide is used for e.g. vaccination purposes or for raising antibodies, it is however not necessary to use the whole polypeptide described in the present invention. It is also possible to use a fragment of these polypeptides that are capable of inducing an immune response against that entire polypeptide, a so-called immunogenic fragment.

Therefore, this embodiment of the invention not only relates to polypeptides according to the invention, but also to derived fragments of those polypeptides that are still capable of inducing an immune response against the polypeptides (so-called immunogenic fragments).

For the purpose of giving an example, the immunogenicity in animals of either a recombinant type IA and IIA peptide or a fraction of type IA and IIA N- and C-terminally double truncated diseased tau derived from a diseased human Alzheimer brain is given (Example 3)

BRIEF DESCRIPTION OF THE DRAWINGS

The invention is further described by the following examples and the drawing figures, yet without being restricted thereto.

Figure 16:
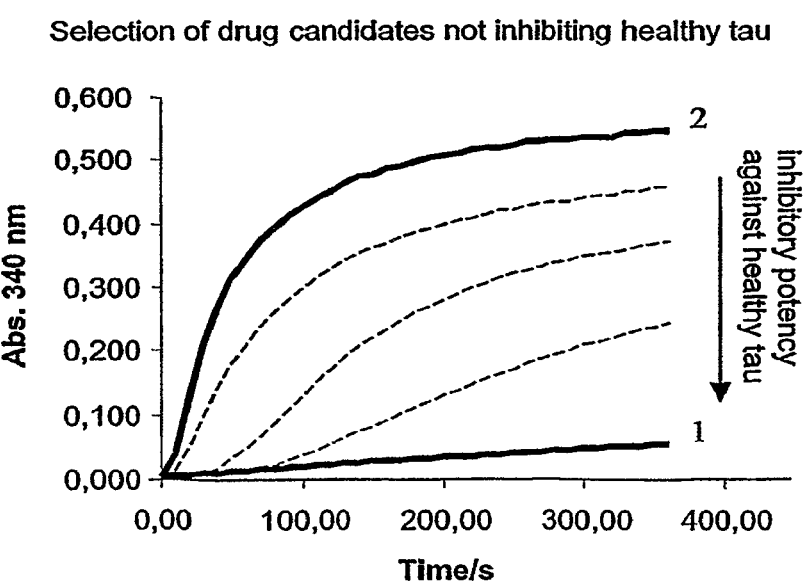

FIG. 16: Second round screening for drug candidates capable to neutralize tau type IIA molecules and discriminate them from normal tau (step 2). Drug candidates selected in step 1 were preincubated with healthy tau and the effect on microtubule assembly was assayed. The bottom curve (1) represents maximal inhibition of healthy tau and the top curve (2) indicates no inhibition of healthy tau. Middle curves show drug candidates with different inhibitory activity against healthy tau.

Figures 17, 18:
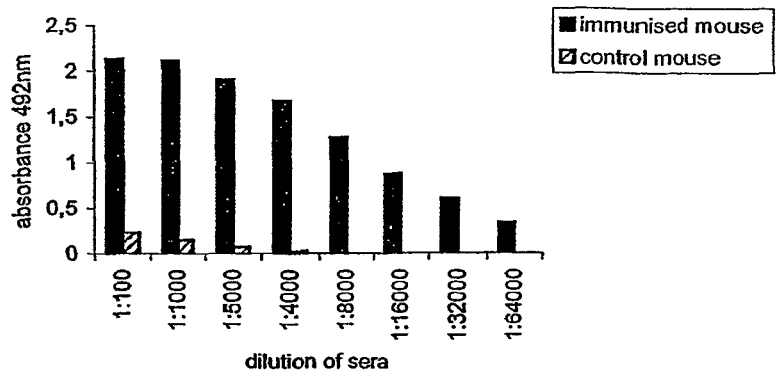

FIG. 17: Specific antibody levels in prefused mice sera determined by ELISA. The levels of specific antibodies in sera of mice immunized with AD derived tau were tested in ELISA on the same antigen. All five sera showed high anti-tau binding activity to said tau protein. FIG. 17 represents levels of specific antibodies in one of the immunized mice. Serum from a mouse immunized with irrelevant protein was used as a control.

FIG. 18: ELISA reactivity of monoclonal antibodies with AD-brain derived tau (fraction #19) and control healthy brain-derived tau (DC 20: monoclonal antibody with irrelevant specificity. Shown data represent mean values from three parallel experiments). #DC44: deposited on 4 Jun. 2002 at the ECACC Porton Down, Salisbury, Wilts, UK under the deposition number 02060767; *the immunogen for these antibodies was N- and C-terminally truncated tau type I proteins isolated from Alzheimer brains (fraction 19); DC 20: monoclonal antibody with irrelevant specificity. Shown data represent mean values from three parallel experiments.

Figures 19, 20:
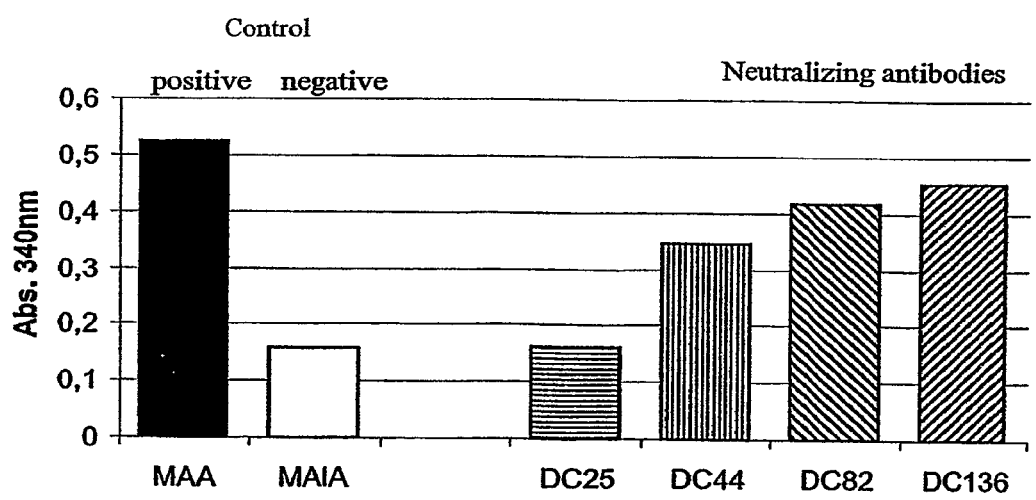

FIG. 19: ELISA reactivity of monoclonal antibodies with recombinant tau molecules (DC 20: monoclonal antibody with irrelevant specificity. Shown data represent mean values from three parallels).

FIG. 20: Screening for neutralizing antibodies directed against AD-brain derived tau type IA (fraction #19). Antibodies were preincubated with native tau type IA (fraction #19) and subsequently mixed with healthy human tau, tubulin and GTP. The formation of microtubules was determined spectrophotometrically after 5 min at 37° C. The bars represent a mean value of three independent experiments. MAA—microtubule assembly assay with healthy human tau. MAIA—microtubule assembly inhibition assay with healthy human tau preincubated with tau type IA (without antibody).

Figure 21:
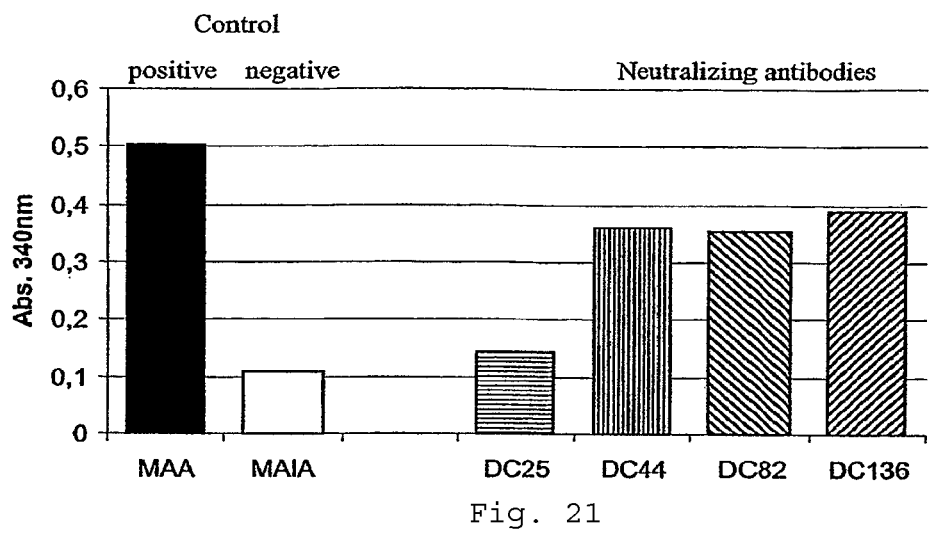

FIG. 21: Screening for neutralizing antibodies directed against recombinant tau type IA (SEQ ID NO:1).

Figure 22:
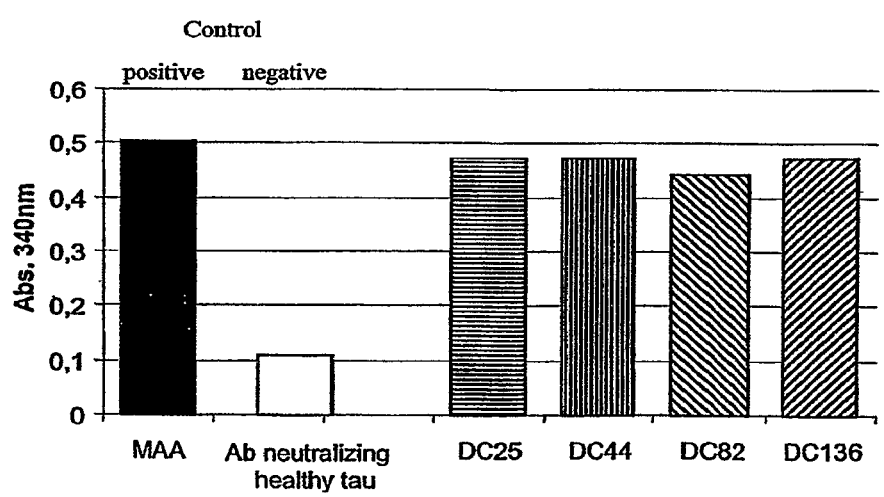

FIG. 22: Screening for drug candidates capable of neutralizing tau type IA molecules and of discriminating them from healthy tau. Antibodies neutralizing tau type IA were preincubated with healthy tau and subsequently mixed with tubulin and GTP. The formation of microtubules was determined spectrophotometrically after 5 min at 37° C. The bars show the mean value of three independent experiments. MAA—microtubule assembly assay with healthy tau. As a negative control an antibody neutralizing healthy tau was used.

Figure 23:
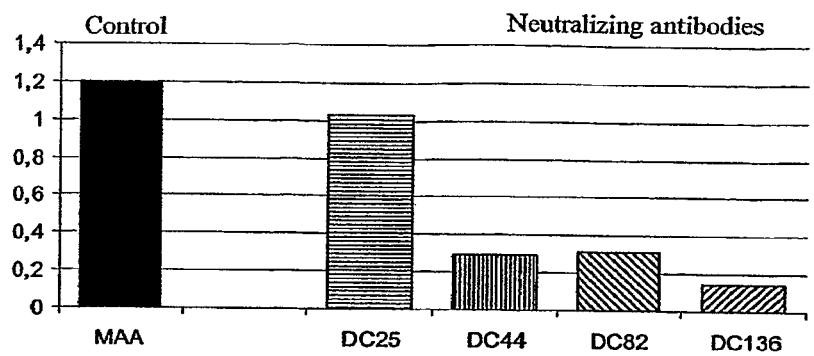

FIG. 23: Neutralisation of pathological activity of recombinant tau type IIA (SEQ ID NO.12) by monoclonal antibodies. Antibodies were preincubated with recombinant tau type IIA and then mixed with tubulin and GTP. The formation of microtubules was determined spectrophotometrically after 5 min at 37° C. The bars represent the mean value of three independent experiments. MAA—microtubule assembly assay with tau type IIA (without antibody).

Figure 24:
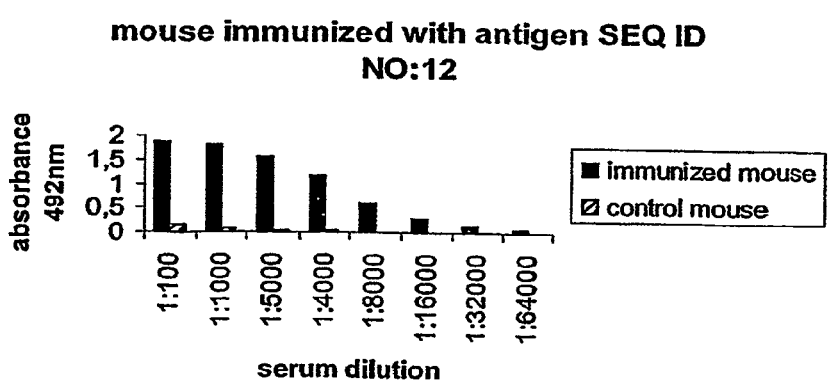

FIG. 24: Levels of antibodies against recombinant tau type IIA (SEQ ID NO.:12) detected by ELISA.

Figure 25:
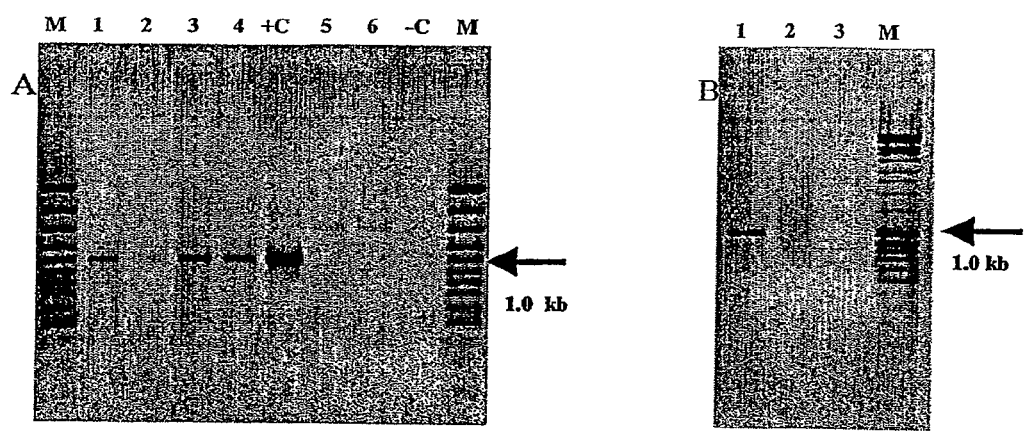

FIG. 25: Genotyping of transgenic animals. Panel A shows genotyping of the parental generation of transgenic animals. Specific amplification of double truncated sequence of DNA from genomic DNA in lanes 1, 2, 3 and 4 indicates the presence of a specific transgene in genomic DNA extracted from tails of the progeny of foster mothers. These animals represent the parental generation of transgenic animals bearing double truncated type IIA tau molecules. In this example, positive (+C) and negative (−C) and two additional negative samples (5, 6) are shown (M=size marker). The arrow indicates the expected PCR product size expected in transgene positive animals. Panel B. Genotyping of animals from F1 generation. Genomic DNA was extracted from tail tips and double truncated tau specific DNA sequence was identified and are shown in lanes 1. Lane 2 and 3 show negative controls. Identification of a tau specific DNA fragment in the F1 generation confirms the inheritability of these transgenes.

Figure 26:
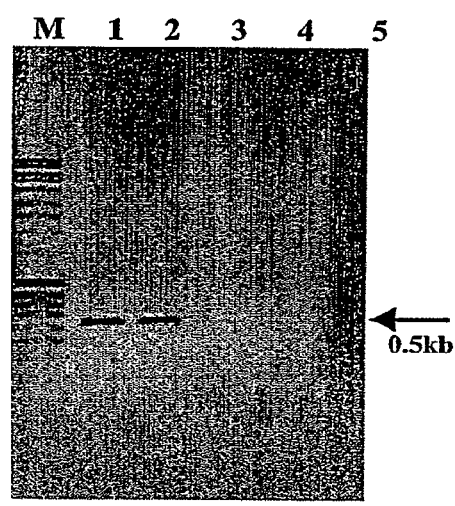

FIG. 26: Gene expression of double truncated human tau transcripts in the F1 generation of transgenic animals. RNA was extracted from flash frozen tissue of transgenic animals and subjected to reverse transcription followed by specific amplification of the cDNA. An example shows transgene expressing animals in lanes number 1 and 2. Lanes 3-5 represent non-expressing controls while lane 5 shows a non-specific signal typically emerging in non-transgenic animal when using this method. This example indicates the presence of double truncated tau specific mRNA expressed from the transgene in experimental animals.

Figure 27:
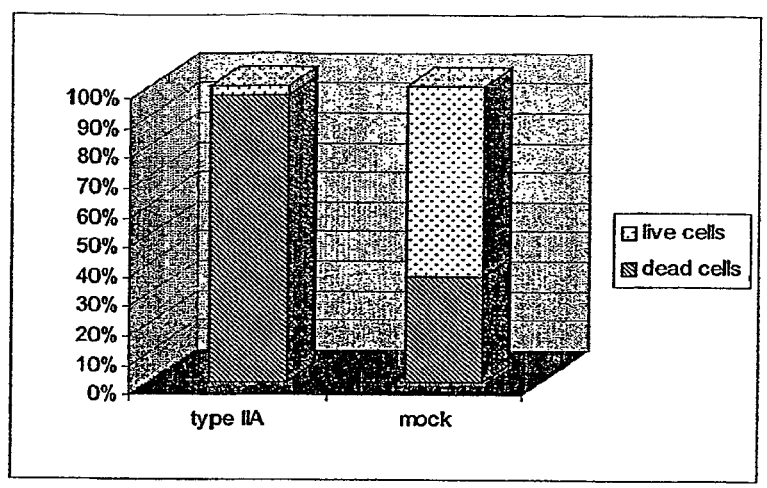

FIG. 27: Cell death caused by type IIA molecule overexpression after 6 day in vitro differentiation. Comparison of the cell viability of SY5Y cells transfected with double truncated tau type IIA (type IIA) and non-transfected control neuron-like cells (mock), respectively.

Figure 28A:
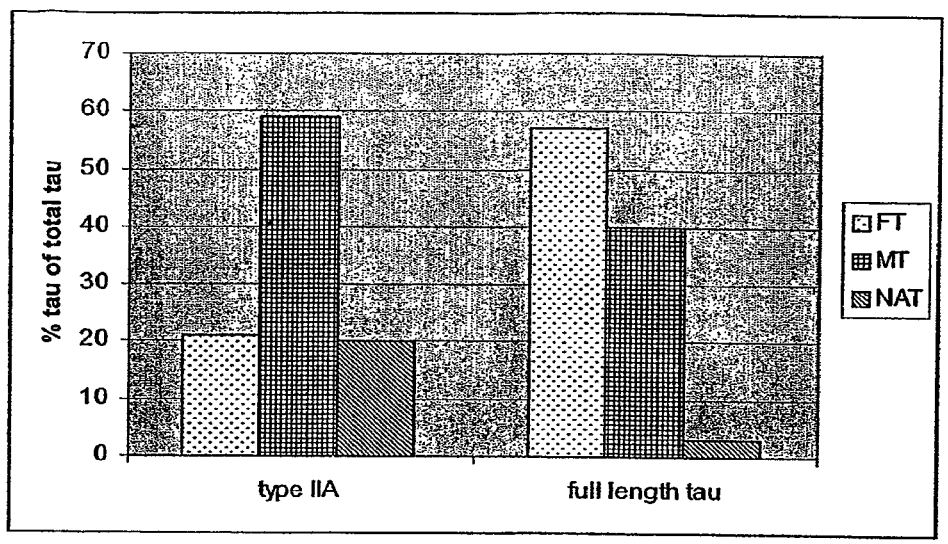
Figure 28B:
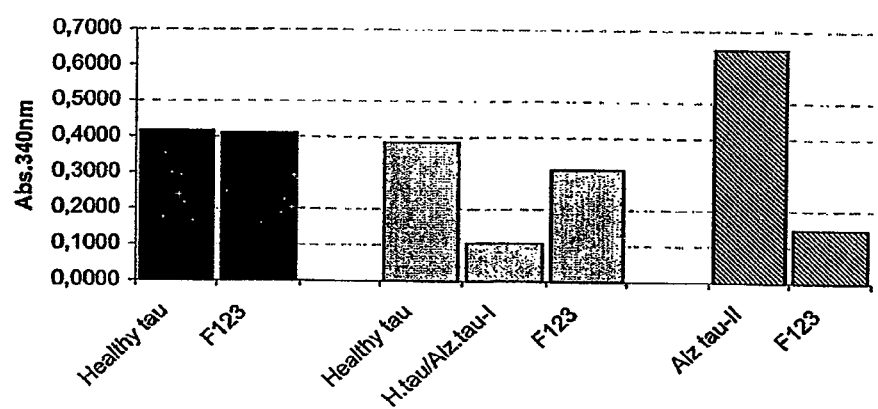

FIGS. 28A, 28B, and 28C: A: Increased binding affinity of type IIA molecules to microtubules is showed by using cellular fractionation of tau from stably transfected cells expressing type IIA double truncated molecules and full-length tau. Isolation of free tau (FT), microtubule bound tau (MT) and nucleus associated tau (NAT) was performed as described. B: Inhibition of tau type IA and IIA, microbutule polymerisation assay, respectively, by organic compound F123; C: Direct comparison between absorption measurement and microtubule polymerisation shown by electromicroscopic analysis.

Figure 29:
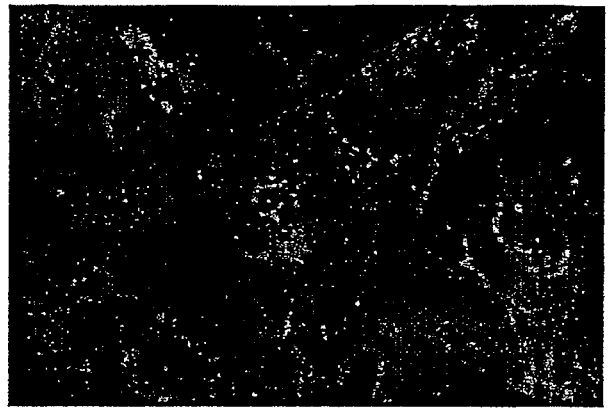

FIG. 29: Logarithmically growing SH-SY5Y cells stained with MitoFluor. Regular distribution of mitochondria in cell bodies and processes.

Figure 30:

FIG. 30: Logarithmically growing tau tpe IIA molecule expressing SH-SY5Y cells stained with MitoFluor. Perinuclear clustering of green-labelled mitochondria around the centrosome area of the cell.

EXAMPLES

Example 1

Microtubule Assembly with N- and C-Terminally Double Truncated Tau Type IA and Type IB Molecules

Figure 1:
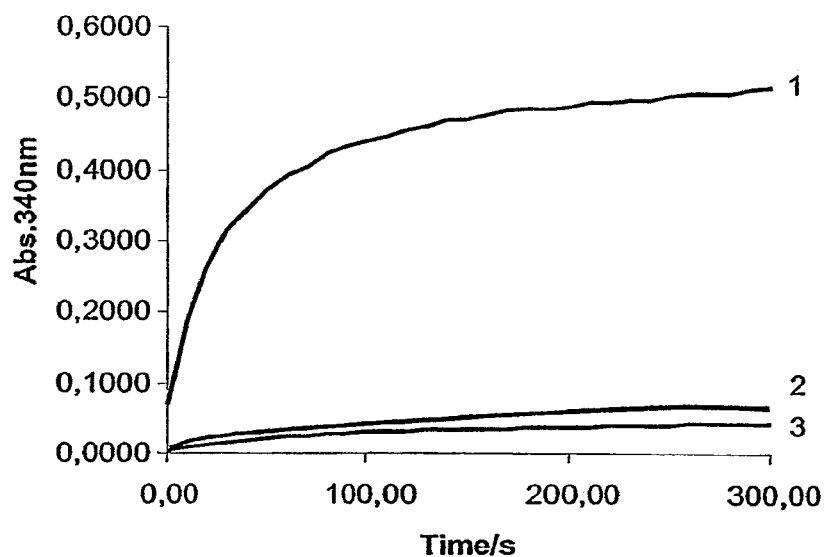
FIG. 1: Microtubule assembly with N- and C-terminally double truncated tau type IA and type IB molecules. Microtubule assembly using normal health tau (1), tau type IA (2) and tau type IB (3).

The physiological function of healthy tau consists in stabilizing microtubules (MTs). This function can be measured by a microtubule assembly assay (MAA). In this examples, the MAA reactions were carried out using three types of tau molecules: normal healthy human tau, recombinant forms of tau type IA (SEQ ID NO: 1) and tau type IB (SEQ ID NO: 4). Normal human tau, tau type IA and type IB were assayed individually in separate reactions. Single preparations of tau at 0.1 mg/ml were mixed with purified porcine brain tubulin at a final concentration of 1 mg/ml and 1 mM GTP, all materials in polymerisation buffer (100 mM PIPES, pH 6.9, 1 mM MgSO$_4$, 2 mM EGTA). Tau was added last to initiate the promotion of MT assembly. After gentle and rapid mixing, the samples were pipetted into quartz microcuvettes and equilibrated at 37° C. in a thermostatically controlled spectrophotometer (Beckman Coulter DU640). The turbidity was continuously monitored at 340 nm in 10 s intervals for a period of 20 min. The top curve 1 (FIG. 1) shows microtubule assembly promotion capacity of normal healthy tau. In contrast, neither type IA (curve 2) nor type IB (curve 3) exhibited this activity of normal tau and lacked any MT assembly promotion in MAA.

Example 2

Inhibition of Microtubule Assembly by N- and C-Terminally Double Truncated Tau Type IA and Type IB Molecules

Figure 2:
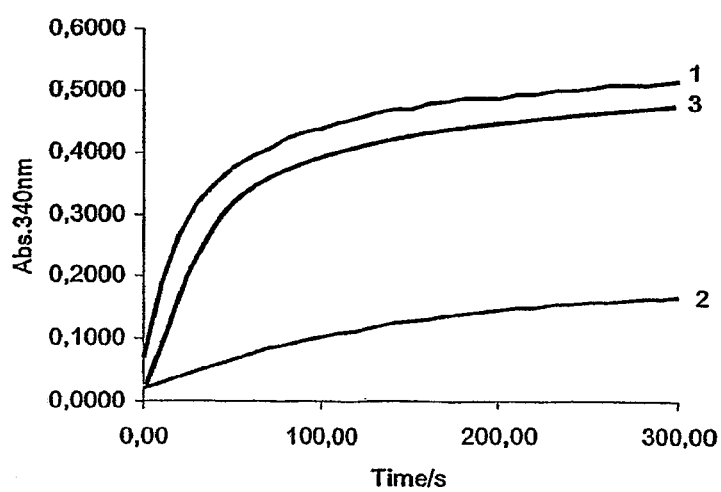
FIG. 2: Inhibition of microtubule assembly by N- and C-terminally double truncated tau type IA and type IB molecules. Microtubule assembly using (1) healthy tau, (2) inhibition by tau type IA, (3) lack of inhibition when using tau type IB.

Both tau type IA and IB molecules lack functional activity when applied in a the MT assembly assay (MAA). Surprisingly, tau type IA molecules show an inhibitory effect on tubulin in microtubule assembly. In contrast, type IB proteins (despite similar primary structure) do not inhibit functional activity of tubulin in MAA. For inhibition of microtubule assembly, recombinant forms of tau type IA (SEQ ID NO:1) and type IB (SEQ ID NO:4) were used. The assembly-inhibition reactions were carried out separately using type IA and type IB proteins. Human tubulin (2 mg/ml) was mixed with either type IA molecules (0.2 mg/ml) or type IB molecules (0.2 mg/ml). The mixtures were incubated 1 hr at 37° C. with gently shaking. To the mixtures kept on ice normal human tau (0.1 mg/ml) and GTP (final concentration of tubulin in the mixture is 1 mg/ml and GTP 1 mM) were added in polymerization buffer (100 mM PIPES, pH 6.9, 1 mM MgSO$_4$, 2 mM EGTA). After gentle and rapid mixing, the samples were pipetted into quartz microcuvettes and equilibrated at 37° C. in a thermostatically controlled spectrophotometer (Beckman Coulter DU640). The turbidity changes were measured at 340 nm in 10 sec intervals over a period of 5 min. The top curve 1 (FIG. 2) demonstrates that normal human tau alone was fully capable to induce tubulin polymerisation. Preincubation of tubulin with type IA abolished microtubule assembly (FIG. 2, bottom curve 2). On the contrary, incubation of tubulin with type IB does not inhibit the microtubule assembly capacity of normal tau (FIG. 2, curve 3), despite having molecular mass in the same range than type IA.

TABLE

Influence of N- and C-terminal of double truncated tau molecules on microtubule polymerisation

Type IIA

| SEQ ID NO: | R1 R2 R3 R4 | Abnormal MT Activity |
|---|---|---|
| 11 | 69 ———— 333 | + |
| 12 | 93 ———— 333 | + |
| 13 | 69 ———— 363 | + |
| 14 | 93 ———— 363 | + |

| | R1 R3 R4 | |
|---|---|---|
| 15 | 93 ———— 302 | + |
| 16 | 69 ———— 302 | + |
| 17 | 93 ———— 332 | + |
| 18 | 69 ———— 332 | + |

Type IIB

| | R1 R2 R3 R4 | |
|---|---|---|
| 19 | 6 ———— 378 | - |

| | R1 R3 R4 | |
|---|---|---|
| 20 | 6 ———— 347 | - |

Type 1A

| SEQ ID NO: | R1 R2 R3 R4 | Abnormal MT Activity |
|---|---|---|
| 1 | 239 ———— 333 | + |
| 2 | 237 ———— 333 | + |
| 3 | 239 ———— 318 | + |

Type 1B

| | | |
|---|---|---|
| 4 | 239 ———— 326 | - |
| 5 | 239 ———— 328 | - |
| 6 | 239 ———— 331 | - |
| 7 | 239 ———— 334 | - |
| 8 | 239 ———— 340 | - |
| 9 | 239 ———— 343 | - |

| | R1 R3 R4 | |
|---|---|---|
| 10 | 208 ———— 302 | - | numbering SEQ ID NO: 11-14; 19 according to the shortest R4 isoform
numbering SEQ ID NO: 15-18; 20 according to the shortest R3 isoform

Example 3

Activity of N- and C-Terminally Double Truncated Tau Type IIA and IIB Molecules in Microtubule Assembly

Figure 3:
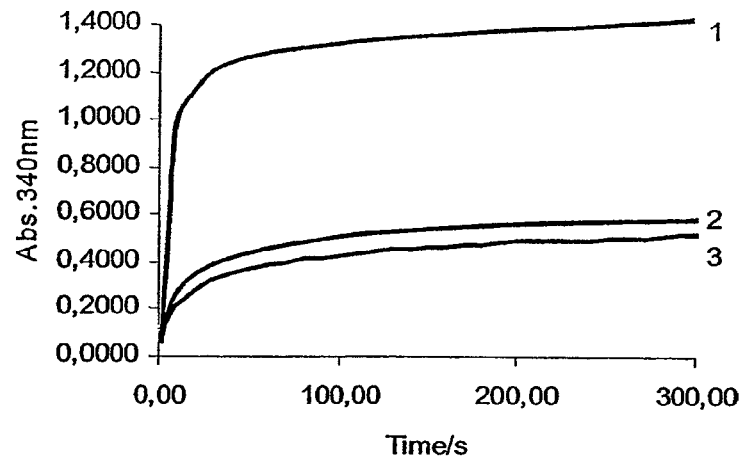
FIG. 3: Activity of N- and C-terminally double truncated tau type IIA and IIB molecules in microtubule assembly. Strong promotion of microtubule assembly in the presence of recombinant tau type IIA (1). Microtubule assembly using normal healthy tau (2) and with recombinant tau type IIB (3).

As opposed to the group IA molecules, type IIA double truncated tau derivatives were surprisingly found to promote pathological microtubule assembly (see FIG. 3 and FIG. 28C). The microtubule assembly reactions were carried out using three types of molecules: natural healthy human tau isoforms, Alz. tau type IIA (SEQ ID NO: 12) and tau type JIB (SEQ ID NO: 19). Three separate reactions were performed, each with single preparation of respective tau (healthy tau, recombinant tau type IIA or type IIB). Individual tau preparations at 0.1 mg/ml were mixed with tubulin and GTP (final concentration of tubulin is 1 mg/ml and GTP 1 mM), all reagencies in polymerisation buffer (100 mM PIPES, pH 6.9, 1 mM $MgSO_4$, 2 mM EGTA). After gentle and rapid mixing, the samples were pipetted into quartz microcuvettes and equilibrated at 37° C. in a thermostatically controlled spectrophotometer (Beckman Coulter DU640). The turbidity changes were measured at 340 nm in 10 s intervals for a period of 5 min. In this experiment, recombinant tau type IIA exhibited extremely high (threefold) promotion of pathological microtubule assembly (FIG. 3, top curve 1) as compared to physiological microtubule assembly by healthy tau (FIG. 3, curve 2). In contrast, type IIB molecules despite being N- and C-terminally double truncated are not able to perform in MAA as type IIA and promote microtubule assembly only to the level seen with healthy tau (FIG. 3, curve 3).

Example 4

Disturbed Stress Protection Mechanisms Due to Diseased Tau Type II Protein could be Demonstrated In Vitro on Neuroblastoma Cells Expressing Said Molecules Exposed to Various Kinds of Oxidative Stress In the present example, the oxidative decomposition of 3-morpholinosydnonimine (SIN-1) was used which generates superoxide anions and nitric oxide, which react and thereby form peroxynitrite. This very reactive radical can further oxidize mainly cellular membrane systems. Persons skilled in art will be able to also apply another sources of oxidative stress to neuroblastoma cells in culture and will be able to obtain the same effect here described by the use on SIN-1.

The effect of vulnerability was tested as follows:
1. SIN-1 was applied at various concentrations (0-3.32 mM) to human neuronal cell lines expressing tau type IIA protein SEQ ID NO 15 and SEQ ID NO 11, respectively.
2. The cell viability was measured by 3-(4,5-dimethylthiazol-2-yl)-2,5-diphenyltetrazolium bromide (MTT) reduction assay to determine the effective concentration of hydrogen peroxide for 50% cell viability (EC50). Persons skilled in the art are aware of different ways for evaluating the cell viability for measuring the effect that is described in the present invention.
3. The EC50 values were compared for neuroblastoma cell lines in the presence or absence of diseased tau type IIA protein expression and the statistical significance of EC50 value differences was assessed by t-test.

The cells were grown in MEM/F12 with 10% FCS, 2 mM L-Glutamine, 1% NEAA, 50 U/L gentamicine. 3-morpholinosydnonimine (SIN-1) was diluted from 1 M stock solution in serum-free medium (e.g., 47.5 mg into 230 ml). MTT stock solution (2.6 mg/ml) was prepared in MEM/F12 w/o serum and sterilized by filtration.

The cells were cultivated by the methods that are well known in the art. 96 well plates were seeded with $2 \times 10^4$ cells/well. One half of the plate was seeded with cells expressing tau type II molecules and the other half of the plate was seeded with non-expressing cells. The medium was changed every 36-48 hours.

After five day, SIN-1 was added in concentrations ranging from 0 to 3.3 mM and the plates were incubated for 24 hours. Each concentration was assayed in hexaplicate. After SIN-1 incubation, MTT stock solution was added to final concentration 200 mg/ml and the plates were incubated for another 1 hour. The medium was discarded; the surface of the plate was dried up by paper wool. 50 ml of DMSO per well were added and the plates were incubated overnight at room temperature. The absorbance at 540 nm with background correction at 690 nm was measured on ELISA reader and the background-subtracted values were used for EC50 calculation, as it is well known in the art.

The significance of differences in log EC50 concentration between neuroblastoma cells expressing type IIA protein and non-expressing said protein was tested using the t-test, the P value was for both type IIA diseased tau protein P<0.001.

Expression of tau protein SEQ ID NO: 12 and SEQ ID NO:18 decreased the resistance of neuroblastoma cells to oxidative stress by 50%.

The results of stated example (FIG. 4) contributes to an explanation of the pathogenic effect of diseased form of tau protein.

The person skilled in the art is in the position to design other test systems that combine any of the above objects of the invention. It is to be understood that all conceivable combinations fall within the scope of protection of the present invention.

Figure 4:
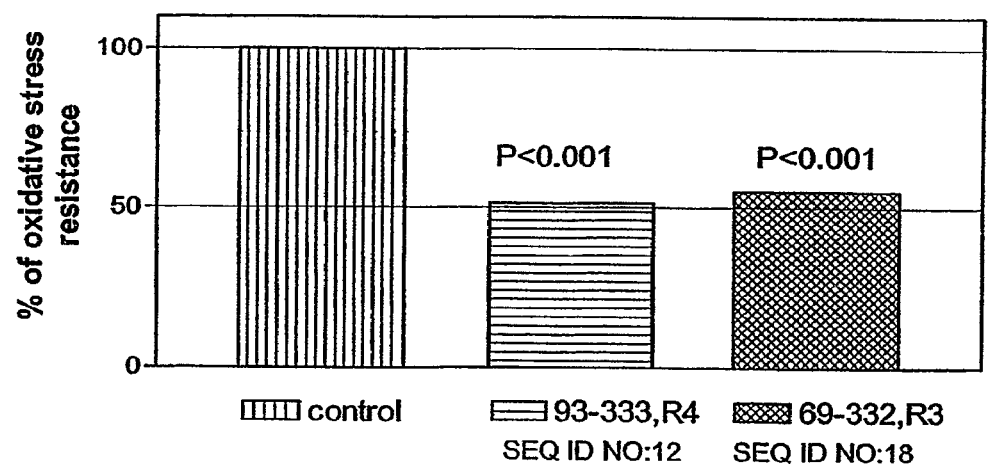
FIG. 4: Type IIA N- and C-terminally double truncated tau expressed in neuronal cells significantly increases their sensitivity to oxidative stress. The bar chart represents the decrease in relative resistance to oxidative stress of neuronal cells with the presence of tau type IIA. Resistance of cells not harboring the protein (control) is expressed as 100% (left bar) and resistance of neuronal cells expressing the diseased tau protein are shown as % of the control value (middle and right bar). Resistance is defined as the concentration of free radicals generated by SIN-1 in culture medium, where 50% of the cells die. The results represent measurement of double truncated tau proteins type IIA SEQ ID NO:12 (93-333, R4) and SEQ ID NO:18 (69-332, R3), respectively.

The chart according to FIG. 4 represents the decrease in relative resistance to oxidative stress of neuronal cells in the presence of tau type IIA. Resistance of cells non-harboring the said protein (control) is expressed as 100% (left bar) and resistance of neuronal cells expressing the diseased tau protein are shown as % of the control value (middle and right bar). Resistance is defined as the concentration of free radicals generated by SIN-1 in culture medium, where 50% of the cells die. The results represent measurement of double truncated tau proteins type IIA SEQ ID NO:12 (93-333, R4) and SEQ ID NO:18 (69-332, R3), respectively.

Example 5

Figures 5, 6:
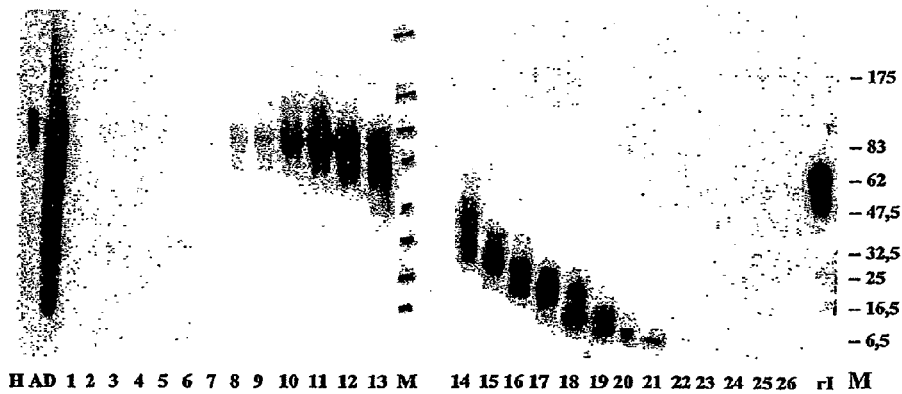
FIG. 5: Affinity of monoclonal antibody to diseased tau type IA protein and its deletion mutants. Apparent affinity of monoclonal antibody to diseased tau type IA protein and its deletion mutants. In the first column are listed: the 'prototype' tau type IA protein (SEQ ID NO 1) and respective deletion mutants. In the middle column are indicated epitopes of the present invention. Apparent affinities stated in the last column were measured by competitive ELISA, and shown as the concentrations of corresponding antigen needed for 50% competition with the prototype tau type IA protein.
FIG. 6: Fractionation of tau proteins from AD-brain on Superdex 200-columns. H: Tau from healthy brain before fractionation, AD: Tau from AD brain before fractionation, 1-26: individual fractions, rl: six isoforms of tau (recombinant, pooled), M: molecular weight markers.

Contribution of Individual Epitopes to the Conformation of Double Truncated Tau Type IA The significance of the 'conformational region' in tau type IA (segment A) or its parts was determined by sequential deletion either of whole conformation region (segment A) or its individual parts called epitopes and designated A1-A6. Since the conformation of type IA molecules strongly correlates with their function, the contribution of each epitope (A1-A6) to the overall conformation of the 'segment A' was measured on the basis of its reactivity when using a tau monoclonal antibody (FIG. 5).

The prototype tau type IA (SEQ ID NO:1) has an affinity of 10 nM. Individual deletion mutants SEQ ID NO: 22, 23, 26, with deleted epitopes A1, A2 and A5, respectively, showed that the contribution of these regions is reflected in 2-4-fold decrease in affinity (20-40 nM) whereas the deletion of epitopes A3, A4, A6 in SEQ ID NO. 24, 25 and 27, respectively, contributed to greater, 10-30-fold loss of affinity (100-300 nM). Only after deletion of the entire segment A (mutant SEQ ID NO: 21), the affinity is dramatically decreased by three orders of magnitude of the affinity of prototype tau type IA.

Example 6

Isolation of N- and C-Terminally Double Truncated Tau Type I and Type II

Preparation of Alzheimer's brain derived tau type I and type II molecules: Diseased human brain tissue from neuropathologically confirmed cases of Alzheimer's disease were used as a source for isolation of double truncated tau IA, -B and IIA proteins. Preparation of tau from Alzheimer brain is based on the combination of homogenization of tissue in TRIS buffer and fractionation of lysates by saturated ammonium sulfate precipitation. The tissue was homogenized in cold 20 mM TRIS pH 8, 0.32 mM sucrose, 10 mM b-merkaptoethanol, 5 mM EGTA, 10 mM EDTA, 5 mM $MgSO_4$, 1 mM phenylmethylsulfonyl fluoride, 50 mM sodium fluoride, 5 mM benzamidine, 5 µg/ml leupeptin, 1.5 µg/ml pepstatin, 2 µg/ml aprotinin with Heidolph DIAX 900 homogenizer for 10 min at 4° C. The homogenate was spun at 27 000 g for 30 min at 4° C. to remove cellular debris. Tau proteins were precipitated from brain tissue supernatant by adding 44.12% (v/v) of saturated ammonium sulfate. After incubation for 20 min at 25° C. and gently mixing, the sample was centrifuged at 20 000 g for 10 min at 25° C. Pellet was resuspended in 500 µl of 100 mM PIPES pH 6.9, 2 mM EGTA, 1 mM $MgSO_4$ and dialysed against the same buffer. This preparation was fractionated by gel filtration on a Superdex 200-column (Amersham-Pharmacia-Biotech) and the fractions were resolved by SDS-PAGE (gradient 5-20% polyacrylamide) and tau proteins were detected by immunoblotting according to standard procedure using anti tau antibodies DC25 (FIG. 6). The effect of individual fractions on microtubule assembly was tested.

Figure 7:
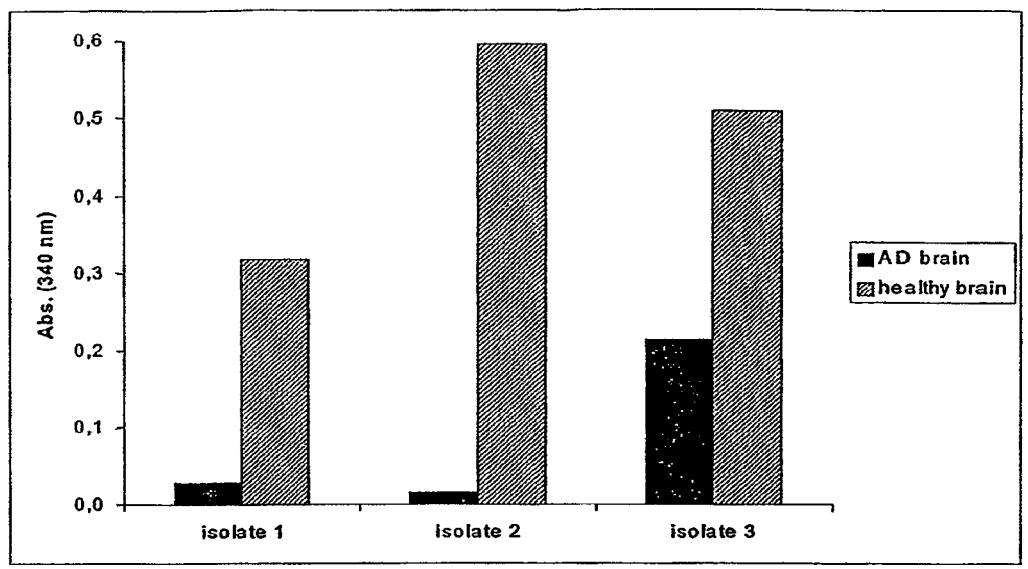
FIG. 7: Type IA inhibitory activity in fraction No. 19 from three separate isolations from AD brains. Tau preparations from fraction 19 of AD and healthy brains were mixed with normal healthy tau, tubulin and GTP at 4° C. The samples were loaded into preheated cuvettes (37°) and the changes in turbidity after 5 min. was measured using a temperature controlled spectrophotometer.
Figure 8:
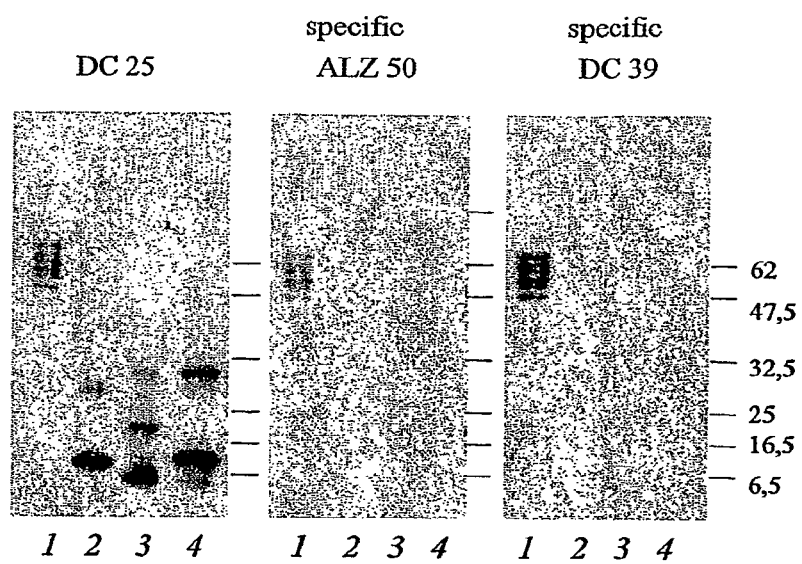
FIG. 8: Demonstration of N- and c-terminally double truncated tau type I molecules in AD brain. Demonstration of N- and C-terminally double truncated tau type I. Western blot analysis of using mABs DC25, ALZ50 and DC39. Lane 1: Recombinant six isoforms of human tau. Lanes 2-4: Three different preparations of fraction 19 from AD brain.
Figure 9:
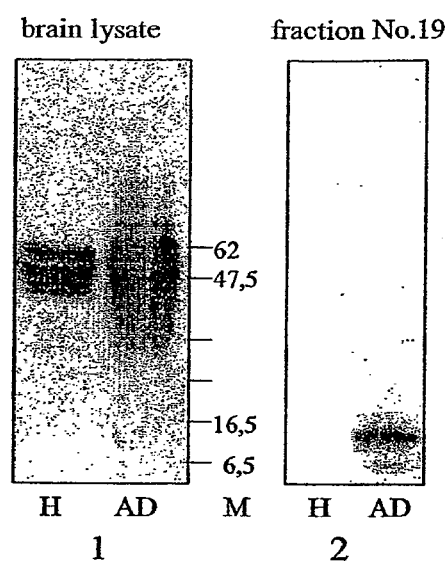
FIG. 9: Presence of tau type I in AD br Western blot using antibody DC25: Detection of tau type I in AD brain but not in healthy brain. Tau type I proteins are present in Alzheimer brain lysates (AD) and absent in normal healthy brain (H) as demonstrated by Western blot. M: molecular weight marker. Proteins resolved by SDS-PAGE were transferred to PVDF membranes and probed with antibody DC25. 1. Extracts from healthy brain (H) and Alzheimer's disease brain (AD). 2. Fraction No. 19 from healthy brain (H, does not contain type IA molecules) and Alzheimer's disease brain (AD) extracts after gel chromatography on Superdex 200 column.

Isolation of tau type IA and IB: Fraction #19 (FIG. 7) contains the tau molecules corresponding to the molecular mass of (12 kDa) representative of double truncated type IA and IB molecules—this fraction showed the highest inhibitory capacity. This fraction was characterized by Western blot analysis using three anti tau antibodies: DC25 recognizes both, truncated and full length proteins, DC39 (specific for intact C-terminus) and Alz50 (specific for intact N-terminus) (FIG. 8). The immunoreactivity of these antibodies demonstrated the lack of N- and C-terminally double truncated type I proteins only in fractions from AD-brain. Corresponding fractions prepared by the same method from normal healthy brain showed neither inhibitory activity nor specific immunoreactivity (FIG. 9). The concentration of tau proteins was determined by sandwich RIA. The total protein concentration was determined using the Bradford assay. Preparation of tau were stored at –20° C. until use.

Figure 10:
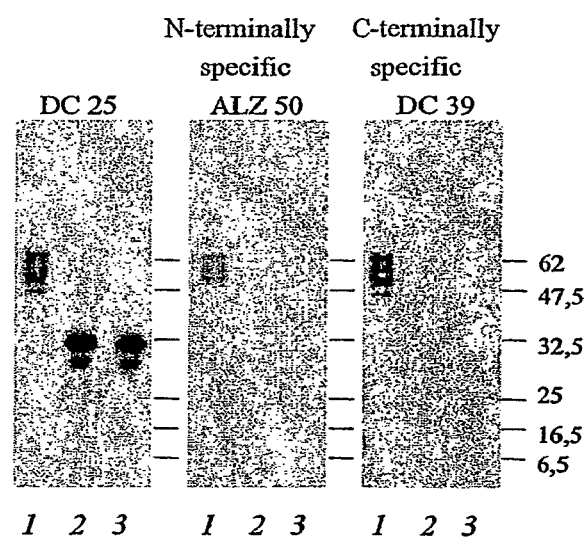
FIG. 10: Immunoreactivity of N- and C-terminally double truncated tau type II molecules. Proteins resolved by SDS PAGE (5-20% acrylamide) were transferred to PVDF membranes. Blots were probed with three different mAbs: DC25, ALZ50 and DC39. Lanes: (1). Recombinant six isoforms of human tau; (2)-(3). Two different preparation of fraction #15 from AD-brains.

Isolation of tau type IIA: Fraction #15 (FIG. 6) containing the tau molecules corresponding to the molecular mass of 30 kDa is representative of double truncated type IIA molecules. Fraction #15 showed the abnormally high microtubule assembly promoting activity. This fraction was characterized by Western blot analysis using three anti tau antibodies: DC25 recognizes both truncated and full length proteins, DC39 (specific for intact C-terminus) and Alz50 (specific for intact N-terminus) (FIG. 10). The immunoreactivity of these antibodies demonstrated the presence of N- and C-terminally double truncated type II proteins only in fractions derived from AD-brain. The concentration of tau proteins was determined by sandwich RIA. Total protein concentration was determined using the Bradford assay.

Cloning, expression and purification of recombinant tau type I and type II proteins: Genes for recombinant truncated tau proteins were derived from human cDNAs for isoforms tau43 and tau44. cDNA inserts were cloned in pET17b (Novagen) vector using NdeI-EcoRI restriction sites. (FIG. 11) (Studier et al., Meth. Enzym. 185 (1990), 60-89).

Recombinant N- and C-terminally double truncated tau molecules (SEQ ID 1-24) were prepared by PCR amplification of the relevant regions from cDNA. Specific primers introducing translation initiation start (ATG), stop (TGA) codons and NdeI, EcoRI restriction sites were used.

Figure 11:
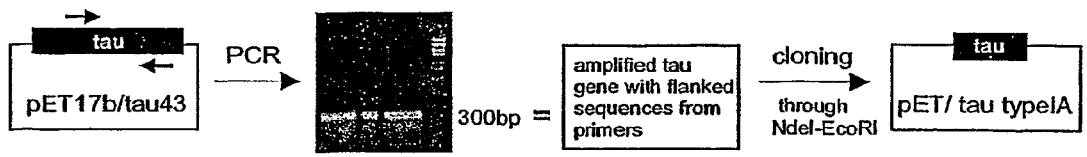
FIG. 11: Construction of recombinant tau type I-II (SEQ ID 1-24).
Figure 11:
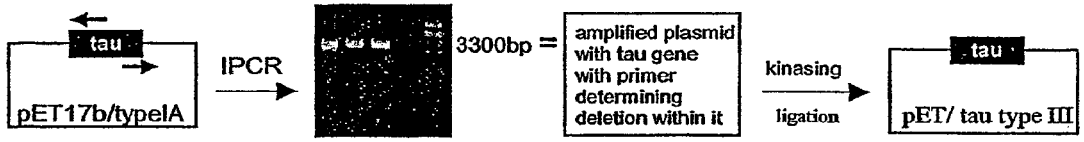

Plasmids carrying deletion of A4-A6 epitopes (SEQ ID 25-27) in the tau cDNA were generated by inverse PCR as shown in FIG. 11 (bottom panel).

Example 7

Figure 12:
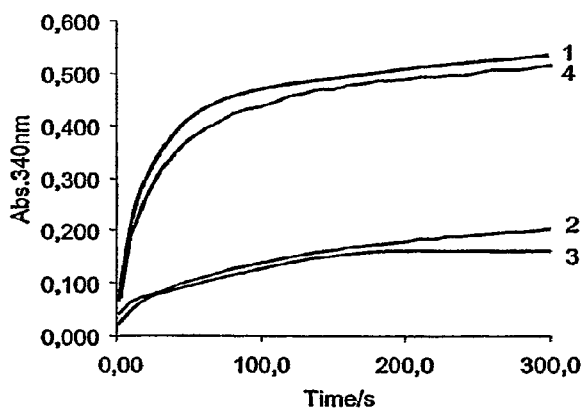
FIG. 12: Inhibitory effect of AD-brain derived and recombinant tau type IA on normal healthy tau.

Inhibitory Effect of AD-Brain Derived and Recombinant Tau Type IA on Normal Healthy Tau in Microtubule Assembly Assays AD-brain extracts as well as recombinant molecules of tau type IA are capable to inhibit microtubule assembly promotion when using natural healthy tau isoforms. For these experiments healthy human tau was isolated from brains of age matched controls and tau type IA was isolated from brains of AD patients (see Example 6, FIG. 6, fraction #19). Recombinant tau type IA (SEQ ID NO: 1) and type IB (SEQ ID NO:4, negative control) were produced and purified as shown in Example 6. In these experiments, brain-derived healthy tau isoforms (0.1 mg/ml), AD-brain derived or recombinant type IA tau or type IB (0.2 mg/ml) were mixed with tubulin. Each combination was assayed separately. The test mixtures were incubated 1 hr at 37° C. in a water bath with gently shaking. To the mixture kept on ice was added GTP and/or normal tau (final concentration of tubulin is 1 mg/ml and GTP 1 mM) all reagencies in polymerisation buffer (100 mM PIPES, pH 6.9, 1 mM $MgSO_4$, 2 mM EGTA). After gentle and rapid mixing, the samples were pipetted into quartz microcuvettes and equilibrated at 37° C. in a thermostatically controlled spectrophotometer (Beckman Coulter DU640). The turbidity changes were measured at 340 nm in 10 s intervals for a period of 5 min. Data show that both AD brain derived as well as recombinant double truncated type IA molecules inhibit the capacity of normal tau to promote microtubule assembly (FIG. 12, curve 2,3). In contrast, recombinant type IB is not able to inhibit the tubulin polymerization promoting capacity of induced by normal human tau (FIG. 12, curve 4). Curve 1 (FIG. 12) represents microtubule assembly promoted by normal tau.

Example 8

Screening Assay for Drug Candidates Neutralizing Pathological Activity of Tau Type I A Using the capacity of double truncated tau type IA molecules to inhibit activity of healthy normal tau to promote tubulin polymerization, a screening assay was designed for selection of compounds capable of neutralizing the inhibitory activity of type IA molecules. Diseased tau type IA can be derived from AD-brains or recombinant sources, however it is expedient to use recombinant material. The neutralizing effect of drug candidate can be defined quantitatively by measuring residual capacity of normal healthy tau to promote microtubule assembly. The assay is performed in two steps:

1. Screening for Drug Candidates Neutralizing Tau Type I A.

Figure 13:
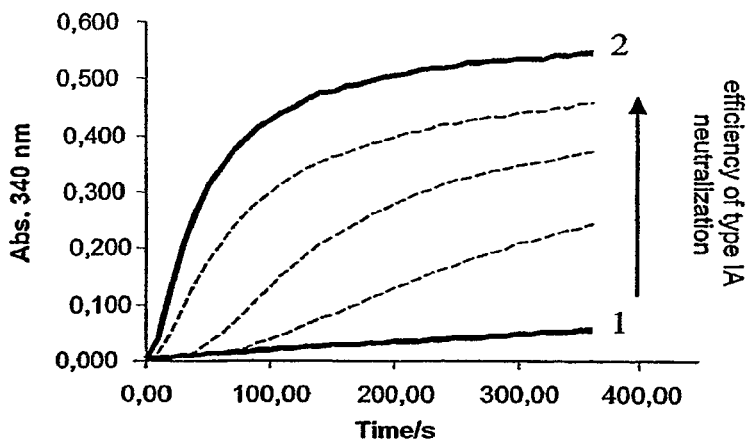
FIG. 13: First round screening for drug candidates neutralizing tau type IA molecules (step 1). A drug candidate was preincubated with type IA molecule and efficiency of type IA neutralization was assayed in microtubule assembly. Bottom curve 1 and top curve 2 represent negative (no neutralization) and positive (100%) neutralizing activity of tested drug candidate against diseased type IA molecules. Middle curves indicate various efficiencies of type IA-neutralization by three different drug candidates.

Prototype recombinant type IA molecules (SEQ. ID NO: 1) (final concentration 100 mg/ml) mixed separately with individual drug candidates (final concentration 50 mg/ml) were preincubated for 1 hr/37° C. Following incubation, tubulin, GTP and healthy tau were added to the mixture (the final concentration: tubulin—1 mg/ml, GTP—1 mM, healthy tau—100 mg/ml) at +4° C. After rapid mixing, the samples were loaded into quartz microcuvettes and equilibrated at 37° C. in a thermostatically controlled spectrophotometer. The turbidity changes were measured at 340 nm. Drug candidates with capacity to neutralize type IA-activity were selected by measuring residual microtubule assembly promoting potential of normal healthy tau (FIG. 13; a drug candidate was preincubated with type IA molecule and efficiency of type IA neutralization was assayed in microtubule assembly. Bottom curve 1 and top curve 2 represent negative (no neutralization) and positive (100%) neutralizing activity of tested drug candidate against diseased type IA molecules. Middle curves indicate various efficiencies of type IA-neutralization by three different drug candidates). It is obvious that the threshold for selection of positive drugs is arbitrary and may vary from total neutralization of type IA to partial neutralization of thereof.

Figure 14:
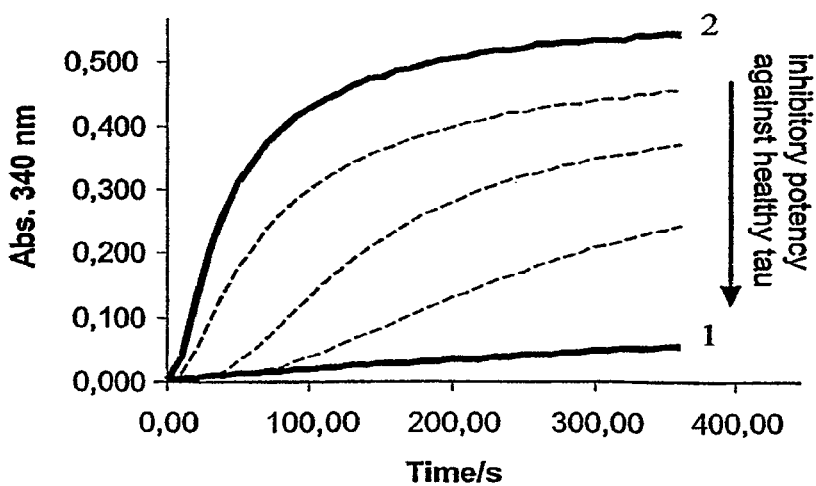
FIG. 14: Second round screening for drug candidates neutralizing type IA molecules with selectivity against normal tau (step 2). Drug candidates selected in step 1 were preincubated with healthy tau and the effect on microtubule assembly was assayed. The bottom curve (1) shows inactivation of healthy tau thus no selectivity. The top curve (2) shows no inhibition of healthy tau, thus high specificity for the diseased forms. The middle curves show drug candidates with various levels of specificity against healthy tau.

2. Selection of drug candidates neutralizing type IA molecules and discriminating them from normal healthy tau. Selected candidates with neutralizing activity against tau type IA molecules were screened for reactivity with normal healthy tau to select molecules specific only for type IA. Separate mixtures of normal healthy tau (final concentration 100 mg/ml) with individual drug candidates (final concentration 50 mg/ml) were preincubated 1 hr/37° C. After incubation tubulin and GTP were added to the mixtures (the final concentration: tubulin 1 mg/ml, GTP—1 mM) at +4° C. Following rapid mixing, the samples were loaded into quartz microcuvettes. Turbidity changes were measured at 340 nm. Those drug candidates were selected which showed no interference with the MT polymerization promoting activity of healthy tau (FIG. 14).

Example 9

Screening Assay for Drug Candidates Neutralizing Pathological Activity of Tau Type IIA The present invention shows that tau type IIA molecules have unexpectedly high potency to promote tubulin polymerization forms a basis for a screening assay for selection of compounds neutralizing said activity of type IIA proteins. The neutralization of type IIA can be quantified by measuring residual microtubule assembly activity of type IIA molecules. The assay is performed in two steps:

1. Screening for Therapeutic Drug Candidates Neutralizing Tau Type IIA.

Figure 15:
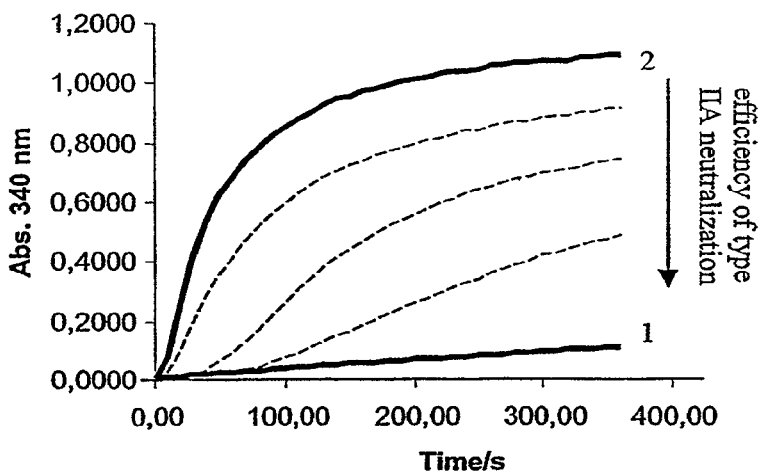
FIG. 15: First round screening for drug candidates neutralizing tau type IIA. Drug candidate was preincubated with type IIA molecule and efficiency of type IIA neautralization was assayed in microtubule assembly. Bottom curve 1 represents positive (100%) neutralizing activity of respective drug candidate and top curve 2 indicates no neutralization of diseased type IIA molecules. Middle curves indicate different efficiency of various drug candidates in type IIA-neutralization.

The separate mixtures of tau type IIA (SEQ ID NO:12) (final concentration 100 mg/ml) with single drug candidates (final concentration 50 mg/ml) were preincubated for 1 hr/37° C. Following incubation tubulin and GTP were added to the mixtures (the final concentration: tubulin 1 mg/ml, GTP—1 mM) at +4° C. After rapid mixing, the samples were pipetted into quartz microcuvettes and equilibrated at 37° C. in a thermostatically controlled spectrophotometer. The turbidity changes were measured at 340 nm. Drug candidates which significantly decreased microtubule assembly rate were selected for second step of the assay (FIG. 15; drug candidate was preincubated with type IIA molecule and efficiency of type IIA neutralization was assayed in microtubule assembly. Bottom curve 1 represents positive (100%) neutralizing activity of respective drug candidate and top curve 2 indicates no neutralization of diseased type IIA molecules. Middle curves indicate different efficiency of various drug candidates in type IIA-neutralization).

2. Selection of Drug Candidates Neutralizing Type IIA Molecules and Discriminating them from Normal Healthy Tau.

Separate mixtures of drug candidates (final concentration 50 mg/ml) with normal healthy tau (final concentration 100 mg/ml) were preincubated for 1 hr/37° C. Then tubulin and GTP were added to the mixtures (the final concentration: tubulin 1 mg/ml, GTP—1 mM) at +4° C. After rapid mixing, the samples were pipetted into quartz microcuvettes and equilibrated at 37° C. in a thermostatically controlled spectrophotometer. The turbidity changes were measured at 340 nm. Drug candidates with no interference with healthy tau were selected (FIG. 16; drug candidates selected in step 1 were preincubated with healthy tau and the effect on microtubule assembly was assayed. The bottom curve (1) represents maximal inhibition of healthy tau and the top curve (2) indicates no inhibition of healthy tau. Middle curves show drug candidates with different inhibitory activity against healthy tau).

Example 10

Preparation of Monoclonal Antibodies Neutralizing N- and C-Terminally Double Truncated Type IA and Type IIA Molecules Immunization protocol and fusion procedure: N- and C-terminally double truncated tau type I proteins isolated from human Alzheimer brains (Fraction #19, Example 6) were used as a immunogen. Balb/c mice were primed subcutaneously with said proteins (50 mg/mouse) in complete Freund's adjuvant and boosted intraperitoneally 3 times thereafter at 4-week intervals with the 50 mg/mouse of the same proteins. Prefusion sera were collected and the level of specific antibodies against tau were tested by ELISA (FIG. 17; the levels of specific antibodies in sera of mice immunized with AD derived tau were tested in ELISA on the same antigen. All five sera showed high anti-tau binding activity to said tau protein. FIG. 17 represents levels of specific antibodies in one of the immunized mice. As a control was used serum from the mouse immunized with irrelevant protein). Mouse spleen cells were fused with NS/0 myeloma cells, using a modified procedure well known in the art (M. Kohler and C. Milstein, 1975).

According to the results shown in FIG. 18, monoclonal antibodies DC44, DC82 and DC136 recognize N- and C-terminally double truncated type IA and type IIA molecules from Alzheimer brain. For these antibodies no reactivity was observed with tau isolates from normal human brain prepared by the same method (FIG. 18) By contrast, monoclonal antibody DC25 reacts in ELISA with the said proteins from pathological as well as from normal healthy brain (FIG. 18). This antibody does not discriminate between pathological form (AD-tau) of tau and normal human tau.

After this primary screening, hybridomas were subcloned in soft agarose, a technique well-know to those skilled in the art, finally resulting in homogenous hybridoma populations secreting antibodies with an identical idiotype.

These cloned hybridomas clones were further checked for reactivity to recombinant full length tau isoforms and double truncated tau type IA (SEQ ID NO: 1) and type IIA (SEQ ID NO: 12) molecules, in ELISA identical to the screening assay.

Example 11

Neutralization of the Pathological Activity of AD-Brain Derived and Recombinant N- and C-Terminally Truncated Type IA Molecules Using Monoclonal Antibodies Selected monoclonal antibodies DC44, DC82, DC136 and DC25 were further characterized for their ability to neutralize the activity of native tau type IA isolated from Alzheimer brain (see Example 6). Said tau isolate (final concentration of 100 mg/ml) and tested antibodies (final concentration 50 mg/ml) were preincubated for 1 hr/37° C. After incubation tubulin, normal human tau and GTP were added to the mixture (the final concentration: tubulin 1 mg/ml, healthy human tau—100 mg/ml, GTP—1 mM) at +4° C. After rapid mixing the samples were pipetted into quartz microcuvettes and equilibrated at 37° C. in a thermostatically controlled spectrophotometer. The turbidity changes were measured at 340 nm. Monoclonal antibodies DC136, DC44 and DC82 were able to inhibit the pathological activity of said protein (FIG. 20; antibodies were preincubated with native tau type IA (fraction #19) and subsequently mixed with healthy human tau, tubulin and GTP. The formation of microtubules was determined spectrophotometrically after 5 min at 370° C. The bars represent a mean value of three independent experiments. MAA-microtubule assembly assay with healthy human tau. MAIA-microtubule assembly inhibition assay with healthy human tau preincubated with tau type IA (without antibody)). In an analogous experiment, antibodies were tested with the recombinant prototype of tau type IA (SEQ ID NO: 1), showing a similar pattern of neutralizing activity (FIG. 21). Control antibody DC25 recognizes all forms of truncated and normal tau tested by ELISA and Western blotting however does not interfere with AD-brain derived type IA activity in microtubule assembly assays. These results suggest that antibody DC25 reacts with the distinct region of tau comparing to the antibodies DC136, DC44 and DC82. In contrast, antibodies DC136, DC44 and DC82 bind epitope(s) involved in pathological of type IA molecules.

The next selection step was aimed at antibodies capable to discriminate between normal healthy and type IA molecules. Mixtures of normal healthy tau (final concentration 100 mg/ml) and tested antibody (final concentration 50 mg/ml) were preincubated 1 hr/37° C. After incubation tubulin and GTP were added to the mixture (the final concentration: tubulin 1 mg/ml, GTP—1 mM) at +4° C. Following rapid mixing, the samples were pipetted into quartz microcuvettes and equilibrated at 37° C. in a thermostatically controlled spectrophotometer. The turbidity changes were measured at 340 nm. None of antibodies DC136, DC44, DC82 and DC25 was able to inhibit normal healthy tau in microtubule assembly (FIG. 22; antibodies neutralizing tau type IA were preincubated with healthy tau and subsequently mixed with tubulin and GTP. The formation of microtubules was determined spectrophotometrically after 5 min at 370° C. The bars show the mean value of three independent experiments. MAA-microtubule assembly assay with healthy tau. As a negative control an antibody neutralizing healthy tau was used). The present data demonstrated that antibodies DC136, DC44, DC82 recognize specific epitope(s) involved in interaction of truncated diseased forms of tau with healthy tau proteins.

Example 12

Neutralization of Type IIA Activity by Monoclonal Antibodies

Antibodies previously isolated for their tau type IA neutralizing activity were tested for their neutralizing activity against recombinant tau type IIA (SEQ ID NO:12) using the method described in Example 8B. All three neutralizing monoclonal antibodies DC44, DC82 and DC136 were able to reduce the pathological activity of N- and C-terminally double truncated tau type IIA molecules (FIG. 23; antibodies were preincubated with recombinant tau type IIA and then mixed with tubulin and GTP. The formation of microtubules was determined spectrophotometrically after 5 min at 37° C. The bars represent the mean value of three independent experiments. MAA-microtubule assembly assay with tau type IIA (without antibody)). This suggests that the epitope(s) of said antibodies is shared at least by type I A SEQ ID NO:1 and type II A SEQ ID NO:12. For antibody DC25 no type IIA-inhibitory activity was observed.

Example 13

Immunogenicity of Recombinant N- and C-Terminally Double Truncated Tau Type IA and IIA Molecules Immunization protocol: In a preferred embodiment of the invention, said recombinant tau type IA and IIA proteins are used for vaccination purposes or for raising antibodies which specifically neutralize the pathogenic activity of diseased tau type IA and IIA molecules. In the given example recombinant N- and C-terminally double truncated tau type IIA (SEQ ID NO: 12) was used as an immunogen. Balb/c mice were primed subcutaneously with said proteins (50 mg/mouse) in complete Freund's adjuvant and boosted intraperitoneally 3 times thereafter at 4-week intervals with the 50 mg/mouse of the same proteins in incomplete Freund's adjuvant. Immune sera were collected and the level of specific antibodies against respective recombinant antigens tau were determined by ELISA (FIG. 24).

Example 14

Transgenic Animals

DNA extracted from tail tips: Genomic DNA was extracted by DNeasy tissue kit, Qiagen.

Genotyping (FIG. 25): Specific amplification of transgenes encoding double truncated tau forms was performed on genomic DNA derived from the parental generation of transgenic animals and is shown in FIG. 25A. Further analysis of genomic DNA of the F1 generation revealed that transgenes are heritable since they were also identified in the offspring of parental generation. Transgenes encoding double truncated tau are therefore fixed in chromosomal DNA of the animals (FIG. 25B—Genotyping of F1 generation). The animals used in this example are of a specific genetic background characterized by spontaneous hypertension and other Alzheimer's disease associated risk factors, such as dyslipidaemia or diabetes. This animal strain therefore represents a unique experimental Alzheimer model by combining the most frequently occurring Alzheimer's disease risk factors such as hypertension and diabetes.

For transgene generation, standard techniques of molecular biology were used as described in Sambrook et al., Molecular Cloning A Laboratory Manual, CSH Laboratory, New York (2001). cDNA encoding double truncated tau was introduced into an expression vector linked to a promoter directing an expression in ubiquitous or tissue specific manner. The gene fragment was introduced into one day embryos via pronuclear injection (non limited). Resulting offspring was genotyped using genomic DNA from the tail tip.

Analysis of transgene expression (FIG. 26): Expression of mRNA derived from the transgenes were assessed by RT-PCR analysis, applying generally known methods such as RT-PCR and agarose gel electrophoresis.

Panel A of FIG. 25 shows genotyping of the parental generation of transgenic animals. Specific amplification of double truncated sequence of DNA from genomic DNA in lanes 1, 2, 3 and 4 indicates the presence of a specific transgene in genomic DNA extracted from tails of the progeny of foster mothers. These animals represent the parental generation of transgenic animals bearing double truncated type IIA tau molecules. In this example, positive (+C) and negative (−C) and two additional negative samples (5, 6) are shown (M=size marker). The arrow indicates the expected PCR product size expected in transgene positive animals.

Panel B of FIG. 25: Genotyping of animals from F1 generation. Genomic DNA was extracted from tail tips and double truncated tau specific DNA sequence was identified and are shown in lanes 1. Lane 2 and 3 show negative controls. Identification of a tau specific DNA fragment in the F1 generation confirms the inheritability of these transgenes.

FIG. 26: RNA was extracted from flash frozen tissue of transgenic animals and subjected to reverse transcription followed by specific amplification of the cDNA. An example shows transgene expressing animals in lanes number 1 and 2. Lanes 3-5 represent non-expressing controls while lane 5 shows a non-specific signal typically emerging in non-transgenic animal when using this method. This example indicates the presence of double truncated tau specific mRNA expressed from the transgene in experimental animals.

Example 15

A: Overexpression of type IIA molecules causes cell death in differentiated neuron-like cells.

In neuroblastoma cell line SH-SY5Y, cell death caused by type IIA molecule was demonstrated using standardized in vitro differentiation conditions known to the person skilled in the art. The effect was tested in stably transfected cells expressing type IIA double truncated tau and compared with non-transfected cells. Cell viability was quantified manually using a trypan blue exclusion assay in triplicates and statistical evaluation was performed using the One-way ANOVA test. Significant differences in cell viability between cells overexpressing type IIA double truncated tau and wild type cells were found after 6 day of in vitro differentiation (P<0.001). The over-production of type IIA double truncated tau (0.5% of the total protein amount) caused a 3×-decreased viability rate of the cells (FIG. 27; comparison of the cell viability of SY5Y cells transfected with double truncated tau type IIA (type IIA) and non-transfected control neuron-like cells (mock), respectively).

In analogy to the previously shown constructions a similar system has been established using constructs encoding for double truncated type I molecules.

Type II double truncated tau molecules show increased binding affinity to the microtubular system.

Isolation of free tau fractions (FT), microtubule associated fractions (MT) and nuclear fractions (NAT) from stably transfected SH-SY5Y cells expressing type IIA double truncated tau and full length tau was performed. Quantification of tau association with microtubules showed an increased affinity of double truncated type IIA tau to microtubules (more than 50%) in comparison with the full-length form (FIG. 28A; increased binding affinity of type IIA molecules to microtubules is demonstrated by using cellular fractionation of stably transfected cells expressing type IIA double truncated molecules and full-length tau. Isolation of free tau (FT), microtubule bound tau (MT) and nucleus associated tau (NAT) was performed as described). The amount of tau was quantified according to standard cell biological fractionation methods used in the art followed by Western blot analysis. Calibration curves were calculated using recombinant tau protein with defined amounts.

B: Organic substance F123 $[C_{34-59}O_{14-23}H_{32-44}N_{6-8}]_n$ is analysed with respect to its inhibitory effect in a microtubule polymerisation assay:
(1) Incubation of F123 with tau (normal tau and tau type IA'; conc=100 µg/ml; tau type IIA conc=60 µg/ml) for 1 h at 37° C.
(2) addition of tubulin (conc=1 mg/ml)
(3) measurement of 340 nm/5 min (remark: all dilution with PIPES buffer C: Normal healthy tau and Alzheimer tau type II are analysed with respect to their microtubule assembly promotion capacity. Normal tau in this example represented by tau 43 forms typical microtubules shown in electron microscopy (see FIG. 28C). However, Alzheimer tau type II produces pathological microtubules with typical pattern (see FIG. 28C).

Example 16

Functional Consequences of N- and C-Terminally Double Truncated Tau Type II Overexpression in Eukaryotic Cells The pathological phenotype showing altered transport of mitochondria caused by over-expression of a type IIA molecules was performed in the neuroblastoma cell line SH-SY5Y. The influence of the N- and C-terminally double truncated tau type II molecules was examined by comparing mitochondrial redistribution in living wild type SH-SY5Y cells with transfected cells. Cell biological transport assays known to the person skilled in the art were used. In brief, cells were cultivated on LabTekII chambers (Nunc) with equal density (70% confluent) according to standard laboratory techniques and transfection was performed using Fugene 6 (Roche) according to the instructions of the manufacturer. Staining of mitochondria (MitoFluor Red 594, Molecular Probes) was performed following the instructions of the manufacturer. Living cells were examined with an Axiovert 200M fluorescence microscope (ZEISS) equipped with an 63× oil-immersion objective and fluorescence filters. Pictures were taken with a CCD camera (Photometrics, Cool snap HQ; Hamamatsu) in combination with the software program MetaMorph (Universal Imaging).

Using the mitochondria-specific dye MitoFluor (Molecular Probes), mitochondrial localization was compared in induced and non-induced SH-SY5Y cells. The staining confirmed the negative effect of type IIA double truncated tau molecules on mitochondrial transport in SH-SY5Y cells resulting in perinuclear mitochondrial clustering near the centrosome indicative of a functional dominance of the minus end directed intracellular forces (FIG. 30).

As a control, logarithmically growing cells (FIG. 29) reveal a regular distribution of mitochondria in the cell body as well as in the cell periphery. In conclusion, the N- and C-terminally double truncated type IIA proteins are therefore able to influence intracellular transport mechanism which affect mitochondrial redistribution. The present experimental setting shows a suitable method for testing inhibitory activities directed against type IIA molecules.

REFERENCES

1. Finch C, Tanzi R E, (1997) Science 278, 407-411
2. Blessed G, Tomlinson B E, Roth M (1968 Br J Psychiatry 114: 797-811
3. Tomlinson B E, Blessed G, Roth M J, (1970) Neurol Sci 11, 205-242
4. Arigada P A, Growdon J H, Hedley-White E T, Hyman B T (1992) Neurology 42, 631-639
5. Wischik C M, Novak M, Edwards P C, Klug A, Tichelaar W, Crowther R A (1988a) Proc Natl Acad Sci USA 85: 4884-4888
6. Wischik C M, Novak M, Trogersen H C, Edwards P C, Runswick M J, Jake R, Walker J E, Milstein C, Roth M, Klug A (1988b) Proc Natl Acad USA 85: 4506-4510
7. Himmler A, Drechsel D, Kirschner M W, Martin D W jr, (1989) Mol Cell Biol 9, 1381-1388
8. Goedert M, Spillantini M G, Jakes R, Rutherford D., Crowther R A (1989) Neuron #, 519-526
9. Hutton M, Lendon C L, Rizzu P, Baker M, Froelich S., Houlden H, Pickering-Brown S, Chackraverty S, Isaacs A, Grover A (1998) Nature 393, 702-705
10. Spillantini N G, Murrell J R, Goedert M, Farlow M R, Klug A, Ghetti B (1998) Proc Natl Acad Sci USA 95, 7737-7741.
11. Selkoe D J, (1999) Nature 399, A23-31
12. Isacson O, Seo H, Lin L, Albeck D, Granholm A C H, (2002) Trends Neurosci 25, 79-84
13. Mudher A, Lovestone S, (2002) Trends Neurosci 25, 22-26
14. Couzin J, (2002) Science 296, 28-29
15. Grundke-Iqbal I, Iqbal K, Tung Y-C, Quinlan M, Wisniewski H M, Binder L I, (1986) Proc Natl Acad Sci USA, 83, 4913-4917
16. Gustke N, Steiner B, Mandelkow E M, Biernat J, Meyer H E, Goedert M, Mandelkow E (1992) FEBS Lett 307, 199-205
17. Lindwall G, Cole R D (1984) J Biol Chem 259, 12241-12245
18. Kopke E, Tung Y-Ch, Shaikh S, Alonso A C, Iqbal K, Grundke-Iqbal I (1993) J Biol Chem 268, 24374-24384
19. Cleveland D W, Hwo S Y, Kirschner M W (1977a) J Mol Biol 116: 227-247
20. Cleveland D W, Hwo S Y, Kirschner M W (1977b) J Mol Biol 116: 207-225
21. Lee M Y, Balin B J, Otvos L, Trojanowski J Q (1991) Science 251, 675-678
22. Alonso A C, Zaidi T, Grundke-Iqbal I, Iqbal K (1994) Proc Natl Acad Sci USA 91:5562-5566
23. Wille H, Mandelkow E M, Mandelkow E (1992) J Biol Chem 267:10737-10742
24. Alonso A C, Grundke-Iqbal I, Iqbal K (1996) Nat Med 2:783-787
25. von Bergen M, Barghorn S, Li L, Marx A, Biernat J, Mandelkow E M, Mandelkow E (2001) J Biol Chem 276:48165-48174
26. Friedhoff P, von Bergen M, Mandelkow E M, Mandelkow E (2000) Biochim Biophys Acta 1502:122-132 Review
27. Illenberger S, Zheng-Fischhofer Q, Preuss U, Stamer K, Baumann K, Trinczek B, Biernat J, Godemann R, Mandelkow E M, Mandelkow E (1998) Mol Biol Cell 9:1495-1512
28. Kampers T, Friedhoff P, Biernat J, Mandelkow E M, Mandelkow E (1996) FEBS Lett 399: 344-349
29. Perez M, Valpuesta J M, Medina M, Montejo de Garcini E, Avila J (1996) J Neurochem 67: 1183-1190
30. Wang J-Z; Grundke-Iqbal I; Iqbal K (1996) Nature Med 2: 871-875
31. Wilson D M, Binder L I (1997) Am J Pathol 150: 2181-2195
32. Schweers O, Mandelkow E M, Biernat J, Mandelkow E (1995) Proc Natl Acad Sci USA 92: 8463-8467
33. Ksiezak-Reding H, Yang G, Simon M, Wall J S (1998) Brain Res. 814: 86-98
34. Schneider A, Biernat J, Von Bergen M, Mandelkow E, Mandelkow E M (1999) Biochemistry 38: 3549-3558
35. Yan S-D, Chen X, Schmid A-M, Brett J, Godman G, Zou Y-S, Scott C W, Caputo C, Frappier T, Smith M A, Perry G, Yen S H, Stern D (1994) Proc Natl Acad Sci USA 91: 7787-7791
36. Smith M A, Taneda S, Richey P L, Miyata S, Yan S D, Stern D, Sayre L M, Monnier V M, Perry G (1994) Proc Natl Acad Sci USA 91:5710-5714
37. Mori H, Kondo J, Ihara Y (1987) Science 235: 1641-1644
38. Paudel H, Li W (1999). J Biol Chem 274: 8029-8038
39. Goedert M, Spillantini M G, Potier M C, Ulrich J, Crowther R A, (1989) EMBO J. 8, 393
40. Goedert M, Spillantini M G, Jakes R, Rutherford D, Crowther R A (1989) Neuron 4, 519
41. Crowther R A, Olesen O F, Jakes R, Goedert M (1992) FEBS Lett 309:199-202
42. Crowther R A, Olesen O F, Smith M J, Jakes R, Goedert M (1994) FEBS Letter 337: 135-138
43. (see e.g. M. Kohler and C. Milstein, in "Continuous Cultures of Fused Cells Secreting Antibody of Pre-Defined Specificity", Nature, 256, pp. 495-497, 1975; and Harlow and Lane, in "Antibodies, A Laboratory Manual", Cold Spring Harbor Laboratory, Cold Spring Harbor, 1988)

The invention claimed is:

1. An isolated recombinant cell genetically modified with a vector, wherein the vector comprises a cDNA encoding a fragment of the human tau43 molecule of SEQ ID NO:35 functionally linked to a promoter, and wherein the amino acid sequence of the fragment of tau43 consists of SEQ ID NO:13, SEQ ID NO:14, or a subsequence of SEQ ID NO:35 that comprises at least SEQ ID NO:11 or SEQ ID NO:12, does not extend N-terminally beyond amino acid residue 68 of SEQ ID NO:35, and does not extend C-terminally into the last 40 amino acids of SEQ ID NO:35.

2. The isolated recombinant cell of claim 1, wherein the cell is a oocyte or a prokaryotic cell.

3. The isolated recombinant cell of claim 1, wherein the cell is a neuroblastoma cell, a pheochromocytoma cell, or a cell from a primary culture of nerve cells.

4. The isolated recombinant cell of claim 1, wherein the promoter is chosen from a ubiquitous promoter and a tissue-specific promoter.

5. The isolated recombinant cell of any one of claims 1-4, wherein the amino acid sequence of the fragment is selected from SEQ ID NO:11, 12, 13, and 14.

6. An isolated recombinant cell genetically modified with a vector, wherein the vector comprises a cDNA encoding a fragment of the human tau44 molecule of SEQ ID NO:36 functionally linked to a promoter, and wherein
the amino acid sequence of the fragment of tau44 consists of a subsequence of SEQ ID NO:36 that comprises at least SEQ ID NO:15, 16, 17, or 18, does not extend N-terminally beyond amino acid residue 68 of SEQ ID NO:36, and does not extend C-terminally into the last 20 amino acids of SEQ ID NO:36.

7. The isolated recombinant cell of claim 6, wherein the cell is a oocyte or a prokaryotic cell.

8. The isolated recombinant cell of claim 6, wherein the cell is a neuroblastoma cell, a pheochromocytoma cell, or a cell from a primary culture of nerve cells.

9. The isolated recombinant cell of claim 6, wherein the promoter is chosen from a ubiquitous promoter and a tissue-specific promoter.

10. The isolated recombinant cell of any one of claims 6-9, wherein the amino acid sequence of the fragment is selected from SEQ ID NO: 15, 16, 17, and 18.

* * * * *

SEQUENCE LISTING

```
<160> NUMBER OF SEQ ID NOS: 36

<210> SEQ ID NO 1
<211> LENGTH: 95
<212> TYPE: PRT
<213> ORGANISM: Homo sapiens

<400> SEQUENCE: 1

Ile Lys His Val Pro Gly Gly Gly Ser Val Gln Ile Val Tyr Lys Pro
```

```
                1               5                  10                  15
Val Asp Leu Ser Lys Val Thr Ser Lys Cys Gly Ser Leu Gly Asn Ile
            20                  25                  30

His His Lys Pro Gly Gly Gly Gln Val Glu Val Lys Ser Glu Lys Leu
            35                  40                  45

Asp Phe Lys Asp Arg Val Gln Ser Lys Ile Gly Ser Leu Asp Asn Ile
            50                  55                  60

Thr His Val Pro Gly Gly Gly Asn Lys Lys Ile Glu Thr His Lys Leu
65                  70                  75                  80

Thr Phe Arg Glu Asn Ala Lys Ala Lys Thr Asp His Gly Ala Glu
                85                  90                  95

<210> SEQ ID NO 2
<211> LENGTH: 97
<212> TYPE: PRT
<213> ORGANISM: Homo sapiens

<400> SEQUENCE: 2

Asp Asn Ile Lys His Val Pro Gly Gly Gly Ser Val Gln Ile Val Tyr
1               5                  10                  15

Lys Pro Val Asp Leu Ser Lys Val Thr Ser Lys Cys Gly Ser Leu Gly
            20                  25                  30

Asn Ile His His Lys Pro Gly Gly Gly Gln Val Glu Val Lys Ser Glu
            35                  40                  45

Lys Leu Asp Phe Lys Asp Arg Val Gln Ser Lys Ile Gly Ser Leu Asp
            50                  55                  60

Asn Ile Thr His Val Pro Gly Gly Gly Asn Lys Lys Ile Glu Thr His
65                  70                  75                  80

Lys Leu Thr Phe Arg Glu Asn Ala Lys Ala Lys Thr Asp His Gly Ala
                85                  90                  95

Glu

<210> SEQ ID NO 3
<211> LENGTH: 80
<212> TYPE: PRT
<213> ORGANISM: Homo sapiens

<400> SEQUENCE: 3

Ile Lys His Val Pro Gly Gly Gly Ser Val Gln Ile Val Tyr Lys Pro
1               5                  10                  15

Val Asp Leu Ser Lys Val Thr Ser Lys Cys Gly Ser Leu Gly Asn Ile
            20                  25                  30

His His Lys Pro Gly Gly Gly Gln Val Glu Val Lys Ser Glu Lys Leu
            35                  40                  45

Asp Phe Lys Asp Arg Val Gln Ser Lys Ile Gly Ser Leu Asp Asn Ile
            50                  55                  60

Thr His Val Pro Gly Gly Gly Asn Lys Lys Ile Glu Thr His Lys Leu
65                  70                  75                  80

<210> SEQ ID NO 4
<211> LENGTH: 88
<212> TYPE: PRT
<213> ORGANISM: Homo sapiens

<400> SEQUENCE: 4

Ile Lys His Val Pro Gly Gly Gly Ser Val Gln Ile Val Tyr Lys Pro
1               5                  10                  15
```

```
Val Asp Leu Ser Lys Val Thr Ser Lys Cys Gly Ser Leu Gly Asn Ile
            20                  25                  30

His His Lys Pro Gly Gly Gly Gln Val Glu Val Lys Ser Glu Lys Leu
        35                  40                  45

Asp Phe Lys Asp Arg Val Gln Ser Lys Ile Gly Ser Leu Asp Asn Ile
    50                  55                  60

Thr His Val Pro Gly Gly Gly Asn Lys Lys Ile Glu Thr His Lys Leu
65                  70                  75                  80

Thr Phe Arg Glu Asn Ala Lys Ala
                85

<210> SEQ ID NO 5
<211> LENGTH: 90
<212> TYPE: PRT
<213> ORGANISM: Homo sapiens

<400> SEQUENCE: 5

Ile Lys His Val Pro Gly Gly Gly Ser Val Gln Ile Val Tyr Lys Pro
1               5                   10                  15

Val Asp Leu Ser Lys Val Thr Ser Lys Cys Gly Ser Leu Gly Asn Ile
            20                  25                  30

His His Lys Pro Gly Gly Gly Gln Val Glu Val Lys Ser Glu Lys Leu
        35                  40                  45

Asp Phe Lys Asp Arg Val Gln Ser Lys Ile Gly Ser Leu Asp Asn Ile
    50                  55                  60

Thr His Val Pro Gly Gly Gly Asn Lys Lys Ile Glu Thr His Lys Leu
65                  70                  75                  80

Thr Phe Arg Glu Asn Ala Lys Ala Lys Thr
                85                  90

<210> SEQ ID NO 6
<211> LENGTH: 93
<212> TYPE: PRT
<213> ORGANISM: Homo sapiens

<400> SEQUENCE: 6

Ile Lys His Val Pro Gly Gly Gly Ser Val Gln Ile Val Tyr Lys Pro
1               5                   10                  15

Val Asp Leu Ser Lys Val Thr Ser Lys Cys Gly Ser Leu Gly Asn Ile
            20                  25                  30

His His Lys Pro Gly Gly Gly Gln Val Glu Val Lys Ser Glu Lys Leu
        35                  40                  45

Asp Phe Lys Asp Arg Val Gln Ser Lys Ile Gly Ser Leu Asp Asn Ile
    50                  55                  60

Thr His Val Pro Gly Gly Gly Asn Lys Lys Ile Glu Thr His Lys Leu
65                  70                  75                  80

Thr Phe Arg Glu Asn Ala Lys Ala Lys Thr Asp His Gly
                85                  90

<210> SEQ ID NO 7
<211> LENGTH: 96
<212> TYPE: PRT
<213> ORGANISM: Homo sapiens

<400> SEQUENCE: 7

Ile Lys His Val Pro Gly Gly Gly Ser Val Gln Ile Val Tyr Lys Pro
1               5                   10                  15

Val Asp Leu Ser Lys Val Thr Ser Lys Cys Gly Ser Leu Gly Asn Ile
```

```
                20                  25                  30
His His Lys Pro Gly Gly Gln Val Glu Val Lys Ser Glu Lys Leu
        35                  40                  45

Asp Phe Lys Asp Arg Val Gln Ser Lys Ile Gly Ser Leu Asp Asn Ile
    50                  55                  60

Thr His Val Pro Gly Gly Asn Lys Lys Ile Glu Thr His Lys Leu
65                  70                  75                  80

Thr Phe Arg Glu Asn Ala Lys Ala Lys Thr Asp His Gly Ala Glu Ile
                85                  90                  95
```

<210> SEQ ID NO 8
<211> LENGTH: 102
<212> TYPE: PRT
<213> ORGANISM: Homo sapiens

<400> SEQUENCE: 8

```
Ile Lys His Val Pro Gly Gly Gly Ser Val Gln Ile Val Tyr Lys Pro
1               5                   10                  15

Val Asp Leu Ser Lys Val Thr Ser Lys Cys Gly Ser Leu Gly Asn Ile
                20                  25                  30

His His Lys Pro Gly Gly Gly Gln Val Glu Val Lys Ser Glu Lys Leu
            35                  40                  45

Asp Phe Lys Asp Arg Val Gln Ser Lys Ile Gly Ser Leu Asp Asn Ile
    50                  55                  60

Thr His Val Pro Gly Gly Gly Asn Lys Lys Ile Glu Thr His Lys Leu
65                  70                  75                  80

Thr Phe Arg Glu Asn Ala Lys Ala Lys Thr Asp His Gly Ala Glu Ile
                85                  90                  95

Val Tyr Lys Ser Pro Val
            100
```

<210> SEQ ID NO 9
<211> LENGTH: 105
<212> TYPE: PRT
<213> ORGANISM: Homo sapiens

<400> SEQUENCE: 9

```
Ile Lys His Val Pro Gly Gly Gly Ser Val Gln Ile Val Tyr Lys Pro
1               5                   10                  15

Val Asp Leu Ser Lys Val Thr Ser Lys Cys Gly Ser Leu Gly Asn Ile
                20                  25                  30

His His Lys Pro Gly Gly Gly Gln Val Glu Val Lys Ser Glu Lys Leu
            35                  40                  45

Asp Phe Lys Asp Arg Val Gln Ser Lys Ile Gly Ser Leu Asp Asn Ile
    50                  55                  60

Thr His Val Pro Gly Gly Gly Asn Lys Lys Ile Glu Thr His Lys Leu
65                  70                  75                  80

Thr Phe Arg Glu Asn Ala Lys Ala Lys Thr Asp His Gly Ala Glu Ile
                85                  90                  95

Val Tyr Lys Ser Pro Val Val Ser Gly
            100                 105
```

<210> SEQ ID NO 10
<211> LENGTH: 95
<212> TYPE: PRT
<213> ORGANISM: Homo sapiens

<400> SEQUENCE: 10

```
Leu Lys His Gln Pro Gly Gly Lys Val Gln Ile Val Tyr Lys Pro
1               5                  10                 15

Val Asp Leu Ser Lys Val Thr Ser Lys Cys Gly Ser Leu Gly Asn Ile
            20                  25                  30

His His Lys Pro Gly Gly Gln Val Glu Val Lys Ser Glu Lys Leu
        35                  40                  45

Asp Phe Lys Asp Arg Val Gln Ser Lys Ile Gly Ser Leu Asp Asn Ile
    50                  55                  60

Thr His Val Pro Gly Gly Asn Lys Lys Ile Glu Thr His Lys Leu
65              70                  75                  80

Thr Phe Arg Glu Asn Ala Lys Ala Lys Thr Asp His Gly Ala Glu
            85                  90                  95

<210> SEQ ID NO 11
<211> LENGTH: 265
<212> TYPE: PRT
<213> ORGANISM: Homo sapiens

<400> SEQUENCE: 11

Met Val Ser Lys Ser Lys Asp Gly Thr Gly Ser Asp Asp Lys Lys Ala
1               5                   10                  15

Lys Gly Ala Asp Gly Lys Thr Lys Ile Ala Thr Pro Arg Gly Ala Ala
            20                  25                  30

Pro Pro Gly Gln Lys Gly Gln Ala Asn Ala Thr Arg Ile Pro Ala Lys
        35                  40                  45

Thr Pro Pro Ala Pro Lys Thr Pro Ser Ser Gly Glu Pro Pro Lys
    50                  55                  60

Ser Gly Asp Arg Ser Gly Tyr Ser Ser Pro Gly Ser Pro Gly Thr Pro
65              70                  75                  80

Gly Ser Arg Ser Arg Thr Pro Ser Leu Pro Thr Pro Thr Arg Glu
            85                  90                  95

Pro Lys Lys Val Ala Val Val Arg Thr Pro Pro Lys Ser Pro Ser Ser
                100                 105                 110

Ala Lys Ser Arg Leu Gln Thr Ala Pro Val Pro Met Pro Asp Leu Lys
        115                 120                 125

Asn Val Lys Ser Lys Ile Gly Ser Thr Glu Asn Leu Lys His Gln Pro
130                 135                 140

Gly Gly Gly Lys Val Gln Ile Ile Asn Lys Lys Leu Asp Leu Ser Asn
145                 150                 155                 160

Val Gln Ser Lys Cys Gly Ser Lys Asp Asn Ile Lys His Val Pro Gly
                165                 170                 175

Gly Gly Ser Val Gln Ile Val Tyr Lys Pro Val Asp Leu Ser Lys Val
            180                 185                 190

Thr Ser Lys Cys Gly Ser Leu Gly Asn Ile His His Lys Pro Gly Gly
        195                 200                 205

Gly Gln Val Glu Val Lys Ser Glu Lys Leu Asp Phe Lys Asp Arg Val
    210                 215                 220

Gln Ser Lys Ile Gly Ser Leu Asp Asn Ile Thr His Val Pro Gly Gly
225                 230                 235                 240

Gly Asn Lys Lys Ile Glu Thr His Lys Leu Thr Phe Arg Glu Asn Ala
                245                 250                 255

Lys Ala Lys Thr Asp His Gly Ala Glu
            260                 265
```

```
<210> SEQ ID NO 12
<211> LENGTH: 241
<212> TYPE: PRT
<213> ORGANISM: Homo sapiens

<400> SEQUENCE: 12

Ile Ala Thr Pro Arg Gly Ala Ala Pro Pro Gly Gln Lys Gly Gln Ala
1               5                   10                  15

Asn Ala Thr Arg Ile Pro Ala Lys Thr Pro Pro Ala Pro Lys Thr Pro
            20                  25                  30

Pro Ser Ser Gly Glu Pro Pro Lys Ser Gly Asp Arg Ser Gly Tyr Ser
        35                  40                  45

Ser Pro Gly Ser Pro Gly Thr Pro Gly Ser Arg Ser Arg Thr Pro Ser
    50                  55                  60

Leu Pro Thr Pro Pro Thr Arg Glu Pro Lys Lys Val Ala Val Val Arg
65                  70                  75                  80

Thr Pro Pro Lys Ser Pro Ser Ser Ala Lys Ser Arg Leu Gln Thr Ala
                85                  90                  95

Pro Val Pro Met Pro Asp Leu Lys Asn Val Lys Ser Lys Ile Gly Ser
            100                 105                 110

Thr Glu Asn Leu Lys His Gln Pro Gly Gly Gly Lys Val Gln Ile Ile
        115                 120                 125

Asn Lys Lys Leu Asp Leu Ser Asn Val Gln Ser Lys Cys Gly Ser Lys
    130                 135                 140

Asp Asn Ile Lys His Val Pro Gly Gly Gly Ser Val Gln Ile Val Tyr
145                 150                 155                 160

Lys Pro Val Asp Leu Ser Lys Val Thr Ser Lys Cys Gly Ser Leu Gly
                165                 170                 175

Asn Ile His His Lys Pro Gly Gly Gly Gln Val Glu Val Lys Ser Glu
            180                 185                 190

Lys Leu Asp Phe Lys Asp Arg Val Gln Ser Lys Ile Gly Ser Leu Asp
        195                 200                 205

Asn Ile Thr His Val Pro Gly Gly Gly Asn Lys Lys Ile Glu Thr His
    210                 215                 220

Lys Leu Thr Phe Arg Glu Asn Ala Lys Ala Lys Thr Asp His Gly Ala
225                 230                 235                 240

Glu

<210> SEQ ID NO 13
<211> LENGTH: 295
<212> TYPE: PRT
<213> ORGANISM: Homo sapiens

<400> SEQUENCE: 13

Met Val Ser Lys Ser Lys Asp Gly Thr Gly Ser Asp Asp Lys Lys Ala
1               5                   10                  15

Lys Gly Ala Asp Gly Lys Thr Lys Ile Ala Thr Pro Arg Gly Ala Ala
            20                  25                  30

Pro Pro Gly Gln Lys Gly Gln Ala Asn Ala Thr Arg Ile Pro Ala Lys
        35                  40                  45

Thr Pro Pro Ala Pro Lys Thr Pro Pro Ser Ser Gly Glu Pro Pro Lys
    50                  55                  60

Ser Gly Asp Arg Ser Gly Tyr Ser Ser Pro Gly Ser Pro Gly Thr Pro
65                  70                  75                  80

Gly Ser Arg Ser Arg Thr Pro Ser Leu Pro Thr Pro Pro Thr Arg Glu
                85                  90                  95
```

```
Pro Lys Lys Val Ala Val Arg Thr Pro Lys Ser Pro Ser Ser
            100                 105                 110

Ala Lys Ser Arg Leu Gln Thr Ala Pro Val Pro Met Pro Asp Leu Lys
            115                 120                 125

Asn Val Lys Ser Lys Ile Gly Ser Thr Glu Asn Leu Lys His Gln Pro
130                 135                 140

Gly Gly Gly Lys Val Gln Ile Ile Asn Lys Lys Leu Asp Leu Ser Asn
145                 150                 155                 160

Val Gln Ser Lys Cys Gly Ser Lys Asp Asn Ile Lys His Val Pro Gly
                165                 170                 175

Gly Gly Ser Val Gln Ile Val Tyr Lys Pro Val Asp Leu Ser Lys Val
            180                 185                 190

Thr Ser Lys Cys Gly Ser Leu Gly Asn Ile His His Lys Pro Gly Gly
            195                 200                 205

Gly Gln Val Glu Val Lys Ser Glu Lys Leu Asp Phe Lys Asp Arg Val
            210                 215                 220

Gln Ser Lys Ile Gly Ser Leu Asp Asn Ile Thr His Val Pro Gly Gly
225                 230                 235                 240

Gly Asn Lys Lys Ile Glu Thr His Lys Leu Thr Phe Arg Glu Asn Ala
                245                 250                 255

Lys Ala Lys Thr Asp His Gly Ala Glu Ile Val Tyr Lys Ser Pro Val
            260                 265                 270

Val Ser Gly Asp Thr Ser Pro Arg His Leu Ser Asn Val Ser Ser Thr
            275                 280                 285

Gly Ser Ile Asp Met Val Asp
            290                 295

<210> SEQ ID NO 14
<211> LENGTH: 271
<212> TYPE: PRT
<213> ORGANISM: Homo sapiens

<400> SEQUENCE: 14

Ile Ala Thr Pro Arg Gly Ala Ala Pro Pro Gly Gln Lys Gly Gln Ala
1               5                   10                  15

Asn Ala Thr Arg Ile Pro Ala Lys Thr Pro Pro Ala Pro Lys Thr Pro
            20                  25                  30

Pro Ser Ser Gly Glu Pro Pro Lys Ser Gly Asp Arg Ser Gly Tyr Ser
        35                  40                  45

Ser Pro Gly Ser Pro Gly Thr Pro Gly Ser Arg Ser Arg Thr Pro Ser
    50                  55                  60

Leu Pro Thr Pro Pro Thr Arg Glu Pro Lys Lys Val Ala Val Val Arg
65                  70                  75                  80

Thr Pro Pro Lys Ser Pro Ser Ser Ala Lys Ser Arg Leu Gln Thr Ala
                85                  90                  95

Pro Val Pro Met Pro Asp Leu Lys Asn Val Lys Ser Lys Ile Gly Ser
            100                 105                 110

Thr Glu Asn Leu Lys His Gln Pro Gly Gly Gly Lys Val Gln Ile Ile
        115                 120                 125

Asn Lys Lys Leu Asp Leu Ser Asn Val Gln Ser Lys Cys Gly Ser Lys
    130                 135                 140

Asp Asn Ile Lys His Val Pro Gly Gly Gly Ser Val Gln Ile Val Tyr
145                 150                 155                 160

Lys Pro Val Asp Leu Ser Lys Val Thr Ser Lys Cys Gly Ser Leu Gly
```

```
                    165                 170                 175

Asn Ile His His Lys Pro Gly Gly Gln Val Glu Val Lys Ser Glu
            180                 185                 190

Lys Leu Asp Phe Lys Asp Arg Val Gln Ser Lys Ile Gly Ser Leu Asp
        195                 200                 205

Asn Ile Thr His Val Pro Gly Gly Asn Lys Lys Ile Glu Thr His
    210                 215                 220

Lys Leu Thr Phe Arg Glu Asn Ala Lys Ala Lys Thr Asp His Gly Ala
225                 230                 235                 240

Glu Ile Val Tyr Lys Ser Pro Val Val Ser Gly Asp Thr Ser Pro Arg
                245                 250                 255

His Leu Ser Asn Val Ser Ser Thr Gly Ser Ile Asp Met Val Asp
            260                 265                 270

<210> SEQ ID NO 15
<211> LENGTH: 210
<212> TYPE: PRT
<213> ORGANISM: Homo sapiens

<400> SEQUENCE: 15

Ile Ala Thr Pro Arg Gly Ala Ala Pro Pro Gly Gln Lys Gly Gln Ala
1               5                   10                  15

Asn Ala Thr Arg Ile Pro Ala Lys Thr Pro Ala Pro Lys Thr Pro
            20                  25                  30

Pro Ser Ser Gly Glu Pro Pro Lys Ser Gly Asp Arg Ser Gly Tyr Ser
        35                  40                  45

Ser Pro Gly Ser Pro Gly Thr Pro Gly Ser Arg Ser Arg Thr Pro Ser
    50                  55                  60

Leu Pro Thr Pro Pro Thr Arg Glu Pro Lys Lys Val Ala Val Val Arg
65                  70                  75                  80

Thr Pro Pro Lys Ser Pro Ser Ser Ala Lys Ser Arg Leu Gln Thr Ala
                85                  90                  95

Pro Val Pro Met Pro Asp Leu Lys Asn Val Lys Ser Lys Ile Gly Ser
            100                 105                 110

Thr Glu Asn Leu Lys His Gln Pro Gly Gly Gly Lys Val Gln Ile Val
        115                 120                 125

Tyr Lys Pro Val Asp Leu Ser Lys Val Thr Ser Lys Cys Gly Ser Leu
    130                 135                 140

Gly Asn Ile His His Lys Pro Gly Gly Gln Val Glu Val Lys Ser
145                 150                 155                 160

Glu Lys Leu Asp Phe Lys Asp Arg Val Gln Ser Lys Ile Gly Ser Leu
                165                 170                 175

Asp Asn Ile Thr His Val Pro Gly Gly Gly Asn Lys Lys Ile Glu Thr
            180                 185                 190

His Lys Leu Thr Phe Arg Glu Asn Ala Lys Ala Lys Thr Asp His Gly
        195                 200                 205

Ala Glu
    210

<210> SEQ ID NO 16
<211> LENGTH: 234
<212> TYPE: PRT
<213> ORGANISM: Homo sapiens

<400> SEQUENCE: 16

Met Val Ser Lys Ser Lys Asp Gly Thr Gly Ser Asp Asp Lys Lys Ala
```

```
               1               5                  10                 15
            Lys Gly Ala Asp Gly Lys Thr Lys Ile Ala Thr Pro Arg Gly Ala Ala
                           20                  25                 30

Pro Pro Gly Gln Lys Gly Gln Ala Asn Ala Thr Arg Ile Pro Ala Lys
                           35                  40                 45

Thr Pro Pro Ala Pro Lys Thr Pro Pro Ser Ser Gly Glu Pro Pro Lys
                 50                       55                 60

Ser Gly Asp Arg Ser Gly Tyr Ser Ser Pro Gly Ser Pro Gly Thr Pro
            65                       70                  75                 80

Gly Ser Arg Ser Arg Thr Pro Ser Leu Pro Thr Pro Thr Arg Glu
                                85                 90                 95

Pro Lys Lys Val Ala Val Arg Thr Pro Pro Lys Ser Pro Ser Ser
                                100                 105                110

Ala Lys Ser Arg Leu Gln Thr Ala Pro Val Pro Met Pro Asp Leu Lys
                           115                 120                125

Asn Val Lys Ser Lys Ile Gly Ser Thr Glu Asn Leu Lys His Gln Pro
                      130                 135                140

Gly Gly Gly Lys Val Gln Ile Val Tyr Lys Pro Val Asp Leu Ser Lys
            145                 150                 155                160

Val Thr Ser Lys Cys Gly Ser Leu Gly Asn Ile His His Lys Pro Gly
                                165                 170                175

Gly Gly Gln Val Glu Val Lys Ser Glu Lys Leu Asp Phe Lys Asp Arg
                           180                 185                190

Val Gln Ser Lys Ile Gly Ser Leu Asp Asn Ile Thr His Val Pro Gly
                      195                 200                205

Gly Gly Asn Lys Lys Ile Glu Thr His Lys Leu Thr Phe Arg Glu Asn
                      210                 215                220

Ala Lys Ala Lys Thr Asp His Gly Ala Glu
            225                 230

<210> SEQ ID NO 17
            <211> LENGTH: 240
            <212> TYPE: PRT
            <213> ORGANISM: Homo sapiens

<400> SEQUENCE: 17

Ile Ala Thr Pro Arg Gly Ala Ala Pro Pro Gly Gln Lys Gly Gln Ala
            1               5                  10                 15

Asn Ala Thr Arg Ile Pro Ala Lys Thr Pro Pro Ala Pro Lys Thr Pro
                           20                  25                 30

Pro Ser Ser Gly Glu Pro Pro Lys Ser Gly Asp Arg Ser Gly Tyr Ser
                           35                  40                 45

Ser Pro Gly Ser Pro Gly Thr Pro Gly Ser Arg Ser Arg Thr Pro Ser
                 50                       55                 60

Leu Pro Thr Pro Pro Thr Arg Glu Pro Lys Lys Val Ala Val Val Arg
            65                       70                  75                 80

Thr Pro Pro Lys Ser Pro Ser Ser Ala Lys Ser Arg Leu Gln Thr Ala
                                85                 90                 95

Pro Val Pro Met Pro Asp Leu Lys Asn Val Lys Ser Lys Ile Gly Ser
                           100                 105                110

Thr Glu Asn Leu Lys His Gln Pro Gly Gly Gly Lys Val Gln Ile Val
                      115                 120                125

Tyr Lys Pro Val Asp Leu Ser Lys Val Thr Ser Lys Cys Gly Ser Leu
                      130                 135                140
```

```
Gly Asn Ile His His Lys Pro Gly Gly Gln Val Glu Val Lys Ser
145                 150                 155                 160

Glu Lys Leu Asp Phe Lys Asp Arg Val Gln Ser Lys Ile Gly Ser Leu
            165                 170                 175

Asp Asn Ile Thr His Val Pro Gly Gly Gly Asn Lys Lys Ile Glu Thr
            180                 185                 190

His Lys Leu Thr Phe Arg Glu Asn Ala Lys Ala Lys Thr Asp His Gly
            195                 200                 205

Ala Glu Ile Val Tyr Lys Ser Pro Val Val Ser Gly Asp Thr Ser Pro
            210                 215                 220

Arg His Leu Ser Asn Val Ser Ser Thr Gly Ser Ile Asp Met Val Asp
225                 230                 235                 240

<210> SEQ ID NO 18
<211> LENGTH: 264
<212> TYPE: PRT
<213> ORGANISM: Homo sapiens

<400> SEQUENCE: 18

Met Val Ser Lys Ser Lys Asp Gly Thr Gly Ser Asp Asp Lys Lys Ala
1               5                   10                  15

Lys Gly Ala Asp Gly Lys Thr Lys Ile Ala Thr Pro Arg Gly Ala Ala
            20                  25                  30

Pro Pro Gly Gln Lys Gly Gln Ala Asn Ala Thr Arg Ile Pro Ala Lys
        35                  40                  45

Thr Pro Pro Ala Pro Lys Thr Pro Pro Ser Ser Gly Glu Pro Pro Lys
    50                  55                  60

Ser Gly Asp Arg Ser Gly Tyr Ser Ser Pro Gly Ser Pro Gly Thr Pro
65                  70                  75                  80

Gly Ser Arg Ser Arg Thr Pro Ser Leu Pro Thr Pro Pro Thr Arg Glu
                85                  90                  95

Pro Lys Lys Val Ala Val Val Arg Thr Pro Pro Lys Ser Pro Ser Ser
            100                 105                 110

Ala Lys Ser Arg Leu Gln Thr Ala Pro Val Pro Met Pro Asp Leu Lys
        115                 120                 125

Asn Val Lys Ser Lys Ile Gly Ser Thr Glu Asn Leu Lys His Gln Pro
    130                 135                 140

Gly Gly Gly Lys Val Gln Ile Val Tyr Lys Pro Val Asp Leu Ser Lys
145                 150                 155                 160

Val Thr Ser Lys Cys Gly Ser Leu Gly Asn Ile His His Lys Pro Gly
                165                 170                 175

Gly Gly Gln Val Glu Val Lys Ser Glu Lys Leu Asp Phe Lys Asp Arg
            180                 185                 190

Val Gln Ser Lys Ile Gly Ser Leu Asp Asn Ile Thr His Val Pro Gly
        195                 200                 205

Gly Gly Asn Lys Lys Ile Glu Thr His Lys Leu Thr Phe Arg Glu Asn
    210                 215                 220

Ala Lys Ala Lys Thr Asp His Gly Ala Glu Ile Val Tyr Lys Ser Pro
225                 230                 235                 240

Val Val Ser Gly Asp Thr Ser Pro Arg His Leu Ser Asn Val Ser Ser
                245                 250                 255

Thr Gly Ser Ile Asp Met Val Asp
            260

<210> SEQ ID NO 19
```

<211> LENGTH: 373
<212> TYPE: PRT
<213> ORGANISM: Homo sapiens

<400> SEQUENCE: 19

```
Gln Glu Phe Glu Val Met Glu Asp His Ala Gly Thr Tyr Gly Leu Gly
1               5                   10                  15

Asp Arg Lys Asp Gln Gly Gly Tyr Thr Met His Gln Asp Gln Glu Gly
            20                  25                  30

Asp Thr Asp Ala Gly Leu Lys Ala Glu Glu Ala Gly Ile Gly Asp Thr
        35                  40                  45

Pro Ser Leu Glu Asp Glu Ala Ala Gly His Val Thr Gln Ala Arg Met
50                  55                  60

Val Ser Lys Ser Lys Asp Gly Thr Gly Ser Asp Asp Lys Lys Ala Lys
65                  70                  75                  80

Gly Ala Asp Gly Lys Thr Lys Ile Ala Thr Pro Arg Gly Ala Ala Pro
                85                  90                  95

Pro Gly Gln Lys Gly Gln Ala Asn Ala Thr Arg Ile Pro Ala Lys Thr
            100                 105                 110

Pro Pro Ala Pro Lys Thr Pro Pro Ser Ser Gly Glu Pro Pro Lys Ser
        115                 120                 125

Gly Asp Arg Ser Gly Tyr Ser Ser Pro Gly Ser Pro Gly Thr Pro Gly
130                 135                 140

Ser Arg Ser Arg Thr Pro Ser Leu Pro Thr Pro Pro Thr Arg Glu Pro
145                 150                 155                 160

Lys Lys Val Ala Val Arg Thr Pro Pro Lys Ser Pro Ser Ser Ala
                165                 170                 175

Lys Ser Arg Leu Gln Thr Ala Pro Val Pro Met Pro Asp Leu Lys Asn
            180                 185                 190

Val Lys Ser Lys Ile Gly Ser Thr Glu Asn Leu Lys His Gln Pro Gly
        195                 200                 205

Gly Gly Lys Val Gln Ile Ile Asn Lys Lys Leu Asp Leu Ser Asn Val
210                 215                 220

Gln Ser Lys Cys Gly Ser Lys Asp Asn Ile Lys His Val Pro Gly Gly
225                 230                 235                 240

Gly Ser Val Gln Ile Val Tyr Lys Pro Val Asp Leu Ser Lys Val Thr
                245                 250                 255

Ser Lys Cys Gly Ser Leu Gly Asn Ile His His Lys Pro Gly Gly Gly
            260                 265                 270

Gln Val Glu Val Lys Ser Glu Lys Leu Asp Phe Lys Asp Arg Val Gln
        275                 280                 285

Ser Lys Ile Gly Ser Leu Asp Asn Ile Thr His Val Pro Gly Gly Gly
290                 295                 300

Asn Lys Lys Ile Glu Thr His Lys Leu Thr Phe Arg Glu Asn Ala Lys
305                 310                 315                 320

Ala Lys Thr Asp His Gly Ala Glu Ile Val Tyr Lys Ser Pro Val Val
                325                 330                 335

Ser Gly Asp Thr Ser Pro Arg His Leu Ser Asn Val Ser Ser Thr Gly
            340                 345                 350

Ser Ile Asp Met Val Asp Ser Pro Gln Leu Ala Thr Leu Ala Asp Glu
        355                 360                 365

Val Ser Ala Ser Leu
        370
```

<210> SEQ ID NO 20
<211> LENGTH: 342
<212> TYPE: PRT
<213> ORGANISM: Homo sapiens

<400> SEQUENCE: 20

Gln Glu Phe Glu Val Met Glu Asp His Ala Gly Thr Tyr Gly Leu Gly
1               5                   10                  15

Asp Arg Lys Asp Gln Gly Gly Tyr Thr Met His Gln Asp Gln Glu Gly
            20                  25                  30

Asp Thr Asp Ala Gly Leu Lys Ala Glu Glu Ala Gly Ile Gly Asp Thr
        35                  40                  45

Pro Ser Leu Glu Asp Glu Ala Ala Gly His Val Thr Gln Ala Arg Met
50                  55                  60

Val Ser Lys Ser Lys Asp Gly Thr Gly Ser Asp Asp Lys Lys Ala Lys
65                  70                  75                  80

Gly Ala Asp Gly Lys Thr Lys Ile Ala Thr Pro Arg Gly Ala Ala Pro
                85                  90                  95

Pro Gly Gln Lys Gly Gln Ala Asn Ala Thr Arg Ile Pro Ala Lys Thr
            100                 105                 110

Pro Pro Ala Pro Lys Thr Pro Pro Ser Ser Gly Glu Pro Pro Lys Ser
        115                 120                 125

Gly Asp Arg Ser Gly Tyr Ser Ser Pro Gly Ser Pro Gly Thr Pro Gly
130                 135                 140

Ser Arg Ser Arg Thr Pro Ser Leu Pro Thr Pro Pro Thr Arg Glu Pro
145                 150                 155                 160

Lys Lys Val Ala Val Val Arg Thr Pro Pro Lys Ser Pro Ser Ser Ala
                165                 170                 175

Lys Ser Arg Leu Gln Thr Ala Pro Val Pro Met Pro Asp Leu Lys Asn
            180                 185                 190

Val Lys Ser Lys Ile Gly Ser Thr Glu Asn Leu Lys His Gln Pro Gly
        195                 200                 205

Gly Gly Lys Val Gln Ile Val Tyr Lys Pro Val Asp Leu Ser Lys Val
210                 215                 220

Thr Ser Lys Cys Gly Ser Leu Gly Asn Ile His His Lys Pro Gly Gly
225                 230                 235                 240

Gly Gln Val Glu Val Lys Ser Glu Lys Leu Asp Phe Lys Asp Arg Val
                245                 250                 255

Gln Ser Lys Ile Gly Ser Leu Asp Asn Ile Thr His Val Pro Gly Gly
            260                 265                 270

Gly Asn Lys Lys Ile Glu Thr His Lys Leu Thr Phe Arg Glu Asn Ala
        275                 280                 285

Lys Ala Lys Thr Asp His Gly Ala Glu Ile Val Tyr Lys Ser Pro Val
290                 295                 300

Val Ser Gly Asp Thr Ser Pro Arg His Leu Ser Asn Val Ser Ser Thr
305                 310                 315                 320

Gly Ser Ile Asp Met Val Asp Ser Pro Gln Leu Ala Thr Leu Ala Asp
                325                 330                 335

Glu Val Ser Ala Ser Leu
            340

<210> SEQ ID NO 21
<211> LENGTH: 66
<212> TYPE: PRT
<213> ORGANISM: Homo sapiens

```
<400> SEQUENCE: 21

Gly Asn Ile His His Lys Pro Gly Gly Gly Gln Val Glu Val Lys Ser
1               5                   10                  15

Glu Lys Leu Asp Phe Lys Asp Arg Val Gln Ser Lys Ile Gly Ser Leu
            20                  25                  30

Asp Asn Ile Thr His Val Pro Gly Gly Asn Lys Lys Ile Glu Thr
        35                  40                  45

His Lys Leu Thr Phe Arg Glu Asn Ala Lys Ala Lys Thr Asp His Gly
    50                  55                  60

Ala Glu
65

<210> SEQ ID NO 22
<211> LENGTH: 86
<212> TYPE: PRT
<213> ORGANISM: Homo sapiens

<400> SEQUENCE: 22

Val Gln Ile Val Tyr Lys Pro Val Asp Leu Ser Lys Val Thr Ser Lys
1               5                   10                  15

Cys Gly Ser Leu Gly Asn Ile His His Lys Pro Gly Gly Gly Gln Val
            20                  25                  30

Glu Val Lys Ser Glu Lys Leu Asp Phe Lys Asp Arg Val Gln Ser Lys
        35                  40                  45

Ile Gly Ser Leu Asp Asn Ile Thr His Val Pro Gly Gly Asn Lys
    50                  55                  60

Lys Ile Glu Thr His Lys Leu Thr Phe Arg Glu Asn Ala Lys Ala Lys
65                  70                  75                  80

Thr Asp His Gly Ala Glu
                85

<210> SEQ ID NO 23
<211> LENGTH: 76
<212> TYPE: PRT
<213> ORGANISM: Homo sapiens

<400> SEQUENCE: 23

Ser Lys Val Thr Ser Lys Cys Gly Ser Leu Gly Asn Ile His His Lys
1               5                   10                  15

Pro Gly Gly Gly Gln Val Glu Val Lys Ser Glu Lys Leu Asp Phe Lys
            20                  25                  30

Asp Arg Val Gln Ser Lys Ile Gly Ser Leu Asp Asn Ile Thr His Val
        35                  40                  45

Pro Gly Gly Asn Lys Lys Ile Glu Thr His Lys Leu Thr Phe Arg
    50                  55                  60

Glu Asn Ala Lys Ala Lys Thr Asp His Gly Ala Glu
65                  70                  75

<210> SEQ ID NO 24
<211> LENGTH: 71
<212> TYPE: PRT
<213> ORGANISM: Homo sapiens

<400> SEQUENCE: 24

Lys Cys Gly Ser Leu Gly Asn Ile His His Lys Pro Gly Gly Gly Gln
1               5                   10                  15

Val Glu Val Lys Ser Glu Lys Leu Asp Phe Lys Asp Arg Val Gln Ser
            20                  25                  30
```

-continued

Lys Ile Gly Ser Leu Asp Asn Ile Thr His Val Pro Gly Gly Asn
            35                  40                  45

Lys Lys Ile Glu Thr His Lys Leu Thr Phe Arg Glu Asn Ala Lys Ala
    50                  55                  60

Lys Thr Asp His Gly Ala Glu
65                  70

<210> SEQ ID NO 25
<211> LENGTH: 79
<212> TYPE: PRT
<213> ORGANISM: Homo sapiens

<400> SEQUENCE: 25

Ile Lys His Val Pro Gly Gly Gly Lys Cys Gly Ser Leu Gly Asn Ile
1               5                   10                  15

His His Lys Pro Gly Gly Gly Gln Val Glu Val Lys Ser Glu Lys Leu
            20                  25                  30

Asp Phe Lys Asp Arg Val Gln Ser Lys Ile Gly Ser Leu Asp Asn Ile
        35                  40                  45

Thr His Val Pro Gly Gly Gly Asn Lys Lys Ile Glu Thr His Lys Leu
    50                  55                  60

Thr Phe Arg Glu Asn Ala Lys Ala Lys Thr Asp His Gly Ala Glu
65                  70                  75

<210> SEQ ID NO 26
<211> LENGTH: 88
<212> TYPE: PRT
<213> ORGANISM: Homo sapiens

<400> SEQUENCE: 26

Ile Lys His Val Pro Gly Gly Gly Ser Val Gln Ile Val Tyr Lys Pro
1               5                   10                  15

Val Lys Cys Gly Ser Leu Gly Asn Ile His His Lys Pro Gly Gly Gly
            20                  25                  30

Gln Val Glu Val Lys Ser Glu Lys Leu Asp Phe Lys Asp Arg Val Gln
        35                  40                  45

Ser Lys Ile Gly Ser Leu Asp Asn Ile Thr His Val Pro Gly Gly Gly
    50                  55                  60

Asn Lys Lys Ile Glu Thr His Lys Leu Thr Phe Arg Glu Asn Ala Lys
65                  70                  75                  80

Ala Lys Thr Asp His Gly Ala Glu
                85

<210> SEQ ID NO 27
<211> LENGTH: 90
<212> TYPE: PRT
<213> ORGANISM: Homo sapiens

<400> SEQUENCE: 27

Ile Lys His Val Pro Gly Gly Gly Ser Val Gln Ile Val Tyr Lys Pro
1               5                   10                  15

Val Asp Leu Ser Lys Val Thr Ser Gly Asn Ile His His Lys Pro Gly
            20                  25                  30

Gly Gly Gln Val Glu Val Lys Ser Glu Lys Leu Asp Phe Lys Asp Arg
        35                  40                  45

Val Gln Ser Lys Ile Gly Ser Leu Asp Asn Ile Thr His Val Pro Gly
    50                  55                  60

Gly Gly Asn Lys Lys Ile Glu Thr His Lys Leu Thr Phe Arg Glu Asn
65                  70                  75                  80

Ala Lys Ala Lys Thr Asp His Gly Ala Glu
                85                  90

<210> SEQ ID NO 28
<211> LENGTH: 29
<212> TYPE: PRT
<213> ORGANISM: Homo sapiens

<400> SEQUENCE: 28

Ile Lys His Val Pro Gly Gly Gly Ser Val Gln Ile Val Tyr Lys Pro
1               5                   10                  15

Val Asp Leu Ser Lys Val Thr Ser Lys Cys Gly Ser Leu
            20                  25

<210> SEQ ID NO 29
<211> LENGTH: 9
<212> TYPE: PRT
<213> ORGANISM: Homo sapiens

<400> SEQUENCE: 29

Ile Lys His Val Pro Gly Gly Gly Ser
1               5

<210> SEQ ID NO 30
<211> LENGTH: 19
<212> TYPE: PRT
<213> ORGANISM: Homo sapiens

<400> SEQUENCE: 30

Ile Lys His Val Pro Gly Gly Gly Ser Val Gln Ile Val Tyr Lys Pro
1               5                   10                  15

Val Asp Leu

<210> SEQ ID NO 31
<211> LENGTH: 24
<212> TYPE: PRT
<213> ORGANISM: Homo sapiens

<400> SEQUENCE: 31

Ile Lys His Val Pro Gly Gly Gly Ser Val Gln Ile Val Tyr Lys Pro
1               5                   10                  15

Val Asp Leu Ser Lys Val Thr Ser
            20

<210> SEQ ID NO 32
<211> LENGTH: 16
<212> TYPE: PRT
<213> ORGANISM: Homo sapiens

<400> SEQUENCE: 32

Ser Val Gln Ile Val Tyr Lys Pro Val Asp Leu Ser Lys Val Thr Ser
1               5                   10                  15

<210> SEQ ID NO 33
<211> LENGTH: 7
<212> TYPE: PRT
<213> ORGANISM: Homo sapiens

<400> SEQUENCE: 33

Asp Leu Ser Lys Val Thr Ser
1               5

<210> SEQ ID NO 34
<211> LENGTH: 5
<212> TYPE: PRT
<213> ORGANISM: Homo sapiens

<400> SEQUENCE: 34

Lys Cys Gly Ser Leu
1               5

<210> SEQ ID NO 35
<211> LENGTH: 383
<212> TYPE: PRT
<213> ORGANISM: Homo sapiens

<400> SEQUENCE: 35

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
        275                 280                 285

Lys Asp Arg Val Gln Ser Lys Ile Gly Ser Leu Asp Asn Ile Thr His
    290                 295                 300

Val Pro Gly Gly Gly Asn Lys Lys Ile Glu Thr His Lys Leu Thr Phe
305                 310                 315                 320

```
Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350

Val Ser Thr Gly Ser Ile Asp Met Val Asp Ser Pro Gln Leu Ala
        355                 360                 365

Thr Leu Ala Asp Glu Val Ser Ala Ser Leu Ala Lys Gln Gly Leu
    370                 375                 380

<210> SEQ ID NO 36
<211> LENGTH: 352
<212> TYPE: PRT
<213> ORGANISM: Homo sapiens

<400> SEQUENCE: 36

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Val Tyr Lys Pro Val
    210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
            260                 265                 270

His Val Pro Gly Gly Gly Asn Lys Lys Ile Glu Thr His Lys Leu Thr
        275                 280                 285

Phe Arg Glu Asn Ala Lys Ala Lys Thr Asp His Gly Ala Glu Ile Val
    290                 295                 300

Tyr Lys Ser Pro Val Val Ser Gly Asp Thr Ser Pro Arg His Leu Ser
```

-continued

```
            305                 310                 315                 320
Asn Val Ser Ser Thr Gly Ser Ile Asp Met Val Asp Ser Pro Gln Leu
                    325                 330                 335

Ala Thr Leu Ala Asp Glu Val Ser Ala Ser Leu Ala Lys Gln Gly Leu
                    340                 345                 350
```